(12) United States Patent
Lakshmanan et al.

(10) Patent No.: US 12,370,272 B2
(45) Date of Patent: Jul. 29, 2025

(54) GAS-FILLED STRUCTURES AND RELATED COMPOSITIONS, METHODS AND SYSTEMS TO IMAGE A TARGET SITE

(71) Applicant: CALIFORNIA INSTITUTE OF TECHNOLOGY, Pasadena, CA (US)

(72) Inventors: Anupama Lakshmanan, Pasadena, CA (US); Arash Farhadi, Pasadena, CA (US); Suchita P. Nety, Sunnyvale, CA (US); Raymond W. Bourdeau, Watertown, MA (US); Mikhail Shapiro, Los Angeles, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 152 days.

(21) Appl. No.: 18/046,881

(22) Filed: Oct. 14, 2022

(65) Prior Publication Data
US 2023/0277695 A1   Sep. 7, 2023

Related U.S. Application Data

(63) Continuation of application No. 16/656,417, filed on Oct. 17, 2019, now Pat. No. 11,504,438, which is a continuation of application No. 15/613,104, filed on Jun. 2, 2017, now Pat. No. 10,493,172.

(60) Provisional application No. 62/344,498, filed on Jun. 2, 2016.

(51) Int. Cl.
| | |
|---|---|
| *A61K 49/22* | (2006.01) |
| *A61B 8/00* | (2006.01) |
| *A61B 8/08* | (2006.01) |
| *A61K 49/00* | (2006.01) |
| *C07K 14/195* | (2006.01) |

(52) U.S. Cl.
CPC ............ *A61K 49/223* (2013.01); *A61B 8/481* (2013.01); *A61K 49/0002* (2013.01); *A61K 49/0045* (2013.01); *A61K 49/0093* (2013.01); *A61K 49/221* (2013.01); *C07K 14/195* (2013.01); *A61B 8/5238* (2013.01); *C07K 2319/00* (2013.01)

(58) Field of Classification Search
CPC ............ A61K 49/0002; A61K 49/0045; A61K 49/0093; A61K 49/221; A61K 49/223
See application file for complete search history.

(56) References Cited

U.S. PATENT DOCUMENTS

| | | |
|---|---|---|
| 5,824,309 A | 10/1998 | Dassarma et al. |
| 11,446,523 B2 | 9/2022 | Bar-Zion et al. |
| 11,504,438 B2 | 11/2022 | Lakshmanan et al. |
| 11,761,008 B2 | 9/2023 | Farhadi et al. |
| 11,786,218 B2 | 10/2023 | Sawyer et al. |

(Continued)

OTHER PUBLICATIONS

Carson, M., et al., "His-tag impact on structure," Acta Cryst. (2007). D63, 295-301. 7 pages.

(Continued)

*Primary Examiner* — Brian T Gedeon
(74) *Attorney, Agent, or Firm* — Steinfl + Bruno LLP

(57) ABSTRACT

Gas vesicles, protein variants and related compositions methods and systems for singleplexed and/or multiplexed ultrasound imaging of a target site in which a gas vesicle provides contrast for the imaging which is modifiable by application of a selectable acoustic collapse pressure value of the gas vesicle.

21 Claims, 37 Drawing Sheets

Specification includes a Sequence Listing.

(56) References Cited

U.S. PATENT DOCUMENTS

| | | | |
|---|---|---|---|
| 12,109,440 B2 | 10/2024 | Bar-Zion et al. | |
| 2006/0216810 A1* | 9/2006 | Ju | A61K 49/223 435/243 |
| 2014/0288412 A1 | 9/2014 | Schwartz | |
| 2014/0288421 A1* | 9/2014 | Shapiro | A61B 8/481 600/431 |
| 2023/0139561 A1 | 5/2023 | Bar-Zion et al. | |
| 2023/0357780 A1 | 11/2023 | Farhadi et al. | |

OTHER PUBLICATIONS

"Enzyme" Definition, Mechanisms, and Nomenclature. Last updated on Mar. 4, 2024. 13 pages. Downloaded from website: www.britannica.com/science/enzyme. Retrieved Mar. 29, 2024.

Final Office Action for U.S. Appl. No. 17/334,953, filed May 31, 2021 on behalf of California Institute of Technology. Mailed on Mar. 7, 2024. 16 pages.

National Human Genome Research Institute, "Enzyme-less DNA base discrimination using solid-state nanopores with high-frequency integrated detection electronics" Project Description (Project End date: Jun. 30, 2019). Retrieved Mar. 29, 2024. Abstract Only. 5 pages.

Aguino, Carmen F. et al; "Single component biohybrid light-emitting diodes using a white-emitting fused protein." ACS Omega (2018) 3, p. 15829-15836.

Andreev, Y., et al., "Cyanogen Bromide Cleavage of Proteins in Salt and Buffer Solutions." *Analytical Biochemistry*, 2010. 1;407(1), p. 144-146. 3 pages.

Cesaratto, Francesca et al; "Engineered tobacco etch virus (TEV) protease active in the secretory pathway of mammalian cells." J. Biotech. (2015) 212, p. 159-166.

Ciechanover, A., et al., "Ubiquitin-Mediated Proteolysis: Biological Regulation via Destruction." *BioEssays*, 2000. 22(5), p. 442-451. 10 pages.

Corrected Notice of Allowability for U.S. Appl. No. 15/613,104, filed Jun. 2, 2017 on behalf of California Institute of Technology Mail Date: Sep. 9, 2019. 10 pages.

Corrected Notice of Allowability for U.S. Appl. No. 16/656,417, filed Oct. 17, 2019, on behalf of California Institute of Technology. Mail Date: Oct. 20, 2022. 4 Pages.

Corrected Notice of Allowability issued for U.S. Appl. No. 16/736,683, filed Jan. 7, 2020, on behalf of California Institute of Technology. Mail Date: Aug. 3, 2023. 7 Pages.

Corrected Notice of Allowability issued for U.S. Appl. No. 16/736,683, filed Jan. 7, 2020, on behalf of California Institute of Technology. Mail Date: Feb. 23, 2023. 7 Pages.

Dutka, P. et al., Structure of Anabaena flos-aquae gas vesicles revealed by cryo-ET. Structure, 31, 518-528. 18 pages. May 4, 2023. Website: doi.org/10.1016/j.str.2023.03.011.

"Enzyme" definition and meaning from Merriam Webster dictionary website. (Last updated Nov. 4, 2023).

"Enzyme" Definition, Mechanisms, and Nomenclature. Last updated on Dec. 10, 2023. 13 pages. Downloaded from website: www.britannica.com/science/enzyme.

"Enzyme" from NIH: National Human Genome Research Institute. Downloaded through the Wayback Machine with a date of Jul. 9, 2019. 1 page.

Final Office Action issued for U.S. Appl. No. 17/006,591, filed Aug. 28, 2020, on behalf of California Institute of Technology. (Mail Date: Nov. 9, 2023). 21 Pages.

Herrmann, Joerg et al; "Ubiquitin and ubiquitin-like proteins in protein regulation." Circulation Research (May 2007) 100, p. 1276-1291.

Jiang et al., "Tumor imaging by means of proteolytic activation of cell penetrating peptides," PNAS vol. 101 No. 51, Dec. 21, 2004. 17862-17872 (6 pages).

Lakshmanan, et al., "Acoustic biosensors for ultrasound imaging of enzyme activity," Supplementary Information in Nature Chemical Biology. Jul. 13, 2020. 3 Pages.

Lux, Jacques et al; "Thrombin-activatable microbubbles as potential ultrasound contrast agents for the detection of acute thrombosis." ACS Appl. Mater. Interfaces (Nov. 2017) 9(43), p. 37587-37596. 22 pages.

Non-Final Office Action for U.S. Appl. No. 16/656,417, filed Oct. 17, 2019 on behalf of California Institute of Technology Mail Date: Mar. 23, 2021. 20 pages.

Non-Final Office Action for U.S. Appl. No. 17/334,953, filed May 31, 2021 on behalf of California Institute of Technology. Mailed on Oct. 19, 2023. 20 pages.

Non-Final Office Action issued for U.S. Appl. No. 17/006,591, filed Aug. 28, 2020, on behalf of California Institute of Technology. Mail Date: Apr. 14, 2023. 39 Pages.

Notice of Allowability for U.S. Appl. No. 16/656,417, filed Oct. 17, 2019, on behalf of California Institute of Technology. Mail Date: Sep. 29, 2022. 4 Pages.

Notice of Allowability for U.S. Appl. No. 16/736,581, filed Jan. 7, 2020 on behalf of California Institute of Technology Mail Date: Jul. 19, 2023. 8 pages.

Notice of Allowance for U.S. Appl. No. 15/613,104, filed Jun. 2, 2017 on behalf of California Institute of Technology Mail Date: Jul. 18, 2019. 15 pages.

Notice of Allowance for U.S. Appl. No. 16/656,417, filed Oct. 17, 2019, on behalf of California Institute of Technology. Mail Date: Dec. 8, 2021. 7 Pages.

Notice of Allowance for U.S. Appl. No. 16/656,417, filed Oct. 17, 2019 on behalf of California Institute of Technology Mail Date: Jun. 27, 2022. 9 pages.

Notice of Allowance for U.S. Appl. No. 16/656,417, filed Oct. 17, 2019, on behalf of California Institute of Technology. Mail Date: Mar. 31, 2022. 19 Pages.

Notice of Allowance for U.S. Appl. No. 16/656,417, filed Oct. 17, 2019, on behalf of California Institute of Technology. Mail Date: Sep. 3, 2021. 9 Pages.

Notice of Allowance for U.S. Appl. No. 16/736,581, filed Jan. 7, 2020 on behalf of California Institute of Technology. Mail Date: Jan. 23, 2023. 14 pages.

Notice of Allowance for U.S. Appl. No. 16/736,581, filed Jan. 7, 2020 on behalf of California Institute of Technology Mail Date: Jun. 16, 2023. 11 pages.

Notice of Allowance for U.S. Appl. No. 17/816,373, filed Jul. 29, 2022 on behalf of California Institute of Technology, mailed on Jun. 8, 2023. 13 pages.

Notice of Allowance issued for U.S. Appl. No. 16/736,683, filed Jan. 7, 2020, on behalf of California Institute of Technology. Mail Date: Jan. 6, 2023. 11 Pages.

Notice of Allowance issued for U.S. Appl. No. 16/736,683, filed Jan. 7, 2020, on behalf of California Institute of Technology. Mail Date: May 31, 2023. 11 Pages.

Notice of Allowance issued for U.S. Appl. No. 17/816,373, filed Jul. 29, 2022 on behalf of California Institute of Technology. Mail Date: Dec. 4, 2023. 10 pages.

Perona, J. et al. "Structural basis of substrate specificity in the serine proteases", Protein Science, (1995), 4, 337-360. Cambridge University Press.

Supplemental Notice of Allowability for U.S. Appl. No. 16/736,581, filed Jan. 7, 2020 on behalf of California Institute of Technology Mail Date: Feb. 13, 2023. 3 pages.

The PubChem database entry for "Cyanogen Bromide", (downloaded Nov. 2, 2023). 89 pages.

"Thrombin" from Wikipedia, the online encyclopedia, downloaded from the Wayback Machine for Mar. 23, 2018. 24 pages.

To, Tsz-Leung et al; "Rationally designed fluorogenic protease reporter visualizes spatiotemporal dynamics of apoptosis in vivo." PNAS (Mar. 2015) 112(11), p. 3338-3343.

Waldner, B.J. et al. "Electrostatic recognition in substrate binding to serine proteases", Journal of Molecular Recognition 31, e2727.10 (2018), 12 pages. Website: doi.org/10/1002/jmr.2727.

Anderson, Caleb F. et al, "Protease sensitive nanomaterials for cancer therapeutics and imaging." Ind. Eng. Chem. Res. (Apr. 24, 2017) 56, p. 5761-5777. 17 pages.

(56) References Cited

OTHER PUBLICATIONS

Certification Statement and List—37 CFR 1.98(d)(1) filed in U.S. Appl. No. 18/046,881, filed Oct. 14, 2022 on behalf of California Institute of Technology. Oct. 14, 2024, 1 page.

Corrected Notice of Allowability for U.S. Appl. No. 17/334,953, filed May 31, 2021 on behalf of California Institute of Technology. Mailed on Dec. 4, 2024. 6 pages.

Dos Santos, Nancy, et al, "Influence of poly(ethylene glycol) grafting density and polymer length on liposomes: relating plasma circulation lifetimes to protein binding." Biochim. Biophys. Acta (2007) 1768, p. 1367-1377. 11 pages.

Dutka, P. et al., Supplemental Information—Structure of Anabaena flos-aquae gas vesicles revealed by cryo-ET. Structure, 31, 20 pages. May 4, 2023.

"Enzyme" Definition, Mechanisms, and Nomenclature, from Encyclopaedia Britannica (Britannica.com). 3 pages. Downloaded through the Wayback Machine for Jun. 29, 2019.

Final Office Action issued for U.S. Appl. No. 17/006,591, filed Aug. 28, 2020, on behalf of California Institute of Technology. Mail Date: Jul. 18, 2024. 24 Pages.

Green, Anthony et al, "In vitro testing of a protease sensitive contrast agent for optoacoustic imaging." J. Biomed. Optics (Mar./Apr. 2010) 15(2) 021315. 8 pages.

Law, Benedict et al., "Protease sensitive fluorescent nanofibers." Bioconj. Chem. (2007) 18, p. 1701-1704.

Non-Final Office Action for U.S. Appl. No. 18/317,915, filed May 15, 2023 on behalf of California Institute of Technology. Mailed on Jun. 10, 2024. 17 pages.

Notice of Allowability issued for U.S. Appl. No. 17/816,373, filed Jul. 29, 2022 on behalf of California Institute of Technology. Mail Date: Jun. 25, 2024. 5 pages.

Notice of Allowability issued for U.S. Appl. No. 17/816,373, filed Jul. 29, 2022 on behalf of California Institute of Technology. Mail Date: Sep. 13, 2024. 5 pages.

Notice of Allowance for U.S. Appl. No. 17/334,953, filed May 31, 2021 on behalf of California Institute of Technology. Mailed on Sep. 27, 2024. 9 pages.

Notice of Allowance for U.S. Appl. No. 18/317,915, filed May 15, 2023 on behalf of California Institute of Technology. Mailed on Oct. 22, 2024. 12 pages.

Notice of Allowance issued for U.S. Appl. No. 17/816,373, filed Jul. 29, 2022 on behalf of California Institute of Technology. Mail Date: Jun. 4, 2024. 11 pages.

Sciencelearn web page on enzymes in laundry detergent: website web.archive.org/web/20170521005639/https://www.sciencelearn.org.nz/resources/1947-enzymes-in-washing-powders. According to USPTO in U.S. Appl. No. 17/006,591, available at least by 2017. 4 pages.

Tang, Haichao et al, "The analysis of key factors related to ADSs structural design." Front. Pharmacol. (Apr. 2019) 10:373. 11 pages.

* cited by examiner

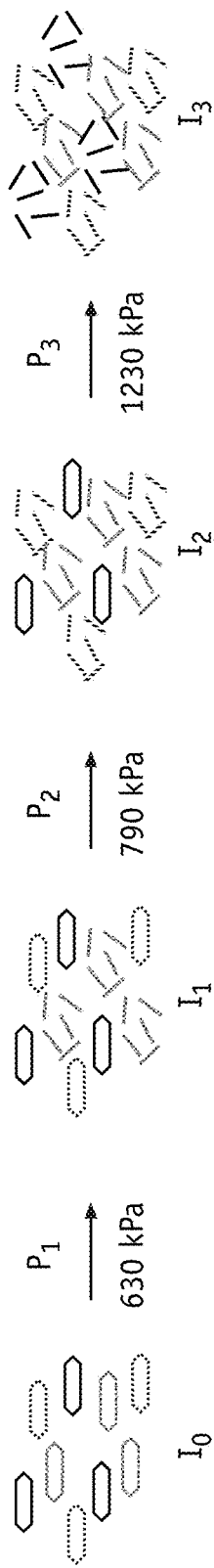
FIG. 4E
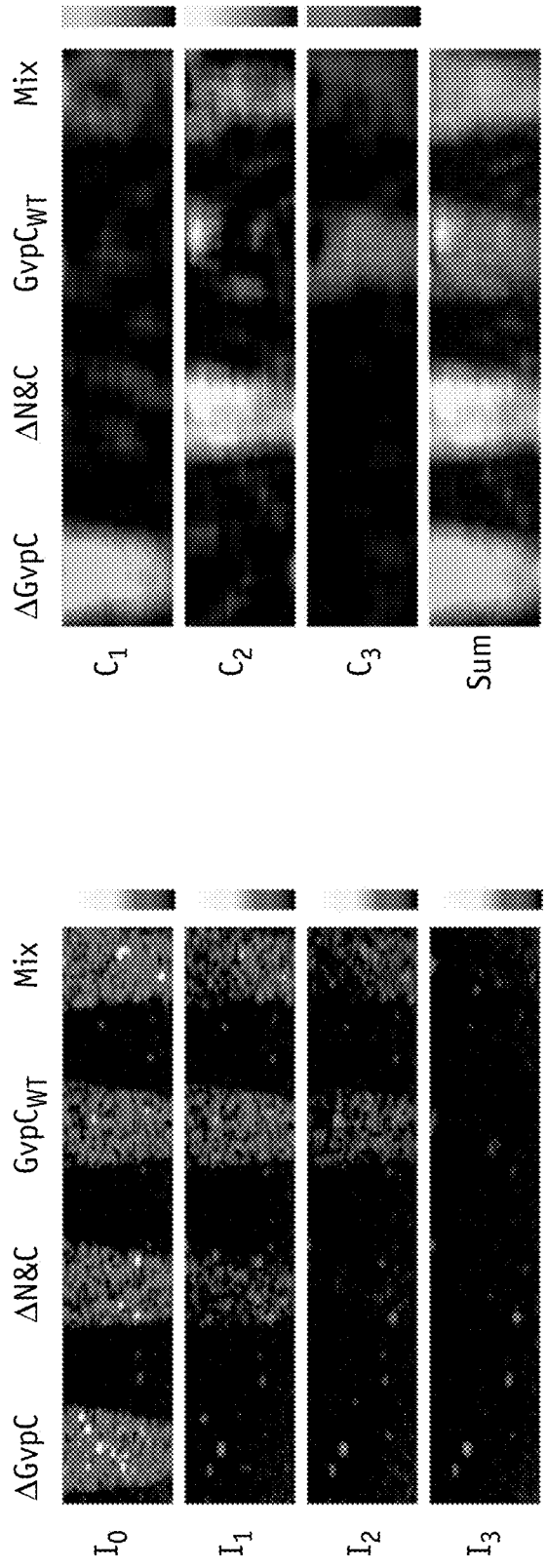
FIG. 4G
FIG. 4F

| Molar ratio of GvpC : GvpA (x/25) | Midpoint of Collapse (Pc) (kPa) | P_c (SEM) (kPa) | ΔP (kPa) | ΔP (SEM) (kPa) | Adj. R-Square |
|---|---|---|---|---|---|
| 0 | 193.77 | 0.31 | 16.72 | 0.27 | 0.999 |
| 0.05 | 219.29 | 0.46 | 20.44 | 0.40 | 0.999 |
| 0.1 | 229.47 | 0.62 | 21.9 | 0.55 | 0.999 |
| 0.25 | 249.28 | 0.99 | 28.07 | 0.88 | 0.998 |
| 0.5 | 266.01 | 1.13 | 30.94 | 0.99 | 0.998 |
| 1 | 285.85 | 1.19 | 33.95 | 1.05 | 0.998 |
| 2 | 299.66 | 1.53 | 40.31 | 1.35 | 0.997 |
| 10 | 314.99 | 2.01 | 50.84 | 1.77 | 0.996 |
| 25 | 330.11 | 1.88 | 50.75 | 1.65 | 0.997 |

| Molar ratio of GvpC : GvpA (x/25) | Midpoint of Collapse (Pc) (kPa) | Pc (SEM) (kPa) | ΔP (kPa) | ΔP (SEM) (kPa) | Adj. R-Square |
|---|---|---|---|---|---|
| 0 | 195.95 | 0.21 | 16.23 | 0.18 | 0.999 |
| 0.05 | 193.48 | 0.43 | 17.54 | 0.38 | 0.999 |
| 0.1 | 198.12 | 0.91 | 19.90 | 0.80 | 0.998 |
| 0.25 | 248.68 | 1.24 | 33.60 | 1.09 | 0.998 |
| 0.5 | 403.93 | 2.24 | 61.03 | 1.98 | 0.996 |
| 1 | 479.01 | 5.50 | 108.11 | 4.88 | 0.985 |
| 2 | 565.15 | 3.92 | 79.10 | 3.46 | 0.990 |
| 10 | 537.95 | 4.24 | 86.97 | 3.74 | 0.989 |
| 25 | 574.72 | 2.29 | 62.93 | 2.03 | 0.996 |

$$\underbrace{\begin{bmatrix} 6.26 \\ 3.98 \\ 4.82 \end{bmatrix}}_{\Delta} = \underbrace{\begin{bmatrix} 0.955 & 0.429 & 0.036 \\ 0.033 & 0.385 & 0.318 \\ 0.012 & 0.176 & 0.646 \end{bmatrix}}_{\alpha} \underbrace{\begin{bmatrix} 4.15 \\ 4.83 \\ 6.07 \end{bmatrix}}_{C} \qquad C = \alpha^{-1}\Delta$$

FIG. 7

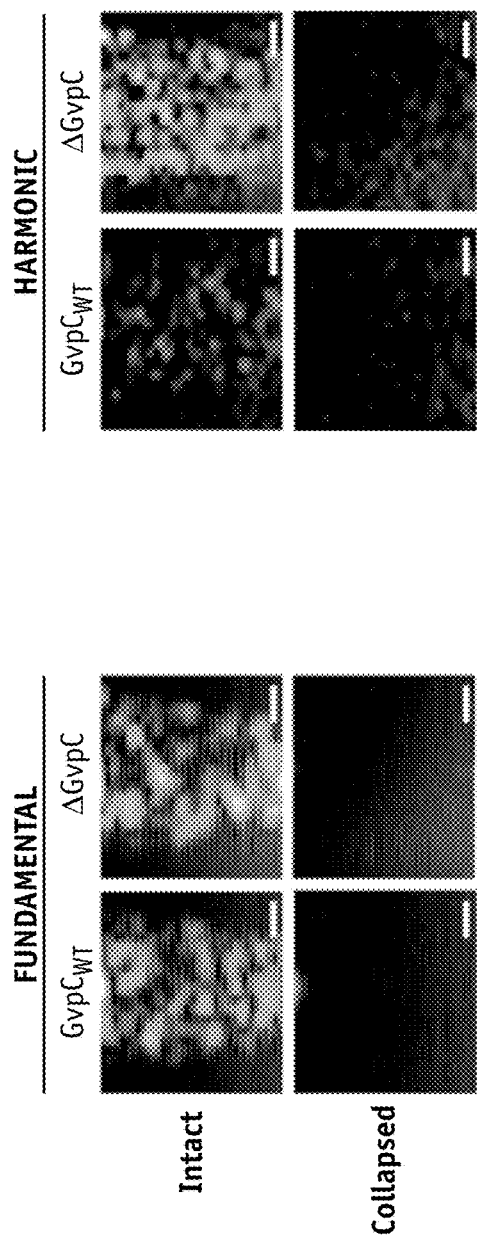
FIG. 8B
FIG. 8C
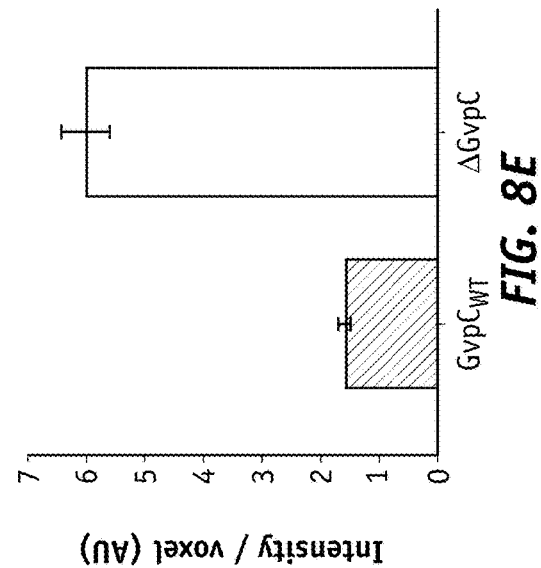
FIG. 8D
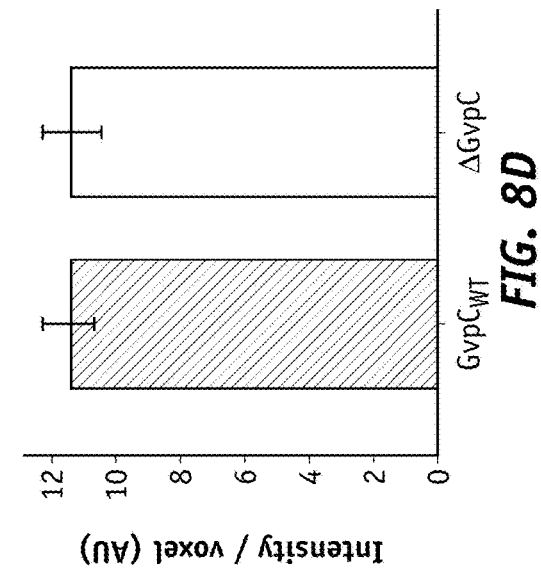
FIG. 8E

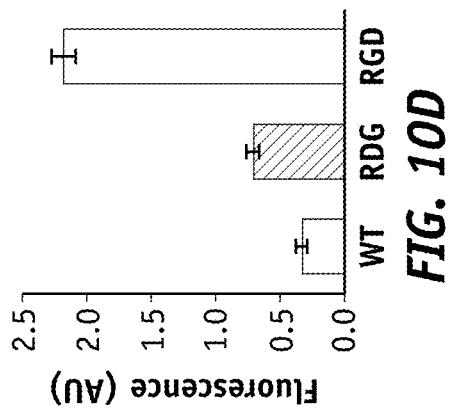
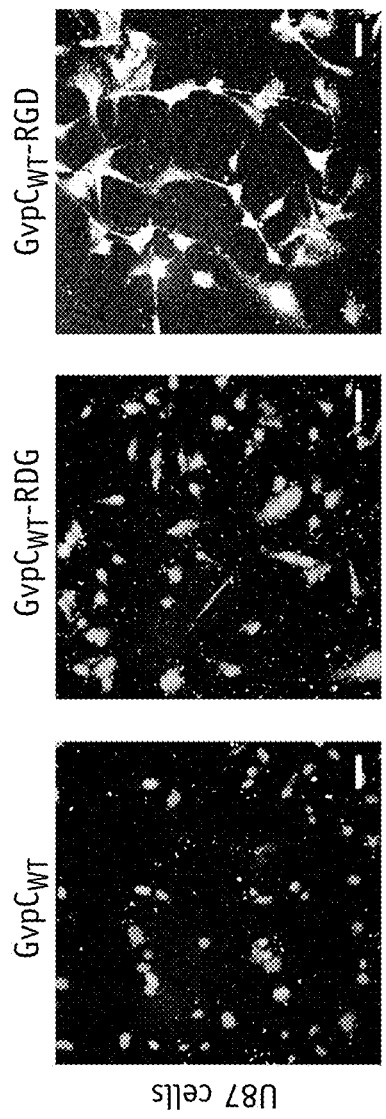
*FIG. 10C*
*FIG. 10D*
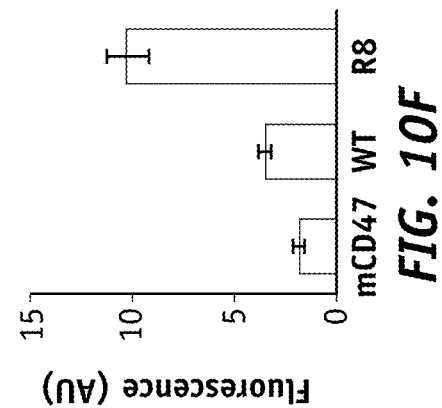
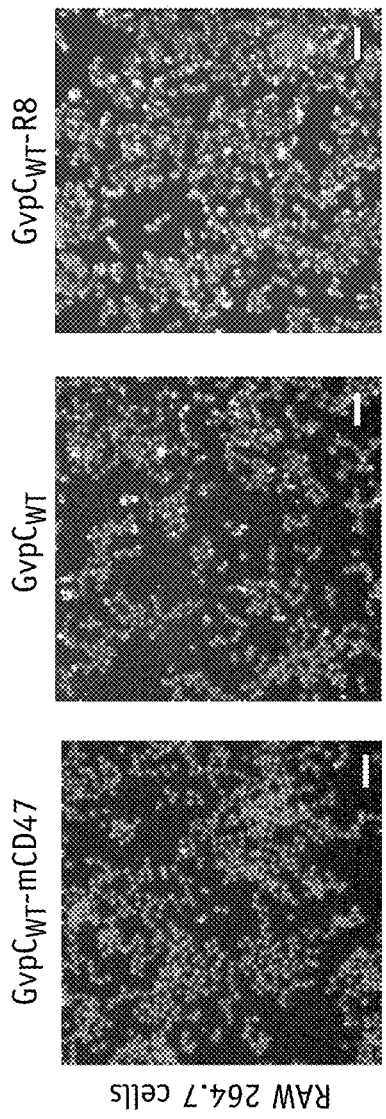
*FIG. 10E*
*FIG. 10F*

```
ΔN&C-CERY1         MGHHHHHHSG---------------------VAELSLETREFLSVTTAKRQEQAEKQAQELQAF
ΔNterm             MG-----------------------------VAELSLETREFLSVTTAKRQEQAEKQAQELQAF
N-rep3-C           M---------ISLMAKIRQEHQSIAEK--------------------------------------
SR3CERY1           MGHHHHHHSGISLMAKIRQEHQSIAEK--------------------------------------
WTCERY1            MGHHHHHHSGISLMAKIRQEHQSIAEKVAELSLETREFLSVTTAKRQEQAEKQAQELQAF
N-rep1-C           MG--------ISLMAKIRQEHQSIAEKVAELSLETREFLSVTTAKRQEQAEKQAQELQAF
SR1CERY1           MGHHHHHHSGISLMAKIRQEHQSIAEKVAELSLETREFLSVTTAKRQEQAEKQAQELQAF
ΔN&C               MG-----------------------------VAELSLETREFLSVTTAKRQEQAEKQAQELQAF
N-rep2endto3mid-C  M---------ISLMAKIRQEHQSIAEK--------------------------------------
N-His-GvpC         MGHHHHHHSGISLMAKIRQEHQSIAEKVAELSLETREFLSVTTAKRQEQAEKQAQELQAF
ΔCterm             MG--------ISLMAKIRQEHQSIAEKVAELSLETREFLSVTTAKRQEQAEKQAQELQAF
GvpCWT-ACPP        MGHHHHHHSGISLMAKIRQEHQSIAEKVAELSLETREFLSVTTAKRQEQAEKQAQELQAF
GvpCWT-hPRM        MGHHHHHHSGISLMAKIRQEHQSIAEKVAELSLETREFLSVTTAKRQEQAEKQAQELQAF
GvpCWT-LRP         MGHHHHHHSGISLMAKIRQEHQSIAEKVAELSLETREFLSVTTAKRQEQAEKQAQELQAF
GvpCWT-mCD47       MGHHHHHHSGISLMAKIRQEHQSIAEKVAELSLETREFLSVTTAKRQEQAEKQAQELQAF
GvpCWT-R8          MGHHHHHHSGISLMAKIRQEHQSIAEKVAELSLETREFLSVTTAKRQEQAEKQAQELQAF
GvpCWT-RGD         MGHHHHHHSGISLMAKIRQEHQSIAEKVAELSLETREFLSVTTAKRQEQAEKQAQELQAF
GvpCWT-RDG         MGHHHHHHSGISLMAKIRQEHQSIAEKVAELSLETREFLSVTTAKRQEQAEKQAQELQAF
GvpCWT             MG--------ISLMAKIRQEHQSIAEKVAELSLETREFLSVTTAKRQEQAEKQAQELQAF
GvpC-SpyTag        MG--------ISLMAKIRQEHQSIAEKVAELSLETREFLSVTTAKRQEQAEKQAQELQAF
N-rep1to3-C        MG--------ISLMAKIRQEHQSIAEKVAELSLETREFLSVTTAKRQEQAEKQAQELQAF
N-rep1to2-C        MG--------ISLMAKIRQEHQSIAEKVAELSLETREFLSVTTAKRQEQAEKQAQELQAF
N-rep1to4-C        MG--------ISLMAKIRQEHQSIAEKVAELSLETREFLSVTTAKRQEQAEKQAQELQAF ΔN&C-CERY1         YKDLQETSQQFLSETAQARIAQAEKQAQELLAFHKELQETSQQFLSATAQARIAQAEKQA
ΔNterm             YKDLQETSQQFLSETAQARIAQAEKQAQELLAFHKELQETSQQFLSATAQARIAQAEKQA
N-rep3-C           -----------------------------HKELQETSQQFLSATAQARIAQAEKQA
SR3CERY1           -----------------------------HKELQETSQQFLSATAQARIAQAEKQA
WTCERY1            YKDLQETSQQFLSETAQARIAQAEKQAQELLAFHKELQETSQQFLSATAQARIAQAEKQA
N-rep1-C           ------------------------------------------------------------
SR1CERY1           ------------------------------------------------------------
ΔN&C               YKDLQETSQQFLSETAQARIAQAEKQAQELLAFHKELQETSQQFLSATAQARIAQAEKQA
N-rep2endto3mid-C  --------------QAQELLAFHKELQETSQQFLSATAQAR-------------------
N-His-GvpC         YKDLQETSQQFLSETAQARIAQAEKQAQELLAFHKELQETSQQFLSATAQARIAQAEKQA
ΔCterm             YKDLQETSQQFLSETAQARIAQAEKQAQELLAFHKELQETSQQFLSATAQARIAQAEKQA
GvpCWT-ACPP        YKDLQETSQQFLSETAQARIAQAEKQAQELLAFHKELQETSQQFLSATAQARIAQAEKQA
GvpCWT-hPRM        YKDLQETSQQFLSETAQARIAQAEKQAQELLAFHKELQETSQQFLSATAQARIAQAEKQA
GvpCWT-LRP         YKDLQETSQQFLSETAQARIAQAEKQAQELLAFHKELQETSQQFLSATAQARIAQAEKQA
GvpCWT-mCD47       YKDLQETSQQFLSETAQARIAQAEKQAQELLAFHKELQETSQQFLSATAQARIAQAEKQA
GvpCWT-R8          YKDLQETSQQFLSETAQARIAQAEKQAQELLAFHKELQETSQQFLSATAQARIAQAEKQA
GvpCWT-RGD         YKDLQETSQQFLSETAQARIAQAEKQAQELLAFHKELQETSQQFLSATAQARIAQAEKQA
GvpCWT-RDG         YKDLQETSQQFLSETAQARIAQAEKQAQELLAFHKELQETSQQFLSATAQARIAQAEKQA
GvpCWT             YKDLQETSQQFLSETAQARIAQAEKQAQELLAFHKELQETSQQFLSATAQARIAQAEKQA
GvpC-SpyTag        YKDLQETSQQFLSETAQARIAQAEKQAQELLAFHKELQETSQQFLSATAQARIAQAEKQA
N-rep1to3-C        YKDLQETSQQFLSETAQARIAQAEKQAQELLAFHKELQETSQQFLSATAQARIAQAEKQA
N-rep1to2-C        YKDLQETSQQFLSETAQARIAQAEKQAQELLAF----------------------------
N-rep1to4-C        YKDLQETSQQFLSETAQARIAQAEKQAQELLAFHKELQETSQQFLSATAQARIAQAEKQA
```

FIG. 11A

```
ΔN&C-CERY1          QELLAFYQEVRETSQQFLSATAQARIAQAEKQAQELLAFHKELQETSQQFLSATADARTA
ΔNterm              QELLAFYQEVRETSQQFLSATAQARIAQAEKQAQELLAFHKELQETSQQFLSATADARTA
N-rep3-C            QELLAF------------------------------------------------------
SR3CERY1            QELLAF------------------------------------------------------
WTCERY1             QELLAFYQEVRETSQQFLSATAQARIAQAEKQAQELLAFHKELQETSQQFLSATADARTA
N-rep1-C            ------------------------------------------------------------
SR1CERY1            ------------------------------------------------------------
ΔN&C                QELLAFYQEVRETSQQFLSATAQARIAQAEKQAQELLAFHKELQETSQQFLSATADARTA
N-rep2endto3mid-C   ------------------------------------------------------------
N-His-GvpC          QELLAFYQEVRETSQQFLSATAQARIAQAEKQAQELLAFHKELQETSQQFLSATADARTA
ΔCterm              QELLAFYQEVRETSQQFLSATAQARIAQAEKQAQELLAFHKELQETSQQFLSATADARTA
GvpCWT-ACPP         QELLAFYQEVRETSQQFLSATAQARIAQAEKQAQELLAFHKELQETSQQFLSATADARTA
GvpCWT-hPRM         QELLAFYQEVRETSQQFLSATAQARIAQAEKQAQELLAFHKELQETSQQFLSATADARTA
GvpCWT-LRP          QELLAFYQEVRETSQQFLSATAQARIAQAEKQAQELLAFHKELQETSQQFLSATADARTA
GvpCWT-mCD47        QELLAFYQEVRETSQQFLSATAQARIAQAEKQAQELLAFHKELQETSQQFLSATADARTA
GvpCWT-R8           QELLAFYQEVRETSQQFLSATAQARIAQAEKQAQELLAFHKELQETSQQFLSATADARTA
GvpCWT-RGD          QELLAFYQEVRETSQQFLSATAQARIAQAEKQAQELLAFHKELQETSQQFLSATADARTA
GvpCWT-RDG          QELLAFYQEVRETSQQFLSATAQARIAQAEKQAQELLAFHKELQETSQQFLSATADARTA
GvpCWT              QELLAFYQEVRETSQQFLSATAQARIAQAEKQAQELLAFHKELQETSQQFLSATADARTA
GvpC-SpyTag         QELLAFYQEVRETSQQFLSATAQARIAQAEKQAQELLAFHKELQETSQQFLSATADARTA
N-rep1to3-C         QELLAF------------------------------------------------------
N-rep1to2-C         ------------------------------------------------------------
N-rep1to4-C         QELLAFYQEVRETSQQFLSATAQARIAQAEKQAQELLAF---------------------

ΔN&C-CERY1          QAKEQKESLLKFGSGWMVLPWLPGTLD---------------------------------
ΔNterm              QAKEQKESLLKFRQDLFVSIFGSLEHHHHHH-----------------------------
N-rep3-C            -----------RQDLFVSIFGSLEHHHHHH-----------------------------
SR3CERY1            -----------RQDLFVSIFGSGWMVLPWLPGTLD-------------------------
WTCERY1             QAKEQKESLLKFRQDLFVSIFGSGWMVLPWLPGTLD------------------------
N-rep1-C            -----------RQDLFVSIFGSLEHHHHHH-----------------------------
SR1CERY1            -----------RQDLFVSIFGSGWMVLPWLPGTLD-------------------------
ΔN&C                QAKEQKESLLKFSLEHHHHHH---------------------------------------
N-rep2endto3mid-C   -----------RQDLFVSIFGSLEHHHHHH-----------------------------
N-His-GvpC          QAKEQKESLLKFRQDLFVSIFG--------------------------------------
ΔCterm              QAKEQKESLLKFHHHHHH------------------------------------------
GvpCWT-ACPP         QAKEQKESLLKFRQDLFVSIFCEQRRRRRRRRGGGPLGLAGEEEEEEEE
GvpCWT-hPRM         QAKEQKESLLKFRQDLFVSIFGARYCCRSQSRSRYYRQRQRSRRRRRSCQTRRRAMRC
GvpCWT-LRP          QAKEQKESLLKFRQDLFVSIFGSGKKKKKKKKKKKKKKKKKKKKKKKKKKKKKKKKKKKK
GvpCWT-mCD47        QAKEQKESLLKFRQDLFVSIFGSGGNYTCEVTELTREGETIIELK---------------
GvpCWT-R8           QAKEQKESLLKFRQDLFVSIFGSGRRRRRRRR----------------------------
GvpCWT-RGD          QAKEQKESLLKFRQDLFVSIFGSGCDCRGDCFC---------------------------
GvpCWT-RDG          QAKEQKESLLKFRQDLFVSIFGSGCDCRDGCFC---------------------------
GvpCWT              QAKEQKESLLKFRQDLFVSIFGSLEHHHHHH-----------------------------
GvpC-SpyTag         QAKEQKESLLKFRQDLFVSIFGSGAHIVMVDAYKPTKGSGLEHHHHHH------------
N-rep1to3-C         -----------RQDLFVSIFGSLEHHHHHH-----------------------------
N-rep1to2-C         -----------RQDLFVSIFGSLEHHHHHH-----------------------------
N-rep1to4-C         -----------RQDLFVSIFGSLEHHHHHH-----------------------------
```

FIG. 11B

```
ΔN&C-CERY1           ------------------------------------------------------------
ΔNterm               ------------------------------------------------------------
N-rep3-C             ------------------------------------------------------------
SR3CERY1             ------------------------------------------------------------
WTCERY1              ------------------------------------------------------------
N-rep1-C             ------------------------------------------------------------
SR1CERY1             ------------------------------------------------------------
ΔN&C                 ------------------------------------------------------------
N-rep2endto3mid-C    ------------------------------------------------------------
N-His-GvpC           ------------------------------------------------------------
ΔCterm               ------------------------------------------------------------
GvpCWT-ACPP          ------------------------------------------------------------
GvpCWT-hPRM          CRPRYRPRCRRHTGTRTRPL----------------------------------------
GvpCWT-LRP           KKKKKKKKKKKKKKKKKKKKKKKKKKKKKKKKKKKKKKKKKKKKKKKKKKKKKKKKKKKK
GvpCWT-mCD47         ------------------------------------------------------------
GvpCWT-R8            ------------------------------------------------------------
GvpCWT-RGD           ------------------------------------------------------------
GvpCWT-RDG           ------------------------------------------------------------
GvpCWT               ------------------------------------------------------------
GvpC-SpyTag          ------------------------------------------------------------
N-rep1to3-C          ------------------------------------------------------------
N-rep1to2-C          ------------------------------------------------------------
N-rep1to4-C          ------------------------------------------------------------

ΔN&C-CERY1           -----
ΔNterm               -----
N-rep3-C             -----
SR3CERY1             -----
WTCERY1              -----
N-rep1-C             -----
SR1CERY1             -----
ΔN&C                 -----
N-rep2endto3mid-C    -----
N-His-GvpC           -----
ΔCterm               -----
GvpCWT-ACPP          -----
GvpCWT-hPRM          -----
GvpCWT-LRP           KKKK
GvpCWT-mCD47         -----
GvpCWT-R8            -----
GvpCWT-RGD           -----
GvpCWT-RDG           -----
GvpCWT               -----
GvpC-SpyTag          -----
N-rep1to3-C          -----
N-rep1to2-C          -----
N-rep1to4-C          -----
```

FIG. 11C

| Lane | Sample |
|---|---|
| 1 | Ladder |
| 2 | ST-GvpC (100 ng) |
| 3 | ST-GvpC (200 ng) |
| 4 | ST-GvpC (400 ng) |
| 5 | ST-GvpC (500 ng) |
| 6 | ST-GvpC (600 ng) |
| 7 | ST-GvpC (800 ng) |
| 8 | ST-GvpC (1000 ng) |
| 9 | ΔGvpC |
| 10 | ST-Ana GVs |

N-term    MSVTDKRDEMSTARDKFAESQ
Rep 1     QEFESYADEFAADITAKQDDVSDLVDAITDFQAEMTNTT
Rep 2     DAFHTYGDEFAAEVDHLRADIDAQRDVIREMQ
Rep 3     DAFEAYADIFATDIADKQDIGNLLAAIEALRTEMNSTH
Rep 4     GAFEAYADDFAADVAALRDISDLVAAIDDFQEEFIAVQ
Rep 5     DAFDNYAGDFDAEIDQLHAAIADQHDSFDATA
Rep 6     DAFAEYRDEFYRIEVEALLEAINDFQQDIGDFRAEFETTE
Rep 7     DAFVAFARDFYGHEITAEEGAAEAEAEPVEADADVEAEAEAEVSPD
C-term    EAGGESAGTEEEETEPAEVETAAPEVEGSPADTADEAEDTEAEEETEEEAPEDMVQCRVC
C-term (cont.) GEYYQAITEPHLQTHDMTIQEYRDEYGEDVPLRPDDKT

FIG. 16A

N-term    MISLMAKIRQEHQSIAEK
Rep 1     VAELSLETREFLSVTTAKRQEQAEKQAQELQAF
Rep 2     YKDLQETSQQFLSETAQARIAQAEKQAQELLAF
Rep 3     HKELQETSQQFLSATAQARIAQAEKQAQELLAF
Rep 4     YQEVRETSQQFLSATAQARIAQAEKQAQELLAF
Rep 5     HKELQETSQQFLSATADARTAQAKEQKESLLKF
C-term    RQDLFVSIFG

FIG. 16B

```
N-term       MSVKDKREKMTATREEFAEVQ
Rep 1        QAFAAYADEFAADVDDKRDVSELVDGIDTLRTEMNSTN
Rep 2        DAFRAYSEEFAADVEHFHTSVADRR
Rep 3        DAFDAYADIFATDVAEMQDVSDLLAAIDDLRAEMDETH
Rep 4        EAFDAYADAFVTDVATLRDVSDLLTAISELQSEFVSVQ
Rep 5        GEFNGYASEFGADIDQFHAVVAEKRDGHKDVA
Rep 6        DAFLQYREEFHGVEVQSLLDNIAAFQREMGDYRKAFETTE
Rep 7        EAFASFARDFYGQAAPMATPLNNAAETAVTGTETEVDIPPI
C-term       EDSVEPDGEDEDSKADDVEAEAEVETVEMEFGAEMDTEADEDVQSESVREDD
C-term (cont.) QFLDDETPEDMVQCLVCGEYYQAITEPHLQTHDMTIKKYREEYGEDVPLRPDDKA
```

FIG. 16C

```
N-term       MTPLMIRIRQEHRGIAEE
Rep 1        VTQLFKDTQEFLSVTTAQRQAQAKEQAENLHQF
Rep 2        HKDLEKDTEEFLTDTAKERMAKAKQQAEDLFQF
Rep 3        HKEMAENTQEFLSETAKERMAQAQEQARQLREF
Rep 4        HQNLEQTTNEFLADTAKERMAQAQEQKQQLHQF
C-term       RQDLFASIFGTF
```

FIG. 16D

```
N-term       MTALMVRIRQEHRSIAEE
Rep 1        VTQLFRETHEFLSATTAHRQEQAKQQAQQLHQF
Rep 2        HQNLEQTTHEFLTETTQRVAQAEAQANFLHKF
Rep 3        HQNLEQTTQEFLAETAKNRTEQAKAQSQYLQQF
C-term       RKDLFASIFGTF
```

FIG. 16E

| No. | Construct | Hydrostatic collapse (kPa) (±10%) | Concentration | Binding assay | His-Tag |
|---|---|---|---|---|---|
| 1 | ΔGvpC | 195 | | yes | C-term |
| 2 | ΔN&C (ΔN&C-GvpC) | 374 | 2x/25 | yes | C-term |
| 3 | ΔN&C | 323 | equimolar GvpC:GvpA | | C-term |
| 4 | GvpC$_{WT}$ (WT-GvpC) | 582 | 2x/25 | yes | C-term |
| 5 | N-His GvpC | 602 | 2x/25 | yes | N-term |
| 6 | N-rep1-C (SR1, GvpCRep1) | 257 | 5x/25 | yes | C-term |
| 7 | N-rep1-C (SR1, GvpCRep1) | 450 | 7.5x/25 | | C-term |
| 8 | N-rep1-C (SR1, GvpCRep1) | 206 | 1x/25 | | C-term |
| 9 | N-rep1-C (SR1, GvpCRep1) | 295 | 2x/25 | | C-term |
| 10 | N-rep1-C (SR1, GvpCRep1) | 469 | 4x/25 | | C-term |
| 11 | N-rep1-C (SR1, GvpCRep1) | 474 | 8x/25 | | C-term |
| 12 | N-rep1-C (SR1, GvpCRep1) | 465 | 16x/25 | | C-term |
| 13 | N-rep1-C (SR1, GvpCRep1) | 322 | 2x/25 | | C-term |
| 14 | N-rep3-C (SR3, GvpCRep3) | 195 | 7.5x/25 | yes | C-term |
| 15 | N-rep2to3-C (GvpCRep2to3) | 210 | 7.5x/25 | yes | C-term |
| 16 | ΔN-term (ΔN) | 315 | equimolar GvpC:GvpA | | C-term |
| 17 | ΔC-term (ΔC) | 383 | equimolar GvpC:GvpA | | C-term |
| 18 | N-rep1to4-C (GvpCΔ1) | 468 | 2x/25 | | C-term |
| 19 | N-rep1to3-C (GvpCΔ2) | 500 | 2x/25 | | C-term |
| 20 | N-rep1to2-C (GvpCΔ3) | 459 | 2x/25 | | C-term |
| 21 | N-rep1-C (SR1, GvpCΔ4) | 316 | 2x/25 | | C-term |
| 22 | GvpC-RGD | 520 | 2x/25 | | N-term |
| 23 | GvpC-RDG | 500 | 2x/25 | | N-term |
| 24 | GvpC-R8 | 540 | 2x/25 | | N-term |
| 25 | GvpC-ACPP | 490 | 2x/25 | | N-term |
| 26 | GvpC-LRP | 440 | 10x/25 | | N-term |
| 27 | GvpC-hPRM | 480 | 10x/25 | | N-term |
| 28 | GvpC-mCD47 | 410 | 2x/25 | | N-term |
| 29 | SR1CERY1 | 194 | 7.5x/25 | yes | N-term |
| 30 | SR3CERY1 | 193 | 7.5x/25 | yes | N-term |
| 31 | ΔN&C-CERY1 | 302 | 2x/25 | yes | N-term |
| 32 | WTCERY1 | 462 | 2x/25 | yes | N-term |
| 33 | ST-GvpC + SC-mNG | 565 | 2x/25 | yes | C-term |
| 34 | ST-GvpC (GvpC-Spytag, ST-GV, ST-Ana GV) | 577 | 2x/25 | yes | C-term |

FIG. 17

WT Ana GvpC

```
                         MISLMAKIRQEHQSIAEK  Repeat
VAELSLETREFLSVTTAKRQEQAEKQAQELQAF    1
YKDLQETSQQFLSETAQARIAQAEKQAQELLAF    2
HKELQETSQQFLSATAQARIAQAEKQAQELLAF    3
YQEVRETSQQFLSATAQARIAQAEKQAQELLAF    4
HKELQETSQQFLSATADARIAQAKEQKESLLKF    5
RQDLFVSIPG
```

FIG. 18

| Pressure at midpoint OD (kPa) | |
|---|---|
| ΔGvpC | 210 |
| GvpC$_{WT}$ | 582 |
| GvpCRep1-7.5x | 450 |
| GvpCRep3-7.5x | 195 |
| GvpCRep2to3-7.5x | 210 |

| Lane | Sample |
|---|---|
| 1 | Ladder |
| 2 | ΔGvpC |
| 3 | GvpC$_{WT}$ |
| 4 | GvpCRep1-7.5x/25 |
| 5 | GvpCRep1-5x/25 |
| 6 | GvpCRep2to3-7.5x/25 |
| 7 | GvpCRep3-7.5x/25 |

| Pressure at midpoint OD (kPa) | |
|---|---|
| ΔGvpC | 199 |
| $GV_{WT}$ | 582 |
| $GvpC_{WT}$ | 525 |
| ΔN | 315 |
| ΔC | 383 |
| ΔN&C | 323 |

| Microorganism | gvp genes | Most salient features of organisms | Gas vesicle shape and regulation |
|---|---|---|---|
| Haloarchaea | | | |
| Halobacterium salinarum str. PHH1 | p-vac, c-vac | Extremely halophilic archaea isolated from salted fish | • Spindle-shaped gas vesicles owing to expression of p-vac[40,56]<br>• Gas vesicle formation induced at low temperature (15°C) and reduced under anoxic conditions[13,15] |
| Halobacterium salinarum str. PHH4 | c-vac | Mutant of Hbt. salinarum str. PHH1 (REF. 98) | • Cylinder-shaped gas vesicles owing to expression of c-vac<br>• Gas vesicle formation induced at low temperature (15°C) and reduced under anoxic conditions[13,15] |
| Halobacterium salinarum str. NRC-1 | gvp1, gvp2 | Strain deposited in the American Type Culture Collection (Hbt. salinarum str. ATCC 700922) | • Spindle-shaped gas vesicles owing to expression of gvp1 (REF. 99)<br>• Gas vesicle formation induced at low temperature (15°C) and reduced under anoxic conditions[13,15] |
| Haloferax mediterranei | mc-vac | Moderately halophilic archaeon isolated from near Alicante, Spain | • Cylinder-shaped gas vesicles owing to expression of mc-vac[16]<br>• Gas vesicle formation induced at by high salinity (>17% weight per volume) and reduced under anoxic conditions[13,16] |
| Halorubrum vacuolatum | nv-vac | Haloalkaliphilic archaeon isolated from the alkaline Lake Magadi in Kenya[15] | • Cylinder-shaped gas vesicles owing to expression of nv-vac[17]<br>• Gas vesicle formation induced by high salinity (>20% weight per volume)[17] |
| Haloquadratum walsbyi | Undetermined* | Extremely halophilic archaeon isolated from salt brines in Sinai and Australia | • Cylinder-shaped gas vesicles[19,20] |
| Photosynthetic bacteria | | | |
| Anabaena flos-aquae | Undetermined* | Filament-forming cyanobacterium | • Cylinder-shaped gas vesicles<br>• Possible light-mediated regulation of gas vesicle formation‡ |
| Calothrix sp. PCC 7601 | Undetermined* | Filament-forming cyanobacterium | • Light-dependent regulation of gvpAC expression by antisense RNA against gvpA[89]<br>• Gas vesicles confined to hormogonia[42] |

FIG. 22A

| Species | | Description |
|---|---|---|
| Planktothrix rubescens | Undetermined* | Filament-forming cyanobacterium | • Cylinder-shaped gas vesicles[5]<br>• Possible light-mediated regulation of gas vesicle formation[‡] |
| Microcystis sp. BC 84/1 | Undetermined* | Unicellular cyanobacteria | • Cylinder-shaped gas vesicles[5]<br>• Possible light-mediated regulation of gas vesicle formation[‡] |
| Pelodictyon phaeoclathratiforme | Undetermined* | Anoxygenic green sulphur bacterium | • Cylinder-shaped gas vesicles[25]<br>• Gas vesicle formation occurs only at light intensities of <5 µm m$^{-2}$ s$^{-1}$ in stationary phase[25] |
| Heterotrophic bacteria | | | |
| Psychromonas ingrahamii | Undetermined* | Psychrophilic isolate from arctic sea ice[25] | • Shape undetermined[§] |
| Octadecabacter spp. | Undetermined* | Psychrophilic isolate from arctic or antarctic sea ice[25] | • Shape undetermined[§] |
| Desulforhopalus vacuolatus | Undetermined* | Psychrophilic sulphate reducer isolated from shallow sediments of Kysing Fjord, Denmark[31] | • Shape undetermined[§] |
| Ancylobacter aquaticus | Undetermined* | Mesophilic heterotroph[33] | • Cylinder-shaped gas vesicles |
| Serratia sp. ATCC 39006 | 16.6kb gene cluster | Mesophilic enterobacterium | • Nutritional stress and quorum sensing regulate gvp expression[40] |
| Sporohalobacter lortetii | Undetermined* | | • Gas vesicle formation during sporulation<br>• Gas vesicles remain attached to endospores |
| Desulfotomaculum acetoxidans | Undetermined* | | • Gas vesicles remain attached to endospores | gvp, gas vesicle protein. *Minimal region required for gas vesicle formation not yet determined; gvp genes can be dispersed in the genome. [‡]Ecological studies indicate that gas vesicle formation might be regulated by the light levels, but this has not yet been investigated at the molecular level of gene expression. [§]No electron microscopy images available, only phase contrast microscopy.

*FIG. 22B*

| Gene product | Approx mol mass (kDa) | No. of amino acids[b] in: | | | | Comments |
|---|---|---|---|---|---|---|
| | | H. halobium plasmid gene | H. salinarium plasmid gene | H. salinarium chromosomal gene | H. mediterranei chromosomal gene | |
| Strand 1 | | | | | | |
| GvpA | 8.1 | 75 | 75 | 78 | 77 | Principal component; forms ribs[c] |
| GvpC | 42.4 | 382 | 382 | 385 | 381 | Outer protein, stabilizes structure[c] |
| GvpN | 39.2 | 347 | 346 | 345 | 347 | Has a nucleotide binding site |
| GvpO | ND[d] | ? | 120 | 111 | 140 | |
| Strand 2 | | | | | | |
| GvpD | 59.3 | 536 | 536 | 492 | 545 | Has a nucleotide binding site, regulates expression[e] |
| GvpE | 21.0 | 191 | 191 | 192 | 192 | |
| GvpF | 24.0 | 213 | 214 | 217 | 213 | |
| GvpG | 10.0 | 83 | 83 | 83 | 83 | |
| GvpH | 19.9 | 182 | 182 | 163 | 216 | |
| GvpI | 16.3 | 144 | 140 | 114 | 162 | A basic protein |
| GvpJ | 12.0 | 114 | 114 | 98 | 114 | Partially homologous with GvpA and GvpM |
| GvpK | 12.7 | 113 | 113 | 119 | 117 | |
| GvpL | 32.0 | 281 | 281 | 273 | 322 | |
| GvpM | 9.2 | 84 | 84 | 73 | 86 | Partially homologous with GvpA and GvpJ |

[a] Data from Jones et al. (106) and Halladay et al. (80) for *H. halobium* and from Englert et al. (58) and Horne et al. (91) for *H. salinarium* and *H. mediterranei*.
[b] Including the N-terminal Met, except for GvpA.
[c] By analogy with the function demonstrated in cyanobacteria.
[d] ND, not determined.
[e] From Englert et al. (60).

FIG. 23

```
r7-halsa   DAFVAFARDFYGHEITAEEGAAEAEAEPVEADADVEAEAEVSPD    44
r6-halsa   DAFAEYRDEFYRIEVEALLEAINDFQQDIG---DFRAEFETTE-    40
r5-halsa   DAFDNYAGDFD-AEIDQLHAAIADQHDSFD---ATA--------    32
r2-halsa   DAFHTYGDEFA-AEVDHLRADIDAQRDVIR---EMQ--------    32
r3-halsa   DAFEAYADIFA-TDIADK-QDIGNLLAAIE---ALRTEMNSTH-    38
r1-halsa   QEFESYADEFA-ADITAKQDDVSDLVDAIT---DFQAEMTNTT-    39
r4-halsa   GEFEAYADDFA-ADVAAL-RDISDLVAAID---DFQEEFIAVQ-    38
             *  :  *    ::                   .
```

FIG. 26A

```
r7-halmed  EAFASFARDFYGQGAAPMATP---LNNAAETA--VTGTETEVDIPPI  42
r6-halmed  DAFLQYREEFHGVE------VQSLLDNIAAFQREMGDYRKAFETTE-  40
r1-halmed  QAFAAYADEFAADVDDKRDVS-ELVDGIDTLRTEMSTN--------   38
r3-halmed  DAFDAYADIFATDVAEMQDVS-DLLAAIDDLRAEMDETH--------  38
r4-halmed  EAFDAYADAFVTDVATLRDVS-DLLTAISELQSEFVSVQ--------  38
r2-halmed  DAFRAYSEEFAADVEHFHTSVADRR---------------------  25
r5-halmed  GEFNGYASEFGADIDQFHAVVAEKRDGHKDVA---------------  32
             *  :  *
```

FIG. 26B

```
r1-ana     VAELSLETREFLSVTTAKRQEQAEKQAQELQAF    33
r5-ana     HKELQETSQQFLSATADARTAQAKEQKESLLKF    33
r4-ana     YQEVRETSQQFLSATAQARIAQAEKQAQELLAF    33
r2-ana     YKDLQETSQQFLSETAQARIAQAEKQAQELLAF    33
r3-ana     HKELQETSQQFLSATAQARIAQAEKQAQELLAF    33
             ::    :::.***  *:  *  **:.*  :.*  *
```

FIG. 26C

```
r1-microchaete   VTQLFKDTQEFLSVTTAQRQAQAKEQAENLHQF    33
r3-microchaete   HKEmAENTQEFLSETAKERMAQAQEQARQLREF    33
r2-microchaete   HKDLEKDTEEFLTDTAKERMAKAKQQAEDLFQF    33
r4-microchaete   HQNLEQTTNEFLADTAKERMAQAQEQKQQLHQF    33
                   ::  :  *:***: *:  :*  *:*::*  .:*  :*
```

FIG. 26D

```
r1-Nostoc      VTQLFRETHEFLSATTAHPQEQAKQQAQQLHQF       33
r2-Nostoc      HQNLEQTTHEFLTETTTQRVAQAEAQANFLHKF       33
r3-Nostoc      HQNLEQTTQEFLAETAKNRTEQAKAQSQYLQQF       33
               :*  : *:***: *: :*  **: *:: *::*
```

FIG. 26E

```
r1-microcystis  VAKLSQEVQAFLSDVKTERQKQAQEQATAERQS---------------  33
r2-microcystis  FQKVQQESHLFLTATQKQRLAQAEKQKEDLRQF---------------  33
r6-microcystis  ---------------QERRLAEAKQLKDDLRQF---------------  18
r3-microcystis  ---------------QEQRLAAAKQLDNDLRQQRLDRAKQLKEDLSQF  33
r4-microcystis  ---------------QEQRLAEAKQLANDLRQQHLDRAKQLKEDLSQF  33
r5-microcystis  ---------------QEQRLAAAKQLEDELRQLHLDRAKQVKDDLSQF  33
                               : .*   *::    ***
```

FIG. 26F

```
Halmed-consensus   DAFAAYADEFAADVDDFHDVSADLLDGIDDLQAEMNSTNKAEETTE
Halsa-consensus    DAFEAYADEFAAEIDAL-ADISDLVDAID---D-----FQEFETTE
                   *** ********::*  :    :**:*.**       : *****
```

FIG. 26G

```
Ana-consensus          HKELQETSQQFLSATAQARIAQAEKQAQELLAF       33
Microchaete-consensus  HKELEKDTQEFLSDTAKERMAQAKEQAEQLHQF       33
Nostoc-consensus       HQNLEQTTHEFLAETTKNRTEQAKAQAQQLHQF       33
                       *::*::  :::**. *:: *  **: **:.*  *
```

FIG. 26H

GAS-FILLED STRUCTURES AND RELATED COMPOSITIONS, METHODS AND SYSTEMS TO IMAGE A TARGET SITE

CROSS REFERENCE TO RELATED APPLICATIONS

The present application is a Continuation of the U.S. application Ser. No. 16/656,417 filed on Oct. 17, 2019, which, in turn, is a Continuation of the U.S. application Ser. No. 15/613,104 filed on Jun. 2, 2017, now U.S. Pat. No. 10,493,172 issued on Dec. 3, 2019, which, in turn, claims priority to U.S. Provisional Application No. 62/344,498, entitled "Genetically Engineered Gas-Filled Nanostructures" filed on Jun. 2, 2016, which are all incorporated herein by reference in their entirety.

STATEMENT OF INTEREST

This invention was made with government support under Grant No. W911NF-14-1-0111 awarded by the Army and under Grant No. EB018975 awarded by the National Institute of Health. The government has certain rights in the invention.

FIELD

The present disclosure relates to gas-filled structures for use in imaging technologies, and related compositions methods and systems to image a target site with particular reference to imaging performed by ultrasound.

REFERENCE TO SEQUENCE LISTING

Further, the computer readable form of the sequence listing of the ASCII (XML) text file P2049-USC2-Seq-List-ST26.xml, created on Oct. 14, 2022, with a size of 145,283 bytes, is incorporated herein by reference in its entirety.

BACKGROUND

Ultrasound is among the most widely used biomedical imaging modalities due to its superior spatiotemporal resolution, safety, cost and ease of use compared to other techniques.

In addition to visualizing anatomy and physiology, ultrasound can take advantage of contrast agents to more specifically image blood flow, discern the location of certain molecular targets, and resolve structures beyond its normal wavelength limit via super-localization.

Challenges remain for identifying and developing methods and biocompatible nanoscale contrast agents for ultrasound detection of a target site obtained with high sensitivity and resolution.

SUMMARY

Provided herein are gas vesicles protein structures (GVs) with tunable acoustic properties and related compositions methods, and systems which can be used in several embodiments to perform harmonic, multiplexed and multimodal ultrasound imaging, as well as cell-specific molecular targeting.

According to a first aspect, a method to provide an ultrasound imaging of a target site contrasted with a gas vesicle protein structure (GVPS) is described. In the method, the GVPS has a selectable acoustic collapse pressure value derived from an acoustic collapse pressure profile of the GVPS type and a hydrostatic collapse pressure profile, and a midpoint of the acoustic collapse pressure profile higher than a midpoint of the hydrostatic collapse pressure profile. The method comprises: collapsing the GVPS type by applying collapsing ultrasound to the target site, the collapsing ultrasound applied at a collapsing ultrasound pressure greater than the selectable acoustic collapse pressure value. The method further comprises imaging the target site by applying imaging ultrasound to the target site, the imaging ultrasound applied at a first imaging ultrasound pressure selected to provide an uncontrasted image of the target site. In some embodiments, the collapsing ultrasound pressure is higher than the midpoint of the hydrostatic collapse pressure profile.

According to a second aspect, an ultrasound imaging method and system to be used on a target site contrasted with a first gas vesicle protein structure (GVPS) type are described. In the method the GVPS type exhibits a first acoustic collapse pressure profile and a first selectable acoustic collapse pressure value and a second GVPS type exhibiting a second acoustic collapse pressure profile and a second selectable acoustic collapse pressure value. In the method, each GVPS type exhibiting a different acoustic collapse pressure profile defined as a collapse function from which a collapse amount can be determined and a different selectable acoustic collapse pressure value from their corresponding acoustic collapse pressure profile. The method comprises selectively collapsing the first GVPS type by applying collapsing ultrasound to the target site, the collapsing ultrasound applied at a first acoustic collapse pressure value equal to or higher than the first selectable acoustic collapse pressure value and lower than the second selectable acoustic collapse pressure value. The method further comprises imaging the target site containing second, uncollapsed, GVPS type by applying imaging ultrasound to the target site, the imaging ultrasound applied at a pressure value lower than the acoustic collapse pressure value of the second gas vesicle structure type. The system comprises the first GVPS and the second GVPS in a combination for simultaneous sequential use in the ultrasound imaging method herein described.

According to a third aspect, an ultrasound imaging method and system to be used on a target site contrasted with a plurality of gas vesicle protein structure (GVPS) types are described. In the method, each GVPS type exhibits i) an acoustic collapse pressure profile defined as a collapse function from which a collapse amount can be determined, and ii) a selectable acoustic collapse pressure value, selectable acoustic collapse pressure values going from a lowest acoustic collapse pressure value to a highest acoustic collapse pressure value. the method comprises selectively collapsing GVPS type to a collapse amount higher than a collapse amount of each remaining GVPS type by applying collapsing ultrasound to the target site, the collapsing ultrasound applied at a pressure value equal to or higher than the selectable acoustic collapse pressure value of the GVPS type being collapsed and lower than an acoustic collapse pressure value of said each remaining GVPS type or types. The method further comprises imaging the target site containing the remaining GVPS type or types by applying imaging ultrasound to the target site, the imaging ultrasound applied at a pressure value lower than a lowest acoustic collapse pressure value of said each remaining GVPS type or types. The method also comprises repeating the collapsing and the imaging until all GVPS types are collapsed, thus providing a sequence of visible images of the target site, the sequence being indicative of image-by-image decreasing remaining GVPS types. The system comprises a plurality of gas vesicle protein structure (GVPS) types in a combination for simultaneous sequential use in the ultrasound imaging method herein described.

According to a fourth aspect, a method and system to tune acoustic properties of a gas vesicle protein structure (GVPS) are described. The gas vesicle protein structure (GVPS) is formed by a gas enclosed by a protein layer formed by a GvpC protein attached to other gas vesicle proteins to form the protein layer configured to be permeable to gas but not liquid. The GVPS has a selectable acoustic collapse pressure value $aP_0$ derived from an acoustic collapse pressure profile of the GVPS and a hydrostatic collapse pressure profile, and a midpoint of the acoustic collapse pressure profile higher than a midpoint of the hydrostatic collapse pressure profile. The method comprises engineering the GVPS by replacing a GvpC protein of the GVPS with: subsaturated concentrations of the GvpC protein and/or saturated or subsaturated concentrations of a genetically modified GvpC protein. In the method, the engineering is performed to obtain a variant of the GvpC protein with an acoustic collapse pressure $aP1$ lower than the $aP_0$.

According to a fifth aspect, a gas vesicle protein structure variant is described. The gas vesicle protein structure comprising a variant GvpC protein herein described.

According to a sixth aspect, a GvpC protein variant is described obtainable from a base GvpC protein having repetitions of a repeat region flanked by an N-terminal region, and a C-terminal region, by deleting at least one of the N-terminal region and C-terminal region; deleting 3 or more repeated region; deleting at least one repeated region immediately following the N-terminus, and/or adding a peptide to the C terminal or N terminal region.

According to a seventh aspect, a GvpC protein variant of a base GvpC protein having repetitions of a repeat region, flanked by an N-terminal region and a C-terminal region, is described. The GvpC variant comprises one or more repeat regions with a sub-sequence within at least one repeat region substituted with another amino sequence having a sequence similarity lower than 50% with respect to the sub-sequence within the base GvpC sequence.

According to an eight aspect, a composition is described comprising one or more GVPS, and/or one or more GvpC variant herein described and a suitable vehicle. In some embodiments, wherein the composition comprises one or more GVPS, the composition is a contrast agent for ultrasound imaging.

The gas vesicle protein structures and related variants, compositions methods and systems as well as GvpC variants herein described can be used in several embodiments in connection with ultrasound imaging of biological target site with particular reference to imaging of internal body structures of an individual such as tendons, muscles, joints, vessels and internal organs.

The gas vesicle protein structures and related variants, compositions methods and systems as well as GvpC variants herein described can be used in several embodiments to provide ultrasound imaging with enhanced harmonic responses, biodistribution, multiplexing, multimodal detection and/or molecular targeting to help ultrasound fulfill its potential as a high performance modality for molecular imaging.

The gas vesicle protein structures and related variants, compositions methods and systems as well as GvpC variants herein described can be used in several embodiments to track moving target sites such as cells or other structures within the body of an individual or other environments The gas vesicle protein structures and related variants, compositions methods and systems as well as GvpC variants herein described can be used in connection with various applications wherein ultrasound imaging of a target site is desired. For example, The gas vesicle protein structures and related variants, compositions methods and systems as well as GvpC variants herein described can be used to spatially and/or temporally control the contrast of the imaging of a biological target site and in particular internal body structure or molecular composition or cellular composition and activity of tissues of an individual in medical applications, as well diagnostics applications. Additional exemplary applications include uses of gas vesicle protein structures and related variants, compositions methods and systems as well as GvpC variants herein described in several fields including basic biology research, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 1 shows a rendition of engineered GVs illustrating GvpA as the main building block of GVs. GvpA is a structural protein that assembles through repeated unites to make up the bulk of GVs. GvpC is a scaffold protein with 5 repeat units that assemble on the outer shell of GVs. GvpC can be engineered to tune the mechanical and acoustic properties of GVs as well as act as a handle for appending moieties on to.

FIG. 2A shows an exemplary Transmission Electron Microscopy (TEM) image of a single Ana GV. FIG. 2B shows a schematic illustration of Ana GV, and the gene cluster encoding GvpA, GvpC and several other essential proteins. FIG. 2C shows GvpA and GvpC are the two major structural constituents of GVs, with GvpA ribs (light gray) forming the primary GV shell and the outer scaffold protein GvpC (dark gray) conferring structural integrity. Each GvpC molecule has five 33-amino acid repeats flanked by N- and C-terminal regions. FIG. 2D shows a schematic of an exemplary paradigm for modular genetic engineering of Ana GVs. Native gas vesicles are treated with 6M urea to produce stripped Ana GVs without native GvpC. Genetically engineered GvpC is recombinantly expressed in *Escherichia coli* and added to the stripped Ana GVs during dialysis to create engineered GVs with a modified GvpC layer. FIG. 2E shows a schematic of examples of how GvpC engineering can be used to modulate the properties of acoustic GV structures including their harmonic response, collapse pressure, surface charge, targeting specificity and fluorescence.

FIGS. 4A-4G show examples of GvpC engineering that enables tuning of GV collapse pressure for acoustic multiplexing. FIG. 4A shows a schematic illustration of three exemplary engineered GV variants used for acoustic multiplexing. ΔGvpC is shown with no gvpC (no diagonal lines), ΔN&C is shown with light grey diagonal lines representing ΔN&C gvpC mutant, and $GvpC_{WT}$ is shown with dark grey diagonal lines (WT gvpC). Accompanying TEM images (to the right of respective illustrated GV variants) show the conservation of GV shape among the three variants (scale bars are 200 nm). FIG. 4B shows graphed results of exemplary optical density (O.D.) measurements of engineered Ana GVs as a function of hydrostatic pressure (N=7 independent preparations, error bars are SEM). FIG. 4C shows graphed exemplary results of acoustic collapse curves for the GV variants showing normalized ultrasound signal intensity as a function of increasing peak positive pressure from 290 kPa to 1.23 MPa (N=3 independent trials, error bars are SEM). The data was fitted with a Boltzmann sigmoid function (parameters provided in Table 7), the derivatives of which with respect to pressure are plotted in FIG. 4D. FIG. 4E shows a schematic illustration of acoustic spectral unmixing, showing serial collapse of the exemplary GV variants based on their critical collapse pressure and indicating the pressures used in FIG. 4F and FIG. 4G. FIG. 4F shows exemplary ultrasound images of an agarose phantom containing wells with ΔGvpC, ΔN&C, $GvpC_{WT}$ and a mixture of the three variants (all GVs at final OD 1.0 in PBS), acquired at 6.25 MHz. $I_0$: before collapse $I_1$: after collapse at 630 kPa I2: after collapse at 790 kPa I3: after collapse at 1230 kPa. FIG. 4G shows exemplary spectrally unmixed images processed from the raw ultrasound data in (FIG. 4F). The bottom row of images in FIG. 4G shows an overlay of the three unmixed channels $C_1$, $C_2$, and $C_3$. The color version of FIGS. 4A-4G can be found in the Lakshmana reference [1], which is incorporated by reference in its entirety.

FIG. 7 shows an exemplary matrix of coefficients used for generating spectrally unmixed images shown in FIG. 4G from the pixel-wise ultrasound signal intensities in FIG. 4F (I), before and after exposing the GV samples to three sequentially increasing acoustic pressures ($P_i$). Δ represents the measured differential signals with $\Delta_i=I(P_{i-1})-I(P_i)$, while α is the matrix containing the acoustic collapse spectrum for each GV variant ($\alpha_{i,j}$). C represents the contribution of each GV variant to the observed signal, with $C_j$ calculated by the matrix operation: $C=\alpha^{-1}\Delta$.

FIGS. 8A-8E show exemplary results showing that GV engineering enables modulation of harmonic signals in vitro FIG. 8A shows a graph reporting exemplary power spectra of signal backscattered from ΔGvpC (light grey) and $GvpC_{WT}$ (dark grey) variants in an agarose phantom in response to 4.46 MHz pulses. FIG. 8B shows exemplary fundamental and FIG. 8C second harmonic ultrasound images of ΔGvpC and $GvpC_{WT}$ GVs acquired with 4.46 MHz transmission and band-pass filtered around 4.46 and 8.92 MHz respectively. Images are shown before and after collapse using a high power burst from the transducer to collapse the GVs. Scale bars are 1 mm. FIGS. 8D-8E show graphs reporting exemplary mean fundamental (in FIG. 8D) and harmonic (in FIG. 8E) signals from ΔGvpC and $GvpC_{WT}$ variants after filtering at the indicated frequencies (N=7 independent measurements, error bars are SEM). Data in all these figures comes from GVs prepared at OD 2.5 in PBS and loaded into 1% agarose phantoms.

FIG. 9A shows a schematic depiction of intravenous GV injection and in vivo ultrasound imaging during passage through the inferior vena cava (IVC). FIG. 9B shows exemplary fundamental and second harmonic ultrasound images taken at 4.46 MHz transmission frequency and band-pass filtered receive around 4.46 and 8.92 MHz respectively. Engineered Ana GVs at OD 23.5 in PBS were used for injections. The IVC ROI used for subsequent analysis is circled with a dashed line. The white arrow points to the increased harmonic signal observed in the IVC for the ΔGvpC variant. FIGS. 9C-9D show graphs reporting exemplary results of time course of the mean (FIG. 9C) fundamental and (FIG. 9D) harmonic acoustic signal in the IVC before, during and after steady infusion, with shaded regions representing SEM (N=6 mice). FIG. 9E shows a histogram reporting exemplary area under the curve (AUC) of average fundamental and harmonic contrast in the IVC after ΔGvpC and $GvpC_{WT}$ GV injections (N=6, error bars are SEM).

FIGS. 10A-10H show examples of genetic engineering of GV surface properties, cellular targeting and multimodal imaging. FIG. 10A shows a diagram of gvpC genetic fusions used to engineer novel GV properties and functions. FIG. 10B shows exemplary graphed results of Zeta potential measurements of engineered GVs having GvpC fused to LRP and wild-type GvpC (N=4, error bars are SEM). FIG. 10C shows exemplary confocal fluorescence images showing RGD-functionalized, RDG-functionalized and wild-type Alexa Fluor-488 fluorescently labeled (white) GVs after 24 hr incubation with U87 glioblastoma cells (DAPI-stained nuclei, light gray). Scale bars are 50 μm. FIG. 10D shows exemplary graphed results of mean GV fluorescence measured for each condition in FIG. 10C (N=3, error bars are SEM). FIG. 10E shows exemplary confocal fluorescence images of RAW 264.7 macrophages (DAPI-stained nuclei, light gray) incubated for 30 min with fluorescently labeled GVs (white) displaying GvpC fused to mCD47, R8 or wild-type GvpC. Scale bars are 50 μm. FIG. 10F shows exemplary graphed results of mean GV fluorescence measured for each condition in FIG. 10E (N=3, error bars are SEM). FIG. 10G shows in the Top row: exemplary ultrasound images of engineered and SpyCatcher-mNeonGreen (SC-mNG) reacted GVs at OD 2.5 in PBS, acquired using a 19 MHz transmission pulse in fundamental mode. Scale bars are 1 mm. The bottom row of FIG. 10G shows exemplary fluorescence images of the agarose phantoms before and after acoustic collapse. FIG. 10H shows exemplary graphed results of mean ultrasound and fluorescence signals from the GV samples tested in FIG. 10G (N≥4, error bars are SEM).

FIGS. 11A-11C show a Clustal Omega sequence alignment of exemplary genetically engineered variant GvpC proteins described herein. In particular, FIG. 11 shows the amino acid sequence of the following variants: ΔN&C-CERY1 (SEQ ID NO:35), Δnterm (SEQ ID NO:36), N-rep3-C (SEQ ID NO:37), SR3CERY1 (SEQ ID NO:38), WTCERY1 (SEQ ID NO:39), N-rep1-C (SEQ ID NO:40), SR1CERY1 (SEQ ID NO:41), ΔN&C (SEQ ID NO:42), N-rep2endto3mid-C (SEQ ID NO:43), N-His-GvpC (SEQ ID NO:44), ΔCterm (SEQ ID NO:45), GvpCWT-ACPP (SEQ ID NO:46), GvpCWT-hPRM (SEQ ID NO:47), GvpCWT-LRP (SEQ ID NO:48), GvpCWT-mCD47 (SEQ ID NO:49), GvpCWT-R8 (SEQ ID NO:50), GvpCWT-RGD (SEQ ID NO:51), GvpCWT-RDG (SEQ ID NO:52), GvpCWT (SEQ ID NO:53), GvpC-SpyTag (SEQ ID NO:54), N-rep1to3-C (SEQ ID NO:55), N-rep1to2-C (SEQ ID NO:56), and N-rep1to4-C (SEQ ID NO:57).

FIGS. 16A-16E shows amino acid GvpC sequences from 5 different organisms with the tandem repeat regions (Rep) within each gvpC protein aligned, preceded by the N-terminal region (N-term) and followed by the C-terminal region (C-term). Sequences and tandem repeats were obtained from Uniprot. FIG. 16A shows *Halobacterium salinarum*, (SEQ ID NO:4), FIG. 16B shows *Anabaena flos-aquae*, (SEQ ID NO:2), FIG. 16C shows *Halobacterium mediterranei*, (SEQ ID NO:6), FIG. 16D *Microchaete diplosiphon*, (SEQ ID NO:8), and FIG. 16E shows *Nostoc* sp., (SEQ ID NO:10).

FIG. 17 shows a table summarizing results of experiments on GVs prepared using exemplary gvpC variants described herein. For each variant, the molar concentration ratio of gvpC:gvpA used for dialysis assembly of GVs is shown (concentration). The midpoint of hydrostatic collapse pressure (pressure at which half the GV population collapse) is shown for each preparation of GVs indicated. For each preparation, it is also indicated whether the gvpC variant has a His-tag, and the location of the His-tag on the gvpC protein (C-terminus or N-terminus).

FIG. 18 shows GvpC amino acid sequence from *Anabaena flos-aquae* (SEQ ID NO:2), with the tandem repeat regions (Rep) aligned, preceded by the N-terminal region (N-term) and followed by the C-terminal region (C-term). Underlined residues indicate sites of trypsin cleavage, and residues in bold indicate regions of the protein that remain bound to gvpA following a tryptic digest.

FIG. 19A shows graphed results of exemplary optical density (O.D.) measurements of engineered Ana GVs as a function of hydrostatic pressure. GVs prepared with Rep1, Rep2to3, or Rep3 variants of gvpC were prepared 7.5:25 molar ratio of gvpC:gvpA and for the GvpC$_{WT}$ variant a gvpC:gvpA molar ratio of 2:25 was used. The data was fitted with a Boltzmann sigmoid function. FIG. 19B shows a table summarizing the midpoint of collapse (kPa) of each preparation shown in FIG. 19A.

FIG. 21A shows graphed results of exemplary optical density (O.D.) measurements of wild type Ana GVs (GV$_{WT}$) and engineered Ana GVs as a function of hydrostatic pressure. GVs were prepared with the indicated gvpC variants (gvpC:gvpA equimolar). The data was fitted with a Boltzmann sigmoid function. FIG. 21B shows a table summarizing the midpoint of collapse (kPa) of each preparation shown in FIG. 21A.

FIGS. 22A-22B summarize features of exemplary GV forming microorganisms [2].

FIG. 23 summarizes predicted products of gvp genes from *Halobacterium halobium, Halobacterium salinarium*, and *Haloferax meditteranei* [3].

FIGS. 26A-26H show exemplary sequence alignment of GvpC repeat regions from different organisms. FIG. 26A shows *Halobacterium salinarum*, r7-halsa (SEQ ID NO:58), r6-halsa (SEQ ID NO:59), r5-halsa (SEQ ID NO:60), r2-halsa (SEQ ID NO:61), r3-halsa (SEQ ID NO:62), r1-halsa (SEQ ID NO:63), r4-halsa (SEQ ID NO:64), FIG.

26B shows *Haloferax mediterranei*, r7-halmed (SEQ ID NO:65), r6-halmed (SEQ ID NO:66), r1-halmed (SEQ ID NO:67), r3-halmed (SEQ ID NO:68), r4-halmed (SEQ ID NO:69), r2-halmed (SEQ ID NO:70), r5-halmed (SEQ ID NO:71), FIG. 26C shows *Anabaena flos-aquae*, r1-ana (SEQ ID NO:72), r5-ana (SEQ ID NO:73), r4-ana (SEQ ID NO:74), r2-ana (SEQ ID NO:75), r3-ana (SEQ ID NO:76), FIG. 26D *Microchaete diplosiphon*, r1-microchaete (SEQ ID NO:77), r3-microchaete (SEQ ID NO:78), r4-microchaete (SEQ ID NO:79), FIG. 26E shows *Nostoc* sp. r1-*Nostoc* (SEQ ID NO:80), r2-*Nostoc* (SEQ ID NO:81), r3-*Nostoc* (SEQ ID NO:82), FIG. 26F shows Microcystis *aeruginosa*, r1-microcystis (SEQ ID NO:83), r2-microcystis (SEQ ID NO:84), r3-microcystis (SEQ ID NO:85), r4-microcystis (SEQ ID NO:86), r5-microcystis (SEQ ID NO:87), and r6-microcystis (SEQ ID NO:88), FIG. 26G shows a sequence alignment of the consensus sequences from *Halobacterium salinarum* and *Haloferax mediterranei*, Halmedconsensus (SEQ ID NO:89), and Halsaconsensus (SEQ ID NO:90), FIG. 26H shows a sequence alignment of the consensus sequences from *Anabaena flos-aquae*, *Microchaete diplosiphon* and *Nostoc* sp., Ana-consensus (SEQ ID NO:91), *Microchaete*-consensus (SEQ ID NO:92), and *Nostoc*-consensus (SEQ ID NO:93).

DETAILED DESCRIPTION

Figure 1:
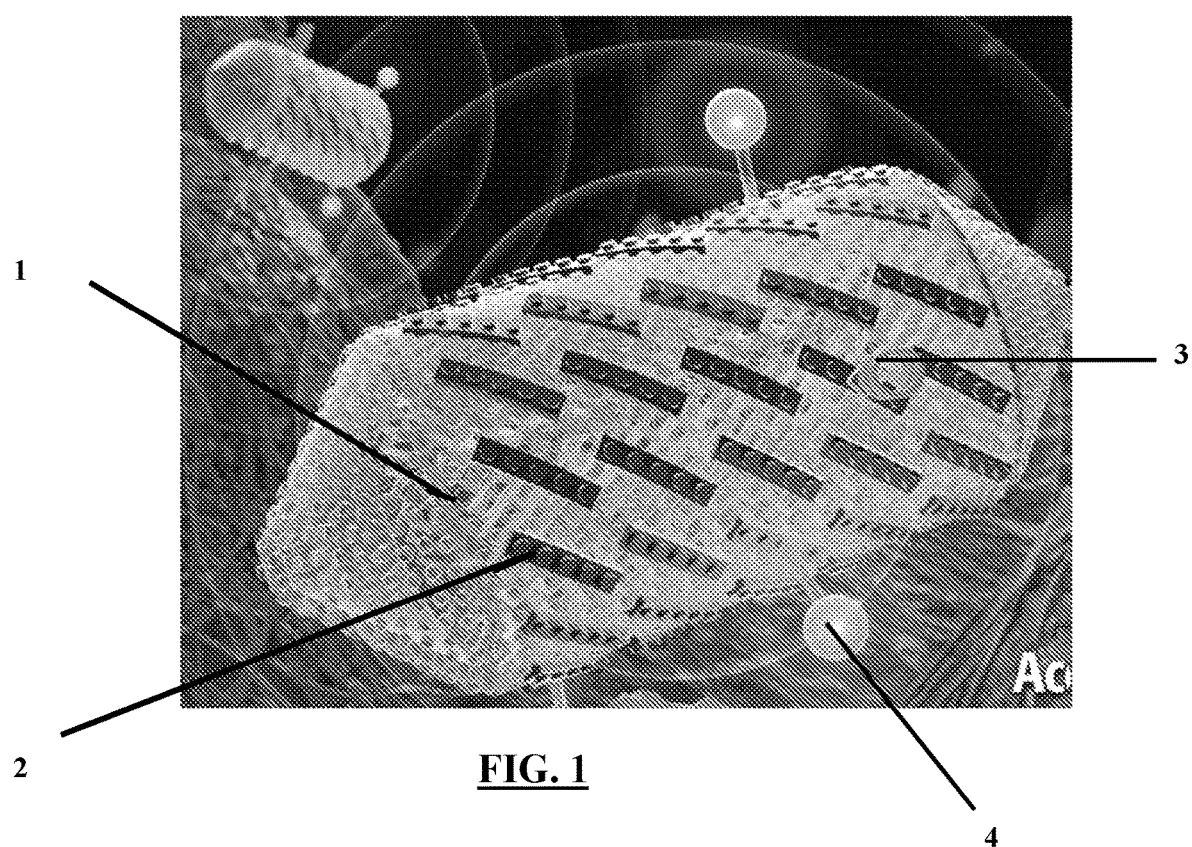

Provided herein are gas-filled protein structures, also referred to as "gas vesicles" (GVs), and related compositions methods and systems for use in ultrasound imaging particularly in contrast enhanced ultrasound imaging.

The term "contrast enhanced imaging" or "imaging", as herein indicates a visualization of a target site performed with the aid of a contrast agent administered to the target site to improve the visibility of structures or fluids by devices process and techniques suitable to provide a visual representation of a target site. Accordingly contrast agent is a substance that enhances the contrast of structures or fluids within the target site, producing a higher contrast image for evaluation.

The term "ultrasound imaging" or ultrasound scanning" or "sonography" as used herein indicate imaging performed with techniques based on the application of ultrasound. Ultrasound refers to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein refers in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. A contrast agent sometimes used with ultrasound imaging are microbubbles created by an agitated saline solution, which works due to the drop in density at the interface between the gas in the bubbles and the surrounding fluid, which creates a strong ultrasound reflection. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect to measure and visualize movement, such as blood flow rates. Types of Doppler imaging includes continuous wave Doppler, where a continuous sinusoidal wave is used; pulsed wave Doppler, which uses pulsed waves transmitted at a constant repetition frequency, and color flow imaging, which uses the phase shift between pulses to determine velocity information which is given a false color (such as red=flow towards viewer and blue=flow away from viewer) superimposed on a grey-scale anatomical image. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body.

Other ultrasound techniques and devices suitable to image a target site using ultrasound would be understood by a skilled person.

The term "target site" as used herein indicates an environment comprising one or more targets intended as a combination of structures and fluids to be contrasted, such as cells. In particular the term "target site" refers to biological environments such as cells, tissues, organs in vitro in vivo or ex vivo that contain at least one target. A target is a portion of the target site to be contrasted against the background (e.g. surrounding matter) of the target site. Accordingly, a target can include any molecule, cell, tissue, body part, body cavity, organ system, whole organisms, collection of any number of organisms within any suitable environment in vitro, in vivo or ex vivo as will be understood by a skilled person. Exemplary target sites include collections of microorganisms, including, bacteria or archaea in a solution in vitro, as well as cells grown in an in vitro culture, including, primary mammalian, cells, immortalized cell lines, tumor cells, stem cells, and the like. Additional exemplary target sites include tissues and organs in an ex vivo colture and tissue, organs, or organs systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person.

The term "individual" or "subject" or "patient" as used herein in the context of imaging includes a single plant or animal and in particular higher plants or animals and in particular vertebrates such as mammals and more particularly human beings. Types of ultrasound imaging of biological target sites include abdominal ultrasound, vascular ultrasound, obstetrical ultrasound, hysterosonography, pelvic ultrasound, renal ultrasound, thyroid ultrasound, testicular ultrasound, and pediatric ultrasound as well as additional ultrasound imaging as would be understood by a skilled person.

In embodiments herein described the ultrasound imaging of target site if performed in connection with the administration to the target site of gas vesicle protein structures.

The wordings "gas vesicles protein structure" or "GV", "GVP" or "Gas Vesicles" as used herein refer to a gas-filled protein structure intracellularly expressed by certain bacteria or archea as a mechanism to regulate cellular buoyancy in aqueous environments [3]. In particular, gas vesicles are protein structures natively expressed almost exclusively in microorganisms from aquatic habitats, to provide buoyancy by lowering the density of the cells [3]. GVs have been found in over 150 species of prokaryotes, comprising cyanobacteria and bacteria other than cyanobacteria [4, 5], from at least 5 of the 11 phyla of bacteria and 2 of the phyla of archaea described by Woese (1987) [6]. Exemplary microorganisms expressing or carrying gas vesicle protein structure include cyanobacteria such as *Microcystis aeruginosa, Aphanizomenon flos aquae Oscillatoria agardhii, Anabaena, Microchaete diplosiphon* and *Nostoc*; phototropic bacteria such as *Amoebobacter, T hiodiclyon, Pelodiclyon,* and *Ancalochloris*; non phototropic bacteria such as *Microcyclus aquaticus*; Gram-positive bacteria such as *Bacillus megalerium*; Gram-negative bacteria such as *Serratia*; and archaea such as *Haloferax mediterranei, Methanosarcina barkeri, Halobacteria salinarium* as well as additional microorganisms identifiable by a skilled person.

In particular, a GV in the sense of the disclosure is a structure intracellularly expressed by bacteria or archea forming a hollow structure wherein a gas is enclosed by a protein shell, which is a shell substantially made of protein (up at least 95% protein). In gas vesicles in the sense of the disclosure, the protein shell is formed by a plurality of proteins herein also indicated as Gvp proteins or Gvps, which are expressed by the bacteria or archea and form in the bacteria or archea cytoplasm a gas permeable and liquid impermeable protein shell configuration encircling gas. Accordingly, a protein shell of a GV is permeable to gas but not to surrounding liquid such as water. In particular, GVs' protein shells exclude water but permit gas to freely diffuse in and out from the surrounding media [7] making them physically stable despite their usual nanometer size, unlike microbubbles, which trap pre-loaded gas in an unstable configuration.

GV structures are typically nanostructures with widths and lengths of nanometer dimensions (in particular with widths of 45-250 nm and lengths of 100-800 nm) but can have lengths up to 2 μm as will be understood by a skilled person. In certain embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins [7]. For example, GVs in the sense of the disclosure can be substantially spherical, ellipsoid, cylindrical, or have other shapes such as football shape or cylindrical with cone shaped end portions depending on the type of bacteria providing the gas vesicles.

In embodiments herein described, GVs in the sense of the disclosure are capable of withstanding pressures of several kPa. but collapse irreversibly at a pressure at which the GV protein shell is deformed to the point where it flattens or breaks, allowing the gas inside the GV to dissolve irreversibly in surrounding media, herein also referred to as a critical collapse pressure, or selectable critical collapse pressure, as there are various points along a collapse pressure profile.

A collapse pressure profile as used herein indicates a range of pressures over which collapse of a population of GVs of a certain type occurs. In particular, a collapse pressure profile in the sense of the disclosure comprise increasing acoustic/hydrostatic collapse pressure values, starting from an initial collapse pressure value at which the GV signal/optical scattering by GVsstarts to be erased to a complete collapse pressure value at which the GV signal/optical scattering by GVs is completely erased. The collapse pressure profile of a set type of GV is thus characterized by a mid-point pressure where 50% of the GVs of the set type have been collapsed (also known as the "midpoint collapse pressure"), an initial collapse pressure where 5% or lower of the GVs of the type have been collapsed, and a complete collapse pressure where at least 95% of the GVs of the type have been collapsed. In embodiments herein described a selectable critical collapse pressure can be any of these collapse pressures within a collapse pressure profile, as well as any point between them. The critical collapse pressure profile of a GV is functional to the mechanical properties of the protein shell and the diameter of the shell structure. The profiles under hydrostatic pressure and under acoustic pressure are different, with the points on the acoustic pressure profile being higher in pressure than the hydrostatic profile at the midpoint collapse pressure point, at least.

In embodiments herein described, it has been surprisingly found that the critical collapse pressure is also functional to the manner in which the forces are applying the pressure to the GV shell. Accordingly, different ways of applying pressure on a set GVs result in different types of critical collapse pressures associated to the set GV. As a consequence, GVs in the sense of the disclosure are associated to more than one critical collapse pressure profile, depending on whether the pressure on the GV is applied in a hydrostatic manner (hydrostatic pressure), or applied in an acoustic manner (acoustic pressure).

The term "hydrostatic pressure" as used herein indicates the pressure exerted by a fluid at a given point within the fluid, absent fluid motion. Hydrostatic pressure includes pressure due to gravity, which pressure increases in proportion to depth measured from the surface because of the increasing weight of fluid exerting downward force from above. In addition, the hydrostatic pressure may include pressure due to forces applied to the fluid by solid surfaces adjoining the fluid, or by another fluid, such as a gas. As used herein, hydrostatic pressure does not include pressure due to sound waves.

The term the "acoustic pressure" as used herein indicates the pressure exerted by a sound wave, such as ultrasound wave, propagating through a medium. In ultrasound imaging, this wave is typically generated by an ultrasound transducer, and the pressure resulting at any time and point in the medium is determined by transducer output and patterns of constructive and destructive interference, attenuation, reflection, refraction and diffraction. Ultrasound images are generated by transmitting one or more pulses into the medium and acquiring backscattered signals from the medium, which depend on medium composition, including the presence of contrast agents.

Accordingly, in embodiments herein described each GV type has a hydrostatic collapse pressure profile and an acoustic collapse pressure profile.

It has been surprisingly found that in GVs according to the present disclosure the acoustic collapse pressure is higher than the hydrostatic collapse pressure. In particular, the acoustic collapse pressure profile of a given GV type is always shifted to higher pressures compared to its hydrostatic collapse pressure profile. The approximate mid-point acoustic collapse pressure, Pa, can be related to the mid-point hydrostatic collapse pressure, Ph, using a linear expression. This linear expression includes a non-zero positive constant, C, and a positive slope, M, such that $$Pa = C + M*Ph \quad (1)$$

In embodiments, herein described, for a given GV type, a Pa can be predicted to within ±10% error from a measured Ph value, using the parameters C=475 and M=0.64. An even more precise prediction can be made for GVs that share a substantially similar shell structure. For example, for GVs based on the Ana GV shell structure and modified by altering GvpC composition, C=396 and M=0.80 results in a prediction of Pa within an error of ±6% from Ph (see Example 27).

In embodiments, herein described, for a given GV type, the spread of the acoustic collapse pressure profile can similarly be predicted from the spread of the hydrostatic collapse pressure profile using a linear relationship with positive constant C and positive slope M, such that $\Delta Pa = C + M*\Delta Ph$. In particular, for a $\Delta Ph$ value measured for a given GV type, the corresponding Pa can be predicted to within 30 kPa using the parameters C=6.32 and M=1.15.

In embodiments herein described, the hydrostatic collapse pressure of a particular GV can be approximated by a sigmoidal function with a defined mid-point and transition width. For example, it can be defined according to Equation (2).

$$f(p) = (1 + e^{(p-p_c)/\Delta p})^{-1} \quad (2)$$

with $p_c$ defined as the mid-point and $\Delta p$ defined as the transition width. These parameters are determined for each GV type by measuring collapse as a function of pressure and fitting the resulting data with this equation, or predicted based on the GV's molecular characteristics.

Figure 4A:
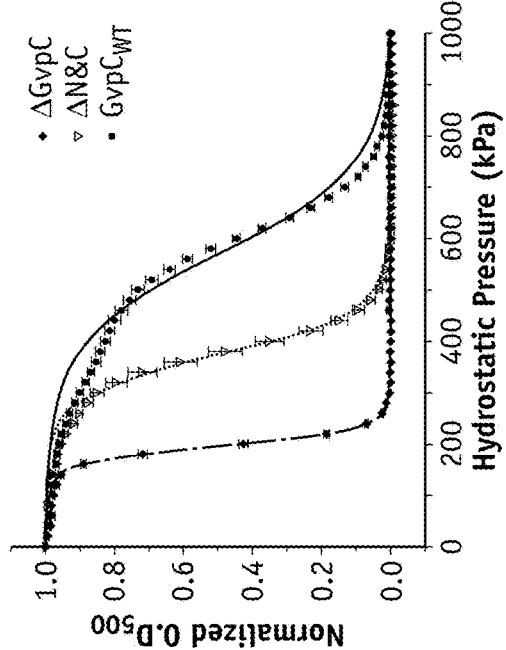
Figure 4B:
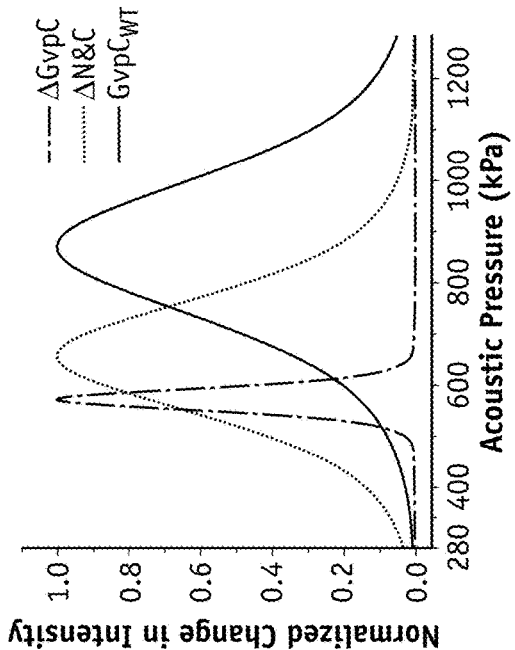

For example, the hydrostatic collapse pressure can be measured by detecting a hydrostatic collapse behavior of the GV structures using pressurized absorbance spectroscopy, in which the optical density of GVs is measured under increasing hydrostatic pressure (see FIG. 4B; Example 21)

In embodiments herein described, the collapse behavior of GVs under ultrasound exhibits a spectral pattern, as the GVs can collapse over a range or spectra of continuous increasing acoustic collapse pressure values, starting from an initial collapse pressure value at which the GV signal starts to be erased to a complete collapse pressure value at which the GV signal is completely erased.

The acoustic collapse pressures of a given GV type can be characterized by an acoustic collapse pressure profile, which is a normalized sigmoid function f(p) defined as follows:

$$f(p) = (1 + e^{(p-p_c)/\Delta p})^{-1} \quad (3)$$

where p is the applied pressure, $p_c$ is the collapse mid-point and $\Delta p$ is the variance, the latter two being parameters obtained from fitting with a sigmoid function. The acoustic collapse pressure profile shows normalized ultrasound signal intensities as a function of increasing pressures.

Figure 4C:
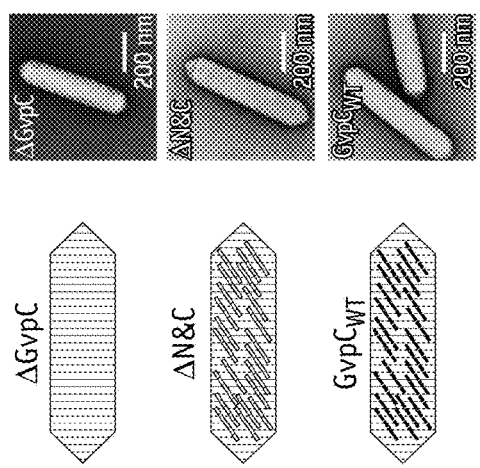

The acoustic collapse pressure profile of a given GV type can be determined by imaging GVs with imaging ultrasound energy after collapsing portions of the given GV type population with a collapsing ultrasound energy (e.g. ultrasound pulses) with increasing peak positive pressure amplitudes to obtain acoustic pressure data point of acoustic pressure values, the data points forming an acoustic collapse curve. The acoustic collapse pressure function f(p) can be derived from the acoustic collapse curve by fitting the data with a sigmoid function such as a Boltzmann sigmoid function (see Example 21). Exemplary acoustic collapse pressure curves construed accordingly for a set of three different GVs are shown in FIG. 4C).

Accordingly, acoustic collapse pressure profile in the sense of the disclosure include a set of initial collapse pressure values, a midpoint collapse pressure value and a set of complete collapse pressure values. The initial collapse pressures are the acoustic collapse pressures at which 5% or less of the GV signal is erased. A midpoint collapse pressure is the acoustic collapse pressure at which 50% of the GV signal is erased. Complete collapse pressures are the acoustic collapse pressures at which 95% or more of the GV signal is erased.

The initial collapse pressures can be obtained by solving the fitted equations for p such that $f(p) \leq 0.05$. The midpoint collapse pressure can be obtained by solving the fitted equations for p such that $f(p) = 0.5$. The complete collapse pressures can be obtained by solving the fitted equations for p such that $f(p) \geq 0.95$.

In particular, for a set GV an acoustic collapse pressure can be more than twice the hydrostatic collapse pressure for the same GV as shown by a comparison of corresponding curves built based on the detected acoustic collapse pressure values according equations (3) and on detected hydrostatic collapse pressure value according to Equation (2).

Accordingly, in methods and systems of the present disclosure and related compositions and contrast agents, identification of the acoustic collapse pressure for a set GV can be used to apply an acoustic pressure which allows sensitive and specific detection of the set GV in ultrasound imaging.

In particular, in some embodiments herein described a method to provide an ultrasound image of a target site comprises: collapsing the GVPS type by applying collapsing ultrasound to the target site, the collapsing ultrasound applied at a collapsing ultrasound pressure greater than the selectable acoustic collapse pressure value. The method further comprises imaging the target site by applying imaging ultrasound to the target site, the imaging ultrasound applied at a first imaging ultrasound pressure selected to provide an uncontrasted image of the target site.

In some embodiments, the collapsing ultrasound pressure is higher than the midpoint of the hydrostatic collapse pressure profile.

The method can further comprise administering to a target site a contrast agent comprising a gas vesicle protein structure herein described and imaging the target site by applying imaging ultrasound to the target site prior to the collapsing, the ultrasound applied at a second imaging ultrasound pressure lower than the acoustic collapse pressure value and selected to provide a visible image of the target site. Application of an ultrasound or acoustic pressure at the indicated imaging value increases sensitivity of visualization of the related GV as it minimizes the acoustic collapse of the GV in the contrast agent.

Applying ultrasound refers to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging task and, in some methods described herein, collapsing GVs. To create images, particularly 2D and 3D imaging, scanning techniques can be used where the ultrasound energy is applied in lines or slices which are composited into an image.

In some embodiments, the ultrasound imaging herein described comprising collapsing the GVPS type in the contrast agent by applying collapsing ultrasound to the target site, the collapsing ultrasound applied at a collapsing ultrasound pressure greater than the selectable acoustic collapse pressure value. As used herein, the term "selectable acoustic collapse pressure" refers to an acoustic collapse pressure value that can be selected from the acoustic collapse profile of the GVPS type.

In some embodiments, imaging the target site can be performed by scanning an ultrasound image of the target site in a subject. In some cases, imaging the target site includes transmitting an imaging ultrasound signal from an ultrasound transmitter to the target site, and receiving a set of ultrasound data at a receiver. The visible image is formed by ultrasound signals backscattered from the target site. The ultrasound data can be analyzed using a processor, such as a processor configured to analyze the ultrasound data and produce an ultrasound image from the ultrasound data. In certain embodiments, the ultrasound data detected by the receiver includes an ultrasound signal, an ultrasound signal reflected by the target site of the subject.

In certain embodiments, the method includes applying a set of imaging pulses from an ultrasound transmitter to the target site, and receiving ultrasound signal at a receiver. In certain instances, the ultrasound signal detected by the receiver includes an ultrasound echo signal. Additional information of ultrasound systems and methods can be found in related publications as will be understood by a person skilled in the art.

Methods for performing ultrasound imaging are known in the art and can be employed in methods of the current disclosure. In certain aspects, an ultrasound transducer, which comprises piezoelectric elements, transmits an ultrasound imaging signal (or pulse) in the direction of the target site. Variations in the acoustic impedance (or echogenicity) along the path of the ultrasound imaging signal causes backscatter (or echo) of the imaging signal, which is received by the piezoelectric elements. The received echo signal is digitized into ultrasound data and displayed as an ultrasound image. Conventional ultrasound imaging systems comprise an array of ultrasonic transducer elements that are used to transmit an ultrasound beam, or a composite of ultrasonic imaging signals that form a scan line. The ultrasound beam is focused onto a target site by adjusting the relative phase and amplitudes of the imaging signals. The imaging signals are reflected back from the target site and received at the transducer elements. The voltages produced at the receiving transducer elements are summed so that the net signal is indicative of the ultrasound energy reflected from a single focal point in the subject. An ultrasound image is then composed of multiple image scan lines.

In some embodiments, imaging the target site is performed by applying or transmitting an imaging ultrasound signal from an ultrasound transmitter to the target site and receiving a set of ultrasound data at a receiver. The ultrasound data can be obtained using a standard ultrasound device, or can be obtained using an ultrasound device configured to specifically detect the contrast agent used. Obtaining the ultrasound data can include detecting the ultrasound signal with an ultrasound detector. In some embodiments, the imaging step further comprises analyzing the set of ultrasound data to produce an ultrasound image.

In certain embodiments, the ultrasound signal has a transmit frequency of at least 1 MHz, 5 MHz, 10 MHz, 20 MHz, 30 MHz, 40 MHz or 50 MHz. For example, an ultrasound data is obtained by applying to the target site an ultrasound signal at a transmit frequency from 4 to 11 MHz, or at a transmit frequency from 14 to 22 MHz. In some instances, the imaging frequency is selected so as to maximize the contrast generated by the administered contrast agent.

In the embodiments herein described, the collapsing ultrasound and imaging ultrasound are selected to have a collapsing pressure and an imaging pressure amplitude based on the acoustic collapse pressure profile of the GVPS type used in the contrast agent. In some instances, the ultrasound pressure, including the collapsing ultrasound pressure and the imaging ultrasound pressure can be referred to as the "peak positive pressure" of the ultrasound pulses. The term "peak positive pressure" refers to the maximum pressure amplitude of the positive pulse of a pressure wave, typically in terms of the difference between the peak pressure and the ambient pressure at the location in the person or specimen that is being imaged.

In some embodiments, the collapsing ultrasound transmit pulses are selected to have a peak positive pressure amplitude equal to or higher than an initial collapse pressure in the acoustic collapse profile of the GVPS used in the contrast agent administered to the target site.

In some embodiments, the collapsing ultrasound transmit pulses are selected to have a peak positive pressure amplitude equal to or higher than the midpoint collapse pressure in the acoustic collapse profile of the GVPS used in the contrast agent administered to the target site.

In some embodiments, the collapsing ultrasound transmit pulses are selected to have a peak positive pressure amplitude equal to or higher than a complete collapse pressure in the acoustic collapse profile of the GVPS used in the contrast agent administered to the target site.

In some embodiments, collapsing the GV type is followed by imaging the target site by applying imaging ultrasound to the target site, the imaging ultrasound applied at a first imaging ultrasound pressure selected to provide an uncontrasted image of the target site.

In some embodiments, the imaging ultrasound transmit pulses are selected to have a peak positive pressure amplitude equal to or lower than an initial collapse pressure in the acoustic collapse profile of the GVPS used in the contrast agent administered to the target site.

In some embodiments, the imaging ultrasound transmit pulses are selected to have a peak positive pressure amplitude equal to or lower than a midpoint collapse pressure in the acoustic collapse profile of the GVPS used in the contrast agent administered to the target site.

In some embodiments, the imaging ultrasound transmit pulses are selected to have a peak positive pressure amplitude equal to or lower than a complete collapse pressure in the acoustic collapse profile of the GVPS used in the contrast agent administered to the target site.

In some embodiments, prior to collapsing the GV type, the ultrasound imaging method further comprises imaging the target site by applying imaging ultrasound to the target site, the imaging ultrasound applied at a second imaging ultrasound pressure lower than the selectable acoustic collapse pressure and selected to provide a visible image; and comparing the visible image of the target site with the uncontrasted image. In some embodiments, different ultrasound pressure values can be used for imaging at different steps of the process. In other embodiments, the pressure used for imaging can be constant throughout the method.

In some embodiments, the collapsing ultrasound pressure is selected to be equal to or higher than the midpoint collapse pressure, preferably equal to or higher than the complete collapse pressure, in the acoustic collapse profile of the GV, and the first and second imaging ultrasound pressure is equal to or lower than the midpoint collapse pressure, preferably equal to or lower than the initial collapse pressure, in the acoustic collapse profile of the GV.

In some embodiments, the collapsing ultrasound pressure used to collapse the GVPS type is higher than the midpoint of the hydrostatic collapse pressure profile of the GVPS type.

In some embodiments, imaging the target site using ultrasound imaging method comprises applying a first imaging ultrasound signal having a first imaging peak positive pressure from an ultrasound transmitter to the target site, receiving a first set of ultrasound data at a receiver, and analyzing the first set of ultrasound data to produce a first ultrasound image; applying a collapsing ultrasound signal having a first collapsing peak positive pressure from the ultrasound transmitter to the target site; applying a second imaging ultrasound signal having a second imaging peak positive pressure from the ultrasound transmitter to the target site, receiving a second set of ultrasound data at the receiver, analyzing the second set of ultrasound data to produce a second ultrasound image; and processing the first and second set of ultrasound data.

In particular, the first imaging peak positive pressure and the second imaging peak positive pressure can be the same and both lower than the initial collapse pressure of the GV used in the contrast agent, and the collapsing peak positive pressure is higher than the complete collapse pressure of the GV. In such case, the first image represents a contrasted image of the target site containing the uncollapsed GVs and the second image represents uncontrasted image of the target site containing the collapsed GVs. The processing the first and second set of ultrasound data involves subtracting the second image from the first image.

In some embodiments, the method further comprises obtaining the acoustic collapse pressure profile of the GVPS type administered to the target site. The acoustic collapse pressure profile of the GVPS type can be obtained by imaging GVPS, in vivo or in vitro, with imaging ultrasound energy after collapsing portions of the given GVPS type population with a collapsing ultrasound energy (e.g. ultrasound pulses) with increasing peak positive pressure amplitudes and constructing an acoustic pressure profile for the GVPS type. Alternatively, the acoustic collapse profile can be obtained from the hydrostatic collapse pressure profile of the GVPS type according to equation (1).

In some embodiments, the GVPS type can be wild-type GVPS from any bacterial origin or variants thereof. For example, the GVPS type can be a wild-type Ana GV containing the wild-type GvpC having an acoustic collapse pressure profile defined by an initial collapse pressure of 650 kPa and a complete collapse pressure of 1,100 kPa. The first and second imaging ultrasound pulses can be acquired with a transmit pressure below 650 kPa and the collapsing ultrasound pulses can be acquired with a transmit pressure above 1,100 kPa.

In methods herein described, administering the contrast agent can be performed in any way suitable to deliver a GV to the target site to be imaged. In some embodiments, the contrast agent can be administered to the target site locally or systemically.

The wording "local administration" or "topic administration" as used herein indicates any route of administration by which a GV is brought in contact with the body of the individual, so that the resulting GV location in the body is topic (limited to a specific tissue, organ or other body part where the imaging is desired). Exemplary local administration routes include injection into a particular tissue by a needle, gavage into the gastrointestinal tract, and spreading a solution containing GVs on a skin surface.

The wording "systemic administration" as used herein indicates any route of administration by which a GV is brought in contact with the body of the individual, so that the resulting GV location in the body is systemic (i.e. non limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

Accordingly, in some embodiments of methods herein described, administering a contrast agent can be performed topically or systemically by intradermal, intramuscular, intraperitoneal, intravenous, subcutaneous, intranasal, rectal, vaginal, and oral routes. In particular, a contrast agent can be administered by infusion or bolus injection, by absorption through epithelial or mucocutaneous linings (e. g., oral mucosa, vaginal, rectal and intestinal mucosa, etc.) and can optionally be administered together with other biologically active agents. In some embodiments of methods herein described, administering a contrast agent can be performed by injecting the contrast agent into a subject at the target site of interest, such as in a body cavity or lumen. In some embodiments, it can be performed by spreading a solution containing the contrast agent on a region of the skin.

In some embodiments, the contrast agents are administered to the target site with the selected GVPS type at a sufficient concentration to be visible by ultrasound in the context of the background tissue. The saturated concentration for gas vesicles are typically above 10 pM.

In some embodiments, a multiplexed ultrasound imaging method is described. The term "multiplex" refers to the presence of two or more distinct GVPS types, each of which exhibits an acoustic collapse pressure profile distinct from one another. The two or more distinct GVPSs can be derived from different bacteria or variants of GVPSs from the same or different bacteria.

In particular, in some embodiments, methods for multiplexed imaging of a target site herein described comprise an ultrasound imaging method to be used on a target site contrasted with a contrast agent comprising at least a first gas vesicle protein structure (GVPS) type and a second GVPS type is described. In the method, the first GVPS type exhibits a first acoustic collapse pressure profile and a first selectable acoustic collapse pressure value and a second GVPS type exhibits a second acoustic collapse pressure profile and a second selectable acoustic collapse pressure value. GVPS Each acoustic collapse pressure profile is defined as a collapse function from which a collapse amount can be determined and a different selectable acoustic collapse pressure value can be selected from their corresponding acoustic collapse pressure profile.

The method comprises selectively collapsing the first GVPS type by applying collapsing ultrasound to the target site, the collapsing ultrasound applied at a first collapsing pressure value equal to or higher than the first selectable acoustic collapse pressure value and lower than the second selectable acoustic collapse pressure value.

The method further comprises imaging the target site containing second, uncollapsed, GVPS type by applying imaging ultrasound to the target site, the imaging ultrasound applied at an imaging pressure value lower than the acoustic collapse pressure value of the second gas vesicle structure type In multiplexing methods herein described, both the collapsing pressure of the collapsing ultrasound and the imaging pressure of the imaging ultrasound are selected based on the acoustic collapse pressure profiles of the GVPS types to selectively collapse one GVPS type over the other GVPS types.

The term "selectively collapse" refers to collapsing at least a portion of one GVPS type in a greater amount that any other GVPS type in a mixture containing a plurality of GVPS types. For any two given GVPS types each exhibiting an acoustic pressure profile characterized by f(p), the collapsing pressure is selected to have a f1(p) value for the first GVPS type greater than a f2(p) value for the second GVPS type in order to selectively collapse the first GVPS type.

In some embodiments, the collapsing pressure of the collapsing ultrasound is equal to a maximally informative collapse pressure ("MIAP") of two spectrally adjacent GV types.

The term "maximally informative collapse pressure" or "MIAP" as used herein indicates an acoustic pressure chosen based on the acoustic collapse profiles of the two GV types such that the fraction of the first GV collapsed at this pressure is maximally different from the fraction of the second GV collapsed at this pressure.

Accordingly, a maximally informative acoustic pressure (MIAP) value for a set GVPS relative to another one or more GVPS types in a GVPS mixture can be performed based on acoustic collapse profiles construed using detected acoustic collapse pressure values according to Equation (3). In particular, for GVPSs in a set GVPS mixture the MIAP can be expressed as a pressure by maximizing $\Delta f(p)$, i.e. $f1(p)-f2(p)$, wherein $f1(p)=(1+e^{(p-p_c)/\Delta p})^{-1}$ and $f2(p)=(1+e^{(p-p_c)/\Delta p})^{-1}$) (4)

f1(p) and f2(p) corresponds to an acoustic collapse profile of the first GVPS and the second GVPS.

The target site is then imagined following the collapsing by applying an imaging ultrasound. The imaging pressure of the imaging ultrasound is selected to be equal to or lower than the acoustic collapse pressures of remaining uncollapsed GVPS types in the target site. Preferably, the imaging pressure of the imaging ultrasound is selected to be equal to or lower than the initial acoustic collapse pressures of the remaining uncollapsed GVPS types in the target site. More preferably, the imaging pressure of the imaging ultrasound is selected to be equal to or lower than the lowest initial collapse pressures of all the GVPS types in the contrast agent, including the collapsed GVPS type.

In some embodiments, the multiplexed ultrasound imaging method further comprises after imaging the target site containing the second, uncollapsed GVPS type, collapsing the second GVPS type by applying a second collapsing ultrasound and imaging the target site containing the collapsed GVPS types by applying a second imaging ultrasound. The second collapsing pressure is higher than the first collapsing pressure. In some embodiments, the second collapsing pressure is higher than the complete collapse pressure of the second GVPS type.

In some embodiments, the multiplex ultrasound imaging method further comprises, prior to collapsing the first GVPS type, imaging the target site containing uncollapsed GVPS types, the imaging ultrasound applied at an imaging pressure value lower than the selectable acoustic collapse pressure value for the first GVPS type, thus obtaining an image indicative of uncollapsed first and second gas vesicle protein structure types.

For example, Ana GVs with wild-type GvpC (first GVPS type) and Ana GVs with GvpCΔN&C (second GVPS type) can be imaged in duplex by selecting the MIAP to be 630 kPa. In this case, the first imaging pulse is applied at a pressure below the initial collapse pressures of both GVPS types and an image is acquired. Then, a second pulse is applied at 630 kPa. Then, a third pulse is applied at the same pressure as the first pulse to form the second image. Then, a fourth pulse is applied at a pressure above the complete collapse pressure of the second GV type. Then, a fifth pulse is applied at the same pressure as the first pulse to form a third image.

Figure 27:
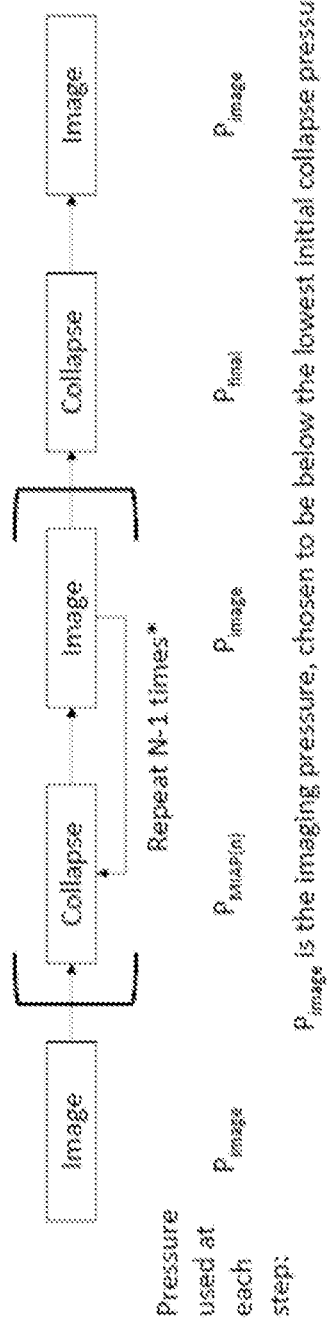
FIG. 27 shows an exemplary schematic illustration of a multiplexing ultrasound imaging method. N different GV types are each assigned an index, n, from 1 to N according to their midpoint acoustic collapse pressure, in ascending order. $P_{image}$ is the imaging pressure, chosen to be below the lowest initial collapse pressure. $P_{MIAP(n)}$ is the MIAP relating the n'th GV type and (n+1)'th GV type. $P_{final}$ is a pressure above the highest complete collapse pressure within the GV type. This procedure results in N+1 images, which are then used to reconstruct the relative abundance of each GV type via spectral unmixing. The step in the bracket can be skipped if N=1.

In some embodiments, for N number of GVPS types contained in the contrast agent, N+1 number of ultrasound images are generated (see FIG. 27). The collapsing and imaging steps are alternated so that each collapsing step is followed by an imaging step, in which the collapsing pressure of the collapsing ultrasound is higher than the imaging pressure of the imaging ultrasound.

In some embodiments, a multiplexed imaging method comprises the following steps:
  applying a base imaging ultrasound pressure from an ultrasound transmitter to the target site, receiving a base set of ultrasound data at a receive, and analyzing the base set of ultrasound data to produce a base ultrasound image; the base ultrasound image represents a pre-collapse baseline.
  applying a first collapsing ultrasound pressure from an ultrasound transmitter to the target site, applying a first imaging ultrasound pressure, receiving a first set of ultrasound data at a receiver, and analyzing the first set of ultrasound data to produce a first ultrasound image; and
  applying a second collapsing ultrasound pressure from an ultrasound transmitter to the target site, applying a second imaging ultrasound pressure, receiving a second set of ultrasound data at a receiver, and analyzing the second set of ultrasound data to produce a second ultrasound image.

In particular, in embodiments of methods herein described, the imaging ultrasound pressures can be the same or different, preferably lower than the initial acoustic collapse pressures of the remaining uncollapsed GV types in the target site, or even more preferably lower than the lowest initial collapse pressures of the GV types used in the contrast agent. The first and second collapsing ultrasound pressures are selected based on the acoustic collapse pressure profiles of the GV types, with the second collapsing ultrasound pressure higher than the first collapsing ultrasound pressure.

In certain embodiments, imaging the target site further can comprise applying at least a third collapsing ultrasound pressure from an ultrasound transmitter to the target site, applying a third imaging ultrasound pressure, receiving a third set of ultrasound data at a receiver, and analyzing the third set of ultrasound data to produce a third ultrasound image. The third collapsing ultrasound pressure is selected to be higher than the second collapsing ultrasound pressure, preferably higher than the complete collapse pressure of the third GVPS type.

In some embodiments, the multiplexed ultrasound imaging method further comprises obtaining a first acoustic collapse pressure profile of a first GV and at least a second acoustic collapse pressure profile of at least a second GV, and calculating a first maximally informative collapse pressure from the obtained first and second acoustic collapse pressure profiles. Each acoustic collapse pressure profile is characterized by a fitted sigmoid function f(p) as described above.

In some embodiments, the multiplexing ultrasound imaging method further comprises obtaining a third acoustic collapse pressure profile of a third GV, and calculating a second maximal informative collapse pressure from the obtained second and third acoustic collapse pressure profiles.

In some embodiments, the multiplexed ultrasound imaging method further comprises applying a base imaging ultrasound pressure having a base peak positive pressure lower than the lowest initial collapse pressure of the GVPS types, receiving a base set of ultrasound data at a receive, and analyzing the base set of ultrasound data to produce a base ultrasound image;
  selectively collapsing the first GVPS type by applying collapsing ultrasound having a first collapsing pressure amplitude equal to the first maximal informative collapse pressure, imaging the target site by applying imaging ultrasound having a first imaging pressure, receiving a first set of ultrasound data at a receiver, and analyzing the first set of ultrasound data to produce a first ultrasound image;
  selectively collapsing the second GVPS by applying collapsing ultrasound having a second collapsing pressure amplitude equal to the second maximal informative collapse pressure, imaging the target site by applying imaging ultrasound having a second imaging pressure, receiving a second set of ultrasound data at the receiver, and analyzing the second set of ultrasound data to produce a first ultrasound image;
  selectively collapsing the third GVPS by applying collapsing ultrasound having a third collapsing pressure amplitude greater than the highest complete collapse pressure of the GVPSs, imaging the target site by applying imaging ultrasound having a third imaging pressure, receiving a third set of ultrasound data at the receiver, and analyzing the third set of ultrasound data to produce a third ultrasound image; and processing the produced images.

In particular, the first, second and third imaging ultrasound pressure can be equal to the base imaging ultrasound pressure, which are lower than the lowest initial collapse pressure of the GVPS types administered to the target site.

In certain embodiments of multiplexed methods herein described, imaging a target site can be performed by unmixing the ultrasound signal of one or more GVPS types using multiple ultrasound signals selected to provide to the target site a suitable acoustic pressure directed to selectively image and/or collapse one or more GVPS types of a plurality of GVPS types administered to the target site.

For example, in a contrast agent comprising $\Delta$GvpC, $\Delta$N&C and $GvpC_{WT}$, the first collapsing pressure is equal to the first maximal informative acoustic pressure of 630 kPa calculated based on the acoustic collapse profiles of $\Delta$GvpC variant and $\Delta$N&C variant. The first maximal informative acoustic pressure is capable of maximally collapsing the $\Delta$GvpC variant while minimally collapsing the other two variants, i.e. $\Delta$N&C and $GvpC_{WT}$. The second collapsing pressure is equal to the second maximal informative acoustic pressure of 790 kPa calculated based on the acoustic collapse profiles of $\Delta$N&C variant and $GvpC_{WT}$. The second maximal informative acoustic pressure is capable of maximally collapsing the $\Delta$N&C variant while minimally collapsing the remaining variant, i.e. $GvpC_{WT}$. The third collapsing pressure is about 1230 kPa, higher than the complete collapse pressure of $GvpC_{WT}$ in order to collapse the remaining $GvpC_{WT}$ variant.

In some embodiments, the multiplexing ultrasound imaging method further comprises obtaining an acoustic pressure profile of each GVPS type administered to the target site. The acoustic collapse pressure profile of each GVPS type can be obtained by imaging the GVPS, in vivo or in vitro, with imaging ultrasound energy after collapsing portions of the given GVPS type population with a collapsing ultrasound energy (e.g. ultrasound pulses) with increasing peak positive pressure amplitudes and constructing an acoustic collapse pressure profile for the GVPS type. Alternatively, the acoustic collapse pressure profile can be obtained from a hydrostatic collapse pressure profile of the GVPS type according to equation (1).

In some embodiments, a multiplexing ultrasound imaging a target site contrasted with a plurality of gas vesicle protein structure (GVPS) types can be performed with a multiplex method using a plurality of GVs types. In the method, each GVPS type exhibits i) an acoustic collapse pressure profile defined as a collapse function from which a collapse amount can be determined, and ii) a selectable acoustic collapse pressure value, selectable acoustic collapse pressure values going from a lowest acoustic collapse pressure value to a highest acoustic collapse pressure value. the method comprises selectively collapsing GVPS type to a collapse amount higher than a collapse amount of each remaining GVPS type by applying collapsing ultrasound to the target site, the collapsing ultrasound applied at a pressure value equal to or higher than the selectable acoustic collapse pressure value of the GVPS type being collapsed and lower than an acoustic collapse pressure value of said each remaining GVPS type or types. The method further comprises imaging the target site containing the remaining GVPS type or types by applying imaging ultrasound to the target site, the imaging ultrasound applied at a pressure value lower than a lowest acoustic collapse pressure value of said each remaining GVPS type or types. The method also comprises repeating the collapsing and the imaging until all GVPS types are collapsed, thus providing a sequence of visible images of the target site, the sequence being indicative of image-by-image decreasing remaining GVPS types.

In the embodiments herein described, the multiplexed ultrasound imaging method further comprises an initial preparation step of administering to the target site a contrast agent comprising the plurality of gas vesicle protein structure types.

In those embodiments, imaging the target site further comprises processing the produced images using acoustic spectral unmixing to obtain spectrally unmixed images (Example 21). The term "acoustic spectral unmixing" or "pressure spectral unmixing" refers to a mathematical image processing method for obtaining spectrally unmixed images by subtracting each sub-population of signals from a sum of signal contributed by each sub-population present in any given pixel.

In those embodiments that the total signal for a mixed population of GVs in any given pixel is the sum of signals contributed by each sub-population present in that pixel. By acquiring images while sequentially applying collapse pulses of increasing pressure ($P_i$), the change in the pixel-wise signal intensity (I) between different pulses contains information about the abundance of each GV type in the pixel (FIG. 4E). This information is extracted by multiplying the measured differential signals $$\Delta_i = I(P_{i-1}) - I(P_i) \quad (5)$$

by the inverse of a matrix containing the differential collapse profile of each type of GV, denoted by $\alpha_{i,j}$. For GV type j, the application of pressure $P_i$ in a specific sequence of applied pressures results in the collapse of a fraction of that GV type corresponding to $\alpha_{i,j}$. The value of $\alpha_{i,j}$ for a given GV type is calculated from the corresponding acoustic collapse profile described by a sigmoidal function $f(p)_j$, such that $\alpha_{1,j}$ is the difference between 1 and the fraction of GVs intact at $P_1$, and $\alpha_{2,j}$ is the difference between the fraction of GVs intact at $P_1$ and the fraction of GVs intact at $P_2$, and so on. More generally, $\alpha_{i,j}$ is the difference between the fraction of GVs intact at $P_{i-1}$ and the fraction of GVs intact at $P_i$.

The contribution of each GV type to the observed signal, represented as $C_j$, is given by the matrix operation:

$$C = \alpha^{-1} \Delta. \quad (6)$$

In some embodiments, the GVs can be engineered to modulate the GV mechanical, acoustic, surface and targeting properties in order to achieve enhanced harmonic responses and multiplexed imaging to be better distinguished from background tissues.

In embodiments herein described Gas vesicles protein structures can be provided by Gvp genes endogenously expressed in bacteria or archea. Endogenous expression refers to expression of Gvp proteins forming the protein shell of the GV in bacteria or archaea that naturally produce gas vesicles encoded (e.g. in their genome or native plasmid DNA).

Gvp proteins expressed by bacteria or archea typically include two primary structural proteins, here also indicated as GvpA and GvpC, and several putative minor components and chaperones [2, 8, 9] as would be understood by a person skilled in the art.

Reference is made to the illustration of FIG. 1 showing a schematic representation of the structure of a GV. In the illustration of FIG. 1 GvpA and GvpC are indicated as the two major structural constituents of GVs, with GvpA ribs (1) (gray) forming the primary GV shell and the outer scaffold protein GvpC (2) (black) conferring structural integrity. In particular, in the illustration of FIG. 1, the light gray elements represent the proteinaceous gas vesicle shell, comprising multiple copies of GvpA and other minor structural constituents. In the illustration of FIG. 1, the dark rectangles (2) bound to the surface of the gas vesicle shell represent GvpC, a protein that affects mechanical and acoustic properties of the gas vesicle.

In bacteria or archaea expressing GVs, the Gvp proteins forming a GV's protein shell are encoded by a cluster of 8 to 14 different genes depending on the host bacteria or archaea, as will be understood by a skilled person.

The term "gene cluster" as used herein means a group of two or more genes found within an organism's DNA that encode for two or more polypeptides or proteins, which collectively share a generalized function or are genetically regulated together to produce a cellular structure and are often located within a few thousand base pairs of each other. The size of gene clusters can vary significantly, from a few genes to several hundred genes [10]. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

In embodiments herein described, identification of a gene cluster encoding for Gvp proteins in a bacteria or archaea can be performed for example by isolating the GVs from the bacteria or archaea, isolating the protein for the protein shell of the GV and derive the related amino acidic sequence with methods and techniques identifiable by a skilled person. The sequence of the genes encoding for the Gvp proteins can then be identified by method and techniques identifiable by a skilled person. For example, gas vesicle gene clusters can also be identified by persons skilled in the art by performing gene sequencing or partial- or whole-genome sequencing of organisms using wet lab and in silico molecular biology techniques known to those skilled in the art. As understood by those skilled in the art, gas vesicle gene clusters can be located on the chromosomal DNA or native plasmid DNA of microorganisms. After performing DNA or cDNA isolation from a microorganism, the polynucleotide sequences or fragments thereof or PCR-amplified fragments thereof can be sequenced using DNA sequencing methods such as Sanger sequencing, DNASeq, RNASeq, whole genome sequencing, and other methods known in the art using commercially available DNA sequencing reagents and equipment, and then the DNA sequences analyzed using computer programs for DNA sequence analysis known to skilled persons.

Gas vesicle gene cluster genes [2, 8, 9] can also be identified in DNA sequence databases such as GenBank, EMBL, DNA Data Bank of Japan, and others. Gas vesicle gene cluster gene sequences in databases such as those above can be searched using tools such as NCBI Nucleotide BLAST and the like, for gas vesicle gene sequences and homologs thereof, using gene sequence query methods known to those skilled in the art.

Exemplary genes present in the gene cluster for haloarchael GVs (which have the largest number of different gyp genes) and their predicted function and features are illustrated in Example 26.

Representative examples of endogenously expressed GVs are the gas vesicle protein structure produced by the Cyanobacterium *Anabaena flos-aquae* (Ana GVs) [3], and the *Halobacterium Halobacterium salinarum* (Halo GVs) [2]. In particular, Ana GVs are cone-tipped cylindrical structures with a diameter of approximately 140 nm and length of up to 2 m and in particular 200-800 nm or longer, encoded by a cluster of nine different genes, including the two primary structural proteins, GvpA and GvpC, and several putative minor components and putative chaperones [11] as would be understood by a person skilled in the art. Halo GVs are typically spindle-like structures with a maximal diameter of approximately 250 nm and length of 250-600 nm, encoded by a cluster of fourteen different genes, including the two primary structural proteins, GvpA and GvpC, and several putative minor components and putative chaperones [11] as would be understood by a person skilled in the art In embodiments herein described Gas vesicles protein structures can be provided by Gvp genes heterologously expressed in bacteria or archaea. Heterologous expression refers to expression of Gvp proteins in any species that either does not naturally produce gas vesicles, or where its natural production of gas vesicles has been suppressed, for example through genetic knock-out of the genes encoding Gvp proteins, and where foreign DNA encoding gas vesicle genes is introduced into the organism to persist as a plasmid or integrate into the genome.

In some embodiments, heterologously expressed Gvp genes can comprise genes encoding for corresponding Gvp proteins which are naturally occurring or have sequences having at least 50% identity with naturally occurring Gvp proteins.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that the similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank and UniProt and others identifiable to those skilled in the art.

As understood by those skilled in the art, determination of percent identity between any two sequences can be accomplished using a mathematical algorithm. Non-limiting examples of such mathematical algorithms are the algorithm of Myers and Miller [12], the local homology algorithm of Smith et al. [13]; the homology alignment algorithm of Needleman and Wunsch [14]; the search-for-similarity-method of Pearson and Lipman [15]; the algorithm of Karlin and Altschul [16], modified as in Karlin and Altschul [17]. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA [15], and TFASTA in the Wisconsin Genetics Software Package, Version 8 (available from Genetics Computer Group (GCG), 575 Science Drive, Madison, Wis., USA). Alignments using these programs can be performed using the default parameters.

In some embodiments, heterologously expressed Gvp proteins to provide a GV type have independently at least 50% sequence identity, preferably at least 80%, more preferably at least 90%, most preferably at least 95% sequence identity compared to a reference sequence of corresponding Gvp protein using one of the alignment programs described using standard parameters.

In some exemplary embodiments, the wild-type or native GVs used herein can be produced by *Anabaena flos-aquae* (Ana GVs) with their primary GvpC protein encoded by SEQ ID NO:2. Alternatively, the native GVs used herein can be derivatives of native GVs having one or more variations including insertions, deletions or replacement with at least 30% preferably at least 80% identity with respect to SEQ ID NO:2 and an E-value of less than 0.00001. GvpC proteins from other microorganisms can also be used as a reference sequence including the sequences listed in Table 4.

Heterologous expression of GVs in bacteria or archaea that do not express GVs can be performed by cloning one or more polynucleotides encoding naturally occurring Gvp proteins or homologs thereof that are required for production of GVs (comprising gvpA, gvpC, and other proteins known to those skilled in the art and described herein) into one or more suitable expression plasmids or vectors, and expressing the heterologous GV proteins in the bacteria or archaea. Polynucleotides encoding GV protein genes can be cloned using commercially available reagents from vendors such as Qiagen, Invitrogen, Applied Biosystems, Promega, and others, following standard molecular biology methods known in the art, such as those described herein. As would be understood by those skilled in the art, polynucleotides encoding GV protein genes can be obtained from several different sources. For example, polynucleotides encoding GV proteins can be obtained by isolating genomic DNA or cDNA encoding GV proteins from microorganisms whose genomes encode GV proteins genes, and/or express GV proteins RNA. RNA can be isolated from a cell that expresses GV proteins genes, and cDNA produced by reverse transcription using standard techniques and commercial kits. Genomic DNA can be purified from the cell, and cDNA or genomic DNA encoding one or more GV proteins isolated, following methods known to those in the art. Alternatively, polynucleotides comprising one or more gas vesicle genes can be synthesized using oligonucleotide and polynucleotide synthetic methods known in the art. PCR-based amplification of one or more GV protein genes can be performed using appropriately designed primer pairs (e.g. using PrimerDesign or other programs known to those skilled in the art). PCR-based amplification can be followed by ligation (e.g. using T4 DNA ligase) of a polynucleotide encoding gas vesicle gene amplicon into an appropriate expression cassette in a plasmid suitable for propagation in bacteria or other cells, such as transformation-competent *E. coli* DH5alpha, followed by growth of transformed cell cultures, purification of the plasmid for confirmation of the cloned enzyme by DNA sequence analysis, among other methods known to those skilled in the art. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences that are compatible with the bacteria or archaea heterologously expressing the GV, as would be understood by a skilled person. Promoters can be constitutively active or inducible. Exemplary inducible expression systems comprise IPTG-inducible expression as described in the Examples.

In some embodiments, where one or more Gvp proteins are expressed heterologously to form GVs in microorganisms other that the native host, the related sequence can be optimized for expression in the heterologous host microorganism as will be understood by a skilled person.

In particular, in some embodiments described herein, wherein GV is produced heterologously production of a GV gvpc gene sequences can be codon-optimized for expression in one or more microorganism of choice such as *Escherichia coli*, according to methods identifiable by a skilled person. As would be understood by those skilled in the art, the term "codon optimization" as used herein refers to the introduction of synonymous mutations into codons of a protein-coding gene in order to improve protein expression in expression systems of a particular organism, such as *E. coli* in accordance with the codon usage bias of that organism. The term "codon usage bias" refers to differences in the frequency of occurrence of synonymous codons in coding DNA. The genetic codes of different organisms are often biased towards using one of the several codons that encode a same amino acid over others—thus using the one codon with, a greater frequency than expected by chance. Optimized codons in microorganisms, such as *Escherichia coli* or *Saccharomyces cerevisiae*, reflect the composition of their respective genomic tRNA pool. The use of optimized codons can help to achieve faster translation rates and high accuracy.

In the field of bioinformatics and computational biology, many statistical methods have been proposed and used to analyze codon usage bias. Methods such as the 'frequency of optimal codons' (Fop), the Relative Codon Adaptation (RCA) or the 'Codon Adaptation Index' (CAI) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes. There are many computer programs to implement the statistical analyses enumerated above, including CodonW, GCUA, INCA, and others identifiable by those skilled in the art. Several software packages are available online for codon optimization of gene sequences, including those offered by companies such as GenScript, EnCor Biotechnology, Integrated DNA Technologies, ThermoFisher Scientific, among others known those skilled in the art. Those packages can be used in providing Gvp proteins with codon ensuring optimized expression in various cell systems as will be understood by a skilled person.

A representative example of heterologous GVs is the *E. coli* expressing a heterologous GV gene cluster from *Bacillus megaterium* (Mega). Mega GVs are typically cone-tipped cylindrical structures with a diameter of approximately 73 nm and length of 100-600 nm, encoded by a cluster of eleven or fourteen different genes, including the primary structural protein, GvpA, and several putative minor components and putative chaperones [11, 18] as would be understood by a person skilled in the art.

In some embodiments, the GVs can be engineered to modulate their mechanical, acoustic, surface and targeting properties in order to achieve enhanced harmonic responses and multiplexed imaging to be better distinguished from background tissues. In particular in those embodiments, a GV can be engineered to provide a variant GvpC protein and corresponding variant GV type and/or to provide a variant GV type with a modified amount of native or engineered GvpC protein on the protein shell of the GV.

A GvpC protein is a hydrophilic protein encoded by a gene of the GV gene cluster, which includes repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a GvpC multiple repetitions of a same repeat is flanked by an N-terminal region and a C-terminal region. In a same GvpC, repetitions of a same repeat in the GvpC protein can have different lengths and different sequence identity one with respect to another.

Repeat regions within any given GvpC sequence 'X' from organism 'Y' can be identified by comparing the related sequence with the sequence of a known GvpC (herein e.g. reference GvpC sequence "Z"). In particular the comparing can be performed onby aligning sequence 'X' to the reference GvpC sequence 'Z' using a sequence alignment tools such as BLASTP or other sequence alignment tools identifiable by a skilled person at the date of filing of the application upon reading of the present disclosure. In particular, the reference sequence 'Z' is chosen from a host that is the closest phylogenetic relative of 'Y', from a list of *Anabaena flos-aquae, Halobacterium salinarum, Haloferax medidíterranei, Microchaetae diplosiphon* and *Nostoc* sp. The sequence alignment of 'X' and 'Z' (e.g. a BLASTP) is performed by performing a first alignment of sequence X and sequence Z to identify a beginning and an end of a repeat in 'X as well as a number of repetition of the identified repeat, in accordance with the known repeats in 'Z'. The first alignment results in at least one first aligned portion of X with respect to reference sequence Z. The aligning can also comprises performing a second alignment between the at least one first aligned portion of X identified following the first alignment and additional portions of X to identify at least one repeat 'R1' in X. Other repeats in 'X' (i.e. R2, R3, R4 . . . ) can subsequently be identified with respect to R1.

In performing alignment steps sequence are identified as repeat when the sequence show at least 3 or more of the following characteristics:

1) There are no gaps or spacer amino acids between any two adjacent repetition of a repeat (see e.g. FIGS. 16A-16E and FIGS. 26A-26H)
2) Each repetition of a repeat has a sequence length between 18-45 amino acids, e.g. 33 amino acids seen for 100% of the repeats in *Anabaena flos-aquae, Microchaetae diplosiphon* and *Nostoc* sp. (e.g. FIGS. 26A-26H)
3) Upon alignment of all the repeats within a given GvpC sequence, there exists for every position in more than 50% of the total number of repeats, greater than 50% sequence similarity of the amino acid residues in each repeat (e.g. FIGS. 26A-26H)
4) Sub-sequences of at least 3 or more amino acids at the beginning or end of the that are conserved across 50% or more of the repeats in a given GvpC sequence, also referred to as "consensus sequences". Exemplary embodiments of such consensus sequences are QAQELLAF (SEQ ID NO:32) at the end of repeats in *Anabaena flos-aquae*, LHQF (SEQ ID NO:33) at the end of repeats in *Microchaete diplosiphon*, LSQF (SEQ ID NO:34) at the end of repeats in *Microcystis aeruginosa* and DAF at the beginning of repeats in *Halobacterium salinarum*. (e.g. FIGS. 16A-16E and 26A-26H).
5) The consensus sequence of all the repeats within a given GvpC sequence show greater than 60% percent identity to the consensus sequence of all the repeats within another GvpC from a different microbial host of the same phylogenetic order (e.g. FIGS. 26G-26H).

In some exemplary embodiments, the repeat has at least 90% sequence identity with another repeat within the same GvpC sequence.

In a GvpC the N-terminal region comprises the amino acid residues upstream (towards the N-terminus) of the first repeated sequence of the GvpC's repeat, while the C-terminal region comprises the amino acid residues downstream (towards the C-terminus) of the last repeated sequence of the GvpC's repeat.

GvpC protein is typically rich in glutamine, alanine and glutamic acid residues, which account for >40% of the residues. In the exemplary *Anabaena flos-aqaue*, GvpC comprises five highly conserved 33-amino acid repeats with predicted alpha-helical structure, and is believed to bind across GvpA ribs to provide structural reinforcement [3], which aligns with experimental data. In biochemical studies, removal of GvpC and truncations to its sequence were shown to result in a reduced threshold for Ana GV collapse under hydrostatic pressure. In addition, previous studies in other species have demonstrated that GvpC can tolerate fusions of bacterial and viral polypeptides.

GvpC sequences in different bacteria or archaea producing GVs typically have a greater than 15% sequence identity and are produced by genes found in the gas vesicle gene cluster.

In some embodiments, a GV can be engineered to tune the related acoustic properties. In particular the engineering can be performed by genetically engineering a GV having an acoustic collapse pressure $aP_0$ performed to obtain a variant GV with a critical collapse pressure $aP_1$ lower than the $aP_0$.

In particular, in some embodiments, a method to tune acoustic properties of a gas vesicle protein structure having a critical collapse pressure $aP_0$ comprises engineering the GV by replacing a GvpC protein of the GV's protein shell with: subsaturated concentrations of the GvpC protein and/or saturated or subsaturated concentrations of a genetically modified GvpC protein.

In some of those embodiments, the GvpC proteins of the native GVs are removed with methods and techniques identifiable to a skilled person. For example, the native GvpC proteins can be removed by treating the GVs with urea, as shown in Example 1 and FIG. 2D, which results in GVs with their outer GvpC layer stripped but leaves the GvpA-based shell intact.

In some embodiment of methods to tune the acoustic properties of a GV, a GvpC protein of a set type GV can be replaced by wild-GvpC or genetically modified GvpC variants in certain concentrations either sub-saturating or saturated, such that complete surface coverage of the gvpA shell and gas vesicle strengthening does not occur.

In particular, in some embodiments, adding molar excess of gvpC:gvpA than that found in native GVs prior to dialysis to produce GVs can increase $aP_1$ up to a threshold, above which the critical collapse pressure plateaus and does not increase any further (see FIG. 5, FIG. 6 and FIG. 17). Such concentration is considered as a saturated concentration. Conversely, in some embodiments, adding a lower molar ratio of gvpC:gvpA prior to dialysis to produce GVs can decrease $aP_1$.

In some embodiment of methods to tune the acoustic properties of a GV, the genetically modified GvpC protein of methods and systems can be modified by at least one of a) a deletion of the N-terminal region, C-terminal region or both
b) a deletion of 3 or more repeats, in particular starting from the repeat adjacent to the C-terminus and moving towards the N-terminus
c) a deletion of at least one repeat immediately after the N-terminus, and
d) addition of amino acids such as functional tags
e) substitution of a sub-sequence comprising at least nine amino acids within the GvpC sequence, wherein the substitution refers to replacement of amino acids in the original GvpC sequence with any other amino acid sequence, particularly with other amino acid sequence having sequence similarity lower than 50% with respect to the sub-sequence within the GvpC sequence, to obtain a gas vesicle variant with a critical collapse pressure aP1 lower than the $aP_0$.

In some embodiments, a deletion can comprise a deletion of up to all of the amino acids of an N-terminal region, one or more repeat regions, or a C-terminal region. In some embodiments, a deletion can comprise a deletion of part of one or more of an N-terminal region, a C-terminal region, or a repeat region. For example, a deletion can comprise part of region 2 and part of repeat region 3, as shown in the Examples (exemplary variant N-rep2to3-C). In some embodiments, a deletion can comprise a deletion of more than one repeat region.

In some embodiments, a deletion of a gvpC N-terminal region or a C-terminal region can produce a gvpC variant comprised in a GV having a lower $aP_1$ than a deletion of a gvpC repeat region.

In some embodiments, a deletion of a gvpC N-terminal deletion can produce a gvpC variant comprised in a GV having a lower $aP_1$ than a deletion of a gvpC C-terminal deletion.

In some embodiments, a deletion of both a gvpC N-terminal region and a gvpC C-terminal region can produce a gvpC variant comprised in a GV having a lower $aP_1$ than a deletion of a gvpC N-terminal region or a C-terminal region performed individually.

In some embodiments, a deletion of one or more repeats regions that are in a position further towards the gvpC N-terminus can produce a gvpC variant comprised in a GV having a lower $aP_1$ than a deletion of one or more repeats regions that are in a position further towards the gvpC C-terminus.

In some embodiments herein described, GV variants without GvpC proteins or with truncated or mutated GvpC proteins exhibit lower collapse pressure compared to the native GVs under both hydrostatic pressure and ultrasound (Example 2).

For example, the native Ana GVs have a hydrostatic collapse pressure about 569.85 kPa, while the Ana GV variants free of GvpC proteins and the Ana GV variants with truncated GvpC proteins have a hydrostatic collapse pressure about 195.30 kPa and 374.30 kPa, respectively (see Table 5). The native Ana GVs have an acoustic collapse pressure about 868.81 kPa, while the Ana GV variants free of GvpC proteins and the Ana GV variants with truncated GvpC proteins have a hydrostatic collapse pressure about 571.00 kPa and 657.04 kPa, respectively (see Table 7).

In some embodiments, GV variants without GvpC proteins or with truncated or mutated GvpC proteins show harmonic signals several-fold higher than the native GVs both in vitro and in vivo.

As used herein, the term "harmonic signal" or "harmonic frequency" refers to a frequency in a periodic waveform that is an integer multiple of the frequency of the fundamental signal. In addition, this term encompasses sub-harmonic signals, which are signals with a frequency equal to an integral submultiple of the frequency of the fundamental signal. In ultrasound imaging, the transmitted pulse is typically centered around a fundamental frequency, and received signals may be processed to isolate signals centered around the fundamental frequency or one or more harmonic frequencies. In relation to the imaging of GVs, for those natural or modified GVs that are capable of producing harmonic scattering at a particular acoustic pressure, isolating received harmonic signals during imaging can improve the fraction of the image signal that is due to the GVs rather than background scattering and reflection. Exemplary GV variants showing show harmonic signals several fold higher than the native GVs comprise GV variants such as ΔGvpC, ΔN&C-term, ΔN-term, ΔC-term, SR1, SR3, ST-GvpC, GvpC-R8, GvpC-RGD, GvpC-LRP, GvpC-mCD7, SR1CERY1, SR3CERY1, ΔN&C-CERY1, WTCERY1, GvpC-ACPP, GvpC-hPRM, N-term-rep1to2-C-term, Nterm-rep1to3-C-term, N-term-rep2to3-C-term and N-term-rep1to4-C-term. FIGS. 10A-10H show exemplary genetic engineering of GV surface properties, cellular targeting and multimodal imaging. As shown in FIGS. 10A-10H, gvpC genetic fusions can be used to engineer novel GV properties and functions. FIGS. 11A-11C show an exemplary Clustal Omega sequence alignment of exemplary genetically engineered GvpC proteins described herein.

The term "fundamental signal" or "fundamental wave" refers to the primary frequency of the transmitted ultrasound pulse. All GVs can backscatter ultrasound at the fundamental frequency, allowing their detection by ultrasound.

The term "non-linear signal" refers to a signal that does not obey superposition and scaling properties, with regards to the input. The term "linear signal" refers to a signal that does obey those properties. One example of non-linearity is the production of harmonic signals in response to ultrasound excitation at a certain fundamental frequency. Another example is a non-linear response to acoustic pressure. One embodiment of such a non-linearity is the acoustic collapse profile of GVs, in which there is a non-linear relationship between the applied pressure and the disappearance of subsequent ultrasound contrast from the GVs as they collapse. Another example of a non-linear signal that does not involve the destruction of GVs, is the increase in both fundamental and harmonic signals with increasing pressure of the transmitted imaging pulse, wherein certain GVs exhibit a super-linear relationship between these signals and the pulse pressure. [19]

In some embodiments, the engineered GvpC variants are obtained by further linking the native GvpC protein to one or more other proteins, polypeptides, or domains to form a recombinant fusion protein.

Recombinant fusion proteins can be created artificially using recombinant DNA technology identifiable by a person skilled in the art of molecular biology. In general, the methods for producing recombinant fusion proteins comprise removing the stop codon from a cDNA or genomic sequence coding for the native GvpC protein having a SEQ ID NO:2 or a derivative thereof, then appending the cDNA or genomic sequence of the second protein in frame through ligation or overlap extension PCR. Optionally, PCR primers can further encode a linker of one or more amino acids residues and/or a PCR primer-encoded protease cleavage site placed between two proteins, polypeptides, or domains or parts thereof. The resulting DNA sequence will then be expressed by a cell or other protein expression system as a single protein. A fusion protein can also comprise a linker of one or more amino acids residues, which can enable the proteins to fold independently and retain functions of the original separate proteins or polypeptides or domains or parts thereof. Linkers in protein or peptide fusions can be engineered with protease cleavage sites that can enable the separation of one or more proteins, polypeptides, domains or parts thereof from the rest of the fusion protein. Other methods for genetically engineering these recombinant fusion proteins include Site Directed Mutagenesis (e.g. using Q5 Site-Directed Mutagenesis Kit from NEB or the QuickChange Lightning Kit from Agilent), Gibson Assembly (e.g. using the NEB Hi-Fi DNA Assembly Kit), Error-prone PCR (e.g. Mutazyme from Agilent) and Golden-Gate assembly (e.g. using the NEB Golden Gate Assembly Mix).

In some embodiments, the gvpC proteins described herein can be synthesized using cell-based methods or cell-free methods known to those skilled in the art. Protein biosynthesis can be performed by translation of DNA polynucleotides encoding the protein. Thus, protein biosynthesis can be performed by providing cell-based or cell-free protein translation systems with DNA polynucleotides encoding the protein. Plasmids with genetically engineered gvpC constructs described herein can be transformed into competent cells, such as BL21(DE3) cells (Invitrogen, Carlsbad, CA) or Rosetta™ (DE3)pLysS cells (Millipore Sigma, Temecula, CA) using electroporation, heat shock, and other methods known to those skilled in the art and expressed in culture. The gvpC proteins described herein can also be produced by liquid-phase or solid-phase chemical protein synthetic methods known to those skilled in the art [16].

In some embodiments, a gvpC variant can be produced by engineering a gvpC protein from any species that encodes a gvpC protein in its genome, or a synthetically designed gvpC protein. In some embodiments, a gvpC protein is a gvpC protein from *Anabaena flos-aquae, Halobacterium salinarum, Halobacterium mediterranei, Microchaete diplosiphon* or *Nostoc* sp., or homologs thereof, and others identifiable by a skilled person.

In some embodiments of methods and systems and related compositions herein described one or more GVs (including variants GVs) can be engineered to include tags peptides and/or functional group to provide the GV with additional functionalities. In particular in some embodiments GVs can be functionalized through genetic and/or chemical modification of a Gvp protein (including variants GvpC protein herein described).

In particular, some embodiments here described tags and/or functional groups can be added through chemical or genetic modification of a GvpC protein or a variant thereof in accordance with the present disclosure of a set type of GV and/or through chemical modification of another Gvp protein of the set type GV.

Reference is made to FIG. 1 showing exemplary GvpC proteins engineered to include tags and/or functional groups. In particular, in the illustration of FIG. 1, the helical structure (3) connected to one of the GvpC proteins represents a genetically or chemically fused protein functionality that is not present in wild-type gas vesicles. The spherical bulb (4) connected to another GvpC represents a genetically or chemically fused fluorescent molecule allowing the gas vesicle to be imaged with both ultrasound and an optical imaging modality such as fluorescence imaging.

In some embodiments, functionalization of a Gvp protein can be performed by reacting one or more GVs with one or more compounds to allow attachment and presentation of a functional group on the protein shell of the one or more GVs.

The term "functional group" as used herein indicates specific groups of atoms within a molecular structure that are responsible for the characteristic chemical reactions of that structure. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, the first functional group and the second functional group can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

The term "present" as used herein with reference to a compound or functional group indicates attachment performed to maintain the chemical reactivity of the compound or functional group as attached. Accordingly, a functional group presented on a GV shell and/or a Gvp protein thereof, is able to perform under the appropriate conditions the one or more chemical reactions that chemically characterize the functional group.

In some embodiments, the functionalization of the GvpC can be performed by chemical conjugation to a GvpC protein shell of moieties such as lysine residues and/or amine-reactive crosslinkers such as sulfo-N-hydroxysuccinimide esters (Sulfo-NHS). Depending on the application, the desired extent of labeling can be tuned by varying the molar ratio of Sulfo-NHS to GVs and by changing the incubation time as will be understood by a skilled person. Additional, chemical moieties including polymers (e.g. polyethylene glycol), fluorophores and small molecules (e.g. biotin) which can be conjugated methods identifiable. Biotinylated GVs can subsequently react with streptavidin or avidinated antibodies[20]. Either dialysis or buoyancy purification can be used to separate the labeled GVs from excess reactants.

In some embodiments methods to functionalize GVs can be performed by genetically engineering a GvpC protein of the GV shell to include one or more protein tags.

The term "tag" as used herein means protein tags comprising peptide sequences introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag. The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags comprise the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO:11)); Calmodulin-tag, a peptide that can be bound by the protein calmodulin (KRRWKKNFIAVSAANRFKKISSSGAL (SEQ ID NO:12)); polyglutamate tag, a peptide binding efficiently to anion-exchange resin such as Mono-Q (EEEEEE (SEQ ID NO:13)); E-tag, a peptide recognized by an antibody (GAPVPYPDPLEPR (SEQ ID NO:14)); FLAG-tag, a peptide recognized by an antibody (DYKDDDDK (SEQ ID NO:15)); HA-tag, a peptide from hemagglutinin recognized by an antibody (YPYDVPDYA (SEQ ID NO:16)); His-tag, typically 5-10 histidines that can be bound by a nickel or cobalt chelate (HHHHHH (SEQ ID NO:17)); Myc-tag, a peptide derived from c-myc recognized by an antibody (EQKLISEEDL (SEQ ID NO:18)); NE-tag, a novel 18-amino-acid synthetic peptide (TKENPRSNQEESYDD-NES (SEQ ID NO:19)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO:20)); SBP-tag, a peptide which binds to streptavidin (MDEKTTGWRGGHVVEGLAGELEQLRAR-LEHHPQGQREP (SEQ ID NO:21)); Softag 1, for mammalian expression (SLAELLNAGLGGS (SEQ ID NO:22)); Softag 3, for prokaryotic expression (TQDPSRVG (SEQ ID NO:23)); Strep-tag, a peptide which binds to streptavidin or the modified streptavidin called streptactin (Strep-tag II: WSHPQFEK (SEQ ID NO:24)); TC tag, a tetracysteine tag that is recognized by FlAsH and ReAsH biarsenical compounds (CCPGCC (SEQ ID NO:25)); V5 tag, a peptide recognized by an antibody (GKPIPNPLLGLDST (SEQ ID NO:26)); VSV-tag, a peptide recognized by an antibody (YTDIEMNRLGK (SEQ ID NO:27)); Xpress tag (DLYDD-DDK (SEQ ID NO:28)); Covalent peptide tags such as: Isopeptag, a peptide which binds covalently to pilin-C protein (TDKDMTITFTNKKDAE (SEQ ID NO:29)); Spy-Tag, a peptide which binds covalently to SpyCatcher protein (AHIVMVDAYKPTK (SEQ ID NO:30)); SnoopTag, a peptide which binds covalently to SnoopCatcher protein (KLGDIEFIKVNK (SEQ ID NO:31)). In embodiments described herein, any of the tags of SEQ ID NO:11-31, and other tags known to those skilled in the art, can comprise one or more amino acid substitutions, insertions, or deletions that do not alter the function of the tag, and can further comprise one or more additional amino acids, up to a maximum tag length of 100 amino acids In some embodiments, the protein tag can be a polyhistidine tag. A polyhistidine-tag is an amino acid motif in proteins that typically consists of six histidine (His) residues typically, often at the N- or C-terminus of the protein. It is also known as hexa histidine-tag, 6×His-tag, His6 tag and by the trademarked name His-tag (registered by EMD Biosciences). The total number of histidine residues can vary in the tag. N- or C-terminal his-tags can also be followed or preceded, respectively, by a suitable amino acid sequence that facilitates a removal of the polyhistidine-tag using endopeptidases. This extra sequence is not necessary if exopeptidases are used to remove N-terminal His-tags (e.g., Qiagen TAGZyme). Polyhistidine-tagging can be used to detect protein-protein interactions in the same way as a pull-down assay. Fluorescent hexahistiadine CyDye tags are also available. These use Nickel covalent coordination to EDTA groups attached to fluorophores in order to create dyes that attach to the polyhistidine tag. This technique has been shown to be effective for following protein migration and trafficking. This technique may also be effective in order to measure distance via Fluorescent Resonance Energy Transfer.

In embodiments described herein a GvpC or a variant gvpC can be engineered to attach a tag fused to or inserted into an N-terminal region, a C-terminal region of a gvpC or a variant gvpC. In some embodiments, a tag that can be used for affinity purification of the engineered gvpC, such as a His-tag. In some embodiments, the tag comprises one or more functional groups that can be used to alter the surface charge of a GV, such as a lysine-rich protein (LRP). In some embodiments, a tag comprises a moiety that can be used for targeting a GV to a cell, such as a receptor-targeting peptide RGD, which binds effectively to a wide range of integrins. In some embodiments, a tag comprises a functionalized moiety that can be used to increase or decrease uptake of GVs by macrophages, such as a CD47 or an R8, respectively. In some embodiments, a tag can comprise a functionalized moiety that can be used for modular approaches in which the GV surface can be specifically covalently conjugated to other recombinant proteins, such as a SpyTag-SpyCatcher.

In some embodiments, engineering of a GvpC to attach one or more tags can be performed with or without substantially alter the critical collapse pressure of the base GvpC.

For example in some embodiments described herein, a GvpC protein of a GV can be engineered to attach one or more protein tags or polypeptide tags while optionally substantially altering the acoustic collapse pressure of a GV shell comprising the engineered GvpC as compared to a GV shell of a same non-engineered GvpC.

The term "substantially alter" or "substantially decrease" as used herein means a decrease of more than 10% in acoustic collapse pressure, preferably more than 20% in acoustic collapse pressure.

In some embodiments described herein, an engineered GvpC protein can comprise one or more protein tags or polypeptide tags. In embodiments described herein, appending functional residues comprising one or more polypeptide tags or protein tags to the N-terminus or the C-terminus of GvpCWT can reduce collapse pressure depending on the length and exact properties of the amino acid sequence.

In particular, in some embodiments, engineering of a GvpC can be further engineered to attach one or more tags up to the C-terminus without substantially alter the critical collapse pressure as compared to deleting the N- and/or C-terminal regions. In some embodiments, small tags such as RGD and RDG do not substantially alter the collapse pressure value. In some embodiments, tags comprising longer sequences such as LRP (100 residues) decrease acoustic collapse pressure to a greater extent. In some embodiments, tags such as those comprising mCD47 cause a substantial decrease in acoustic collapse pressure value. In some embodiments, appending a His-Tag (e.g. 6 His amino acids) to the N-terminus of the wild-type GvpC sequence does not substantially alter the acoustic collapse pressure value. In some embodiments, appending a gvpC with a Spytag-Spycatcher (FIG. 12) is an effective method to functionalize GVs with large molecules (greater than 100 amino acids in length) such as fluorescent proteins, without substantially altering their collapse pressure value.

Addition of a functional moiety comprised in a tag to a gvpC or a variant gvpC can be obtained through different approaches identifiable by a skilled person.

For example, in some embodiments, an addition of a tag to a gvpC or variant gvpC can be performed at a protein level by first providing the gvpC protein or variant gvpC protein and the protein tag and then performing the insertion into a N-terminal or a C-terminal region by breaking a peptide bond between two adjacent amino acids of the gvpC or variant gvpC N-terminal region of C-terminal region and then forming new peptide bonds between the gvpC or variant gvpC and the protein tag, as described above. For example, the gvpC or variant gvpC can be digested with a protease to break a peptide bond between two adjacent amino acids in the gvpC or variant gvpC N-terminal region or C-terminal region, followed by insertion of the protein tag between the previously adjacent amino acids of the N-terminal region or C-terminal region, for example using native chemical ligation methods known to those skilled in the art [21]. In other embodiments, a protein tag can be fused to a C-terminus or an N-terminus of a gvPC protein or a variant gvpC protein using native chemical ligation methods known in the art.

In some embodiments, a tagged gvpC or variant gvpC functionalized with a protein tag inserted or fused to the N- or C-terminus can be synthesized as single protein by design. Proteins can be synthesized using biosynthetic methods, such as cell-based methods or cell-free methods known to those skilled in the art. Protein biosynthesis can be performed by translation of DNA or RNA polynucleotides encoding the protein. Thus, protein biosynthesis can be performed by providing cell-based or cell-free protein translation systems with DNA or RNA polynucleotides encoding the protein. For example, protein biosynthesis can be performed in cells transfected with in vitro transcribed RNA encoding the protein. Proteins can also be produced by liquid-phase or solid-phase chemical protein synthetic methods known to those skilled in the art [22].

In some embodiments, insertion or terminus fusion of a protein tag to a gvpC or a variant gvpC can be performed at a polynucleotide level through to an in-frame insertion of a protein tag-coding polynucleotide in between two codons in an N- or C-terminal region of a gvpC or a variant gvpC. An in-frame insertion can be performed in several steps, by first providing the gvpC- or variant gvpC-coding and the protein tag-coding polynucleotides and performing the insertion by breaking a bond (typically a phosphodiester bond) between two adjacent nucleotide bases of the first polynucleotide and then forming new bonds between the gvpC-coding polynucleotide and the protein tag-coding polynucleotide. For example, the gvpC coding polynucleotide can be digested with one or more restriction endonucleases and then the protein tag-coding polynucleotide inserted by ligation (e.g., using T7 DNA ligase) into compatible site(s) allowing formation of phosphodiester bonds between the first and second polynucleotide bases. Compatible DNA ligation sites can be "sticky" ends, digested with restriction endonuclease producing an overhang (e.g. EcoRI), or can be "blunt ends" with no overhang, as would be understood by those skilled in the art. A fusion of a polynucleotide encoding a tag can also be ligated to an N- or C-terminus of a gvpC or a variant gvpC polynucleotide by ligation (e.g., using T7 DNA ligase) into compatible site(s).

In some embodiments, the gvpC- or variant gvpC-coding and the protein tag-coding polynucleotides can be provided within a single polynucleotide by design. For example, a tag can be added by inserting the polynucleotide encoding a protein of interest in a plasmid or vector that has the tag ready to fuse at the N-terminus or C-terminus. The tag can be added using PCR primers encoding the tag; using PCR the tag can be fused to the N-terminus or C-terminus of the protein-coding polynucleotide, or can be inserted at an internal location, using internal epitope tagging [23], among other methods known to those skilled in the art. Other methods such as overlap extension PCR and infusion HD cloning can be used to insert a tag at a site between the N-terminus and C-terminus of a protein-coding polynucleotide (see Examples). Optionally, a polynucleotide encoding a 'linker' (such as a sequence encoding a short polypeptide or protein sequence, e.g., gly-gly-gly or gly-ser-gly can be placed between the protein of interest and the tag; this can be useful to prevent the tag from affecting the activity of the protein being tagged.

The choice of the location where a tag is added to a protein sequence depends mainly on the structural and functional features of a protein and the intended downstream methods employing the use of the tag.

In embodiments herein described, the insertion location of a protein tag in a genetically engineered gvpC or variant gvpC is performed at insertion position selected to have the tag presented on the external surface-exposed position of the gvpC or variant gvpC without compromising the function of the gvpC or variant gvpC.

In some embodiments, the GVPS and variants thereof can be used as a contrast agent in the method to provide an ultrasound imaging of a target site. In some embodiments, the GVPS and variants thereof can be used as a contrast agent in the multiplexed ultrasound imaging methods herein described. In particular, a combination of GVPS and/or variants thereof can be used in a contrast agent, each exhibiting a different acoustic collapse profile with progressively decreased midpoint collapse pressure values. In some cases, the percentage difference between the midpoint collapse pressure values of any given two GVPN types in the contrast agent is at least twenty percent.

In some embodiments, one or more of the GVs herein described can be comprised in a composition together with a suitable vehicle. The term "vehicle" as used herein indicates any of various media acting usually as solvents, carriers, binders or diluents for the multi-ligand capture agents that are comprised in the composition as an active ingredient. In particular, the composition including the GVs can be used in one of the methods or systems herein described In some embodiments, one or more of the GVs herein described can be comprised in a contrast agent in the sense of the disclosure, the contrast agent comprising a plurality of the GVs (inclusive of engineered GVs) and/or GvpC variants herein described. The term "contrast agent" refers to an agent (material) in aqueous media, including water, saline, buffer, liquid media, configured to increase contrast in ultrasound imaging methods. By an increase in contrast, it is meant that the differences in image intensity between adjacent tissues visualized by a ultrasound imaging method are enhanced. For instance, differences in image intensity can be enhanced with the use one or more sets of imaging parameters.

The contrast agent can be provided in any pharmaceutically and/or physiologically suitable liquid or buffer known in the art. For example, the contrast agent can be contained in water, physiological saline, balanced salt solutions, buffers, aqueous dextrose, glycerol or the like. In certain embodiments, the contrast agent can be combined with agents that can stabilize and/or enhance delivery of the contrast agent to the target site. For example, the contrast agent can be administered with detergents, wetting agents, emulsifying agents, dispersing agents or preservatives.

In certain embodiments, two or more gas vesicle types are combined in a mixture for multiplexed imaging, wherein the two or more GV types have distinct acoustic collapse profiles and different biodistribution or targeting properties, such that their location in the imaged specimen provides information about two or more different aspects of the specimen, such that the unmixed ultrasound images acquired after administering this mixture contains information about the two or more different aspects of the specimen. Different aspects of the specimen may include different molecular or cellular targets to which the GVs bind, different vascularization patterns through which GVs flow in circulation, different levels of cellular metabolism leading to uptake or destruction of GVs, etc. These mixtures are supplied together with the acoustic collapse profiles or each component of the mixture and the MIAPs that should be used to acquire multiplexed images.

In certain embodiments, the gas vesicles contained in the contrast agent are bacterially-derived, gas vesicles formed by bacteria, such as photosynthetic bacteria (e.g., cyanobacteria), or archaea-derived gas vesicles formed by archaea (e.g., halobacteria). In other embodiments, the gas vesicles contained in the contrast agent are genetically engineered GVs by genetically engineering the bacterially-derived gas vesicles or archaea-derived gas vesicles herein described.

As mentioned above, the GVs (inclusive of native and variant GVs) and/or GvpC variants herein described can be provided as a part of systems to perform any of the above mentioned methods. The systems can be provided in the form of kits of parts. In a kit of parts, one or more GVs and/or GvpC variants and other reagents to perform the method are comprised in the kit independently. The GVs and/or GvpC variants can be included in one or more compositions, and each GV and/or GvpC variant is in a composition together with a suitable vehicle.

In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (such as. wash buffers and the like).

Further details concerning the engineered GVs, and systems and methods of the present disclosure will become more apparent hereinafter from the following detailed disclosure of examples by way of illustration only with reference to an experimental section.

EXAMPLES

The engineered GVs and related systems and methods herein disclosed are further illustrated in the following examples, which are provided by way of illustration and are not intended to be limiting.

In particular, the following examples illustrate exemplary methods and protocols for preparing exemplary gas vesicles protein structure from Ana, Halo and engineered *E. coli*, and related characterizing testing and use these structure for ultrasound imaging in vivo and in vitro. A person skilled in the art will appreciate the applicability and the necessary modifications to adapt the features described in detail in the present section, to additional gas vesicle protein structure and related methods and systems according to embodiments of the present disclosure. The following materials and methods were used in the experiments illustrated in the Examples.

Transmission electron microscopy GV samples were diluted to $O.D_{PS,500}$~0.2 in 10 mM HEPES buffer containing 150 mM NaCl (pH 8) and spotted on Formvar/Carbon 200 mesh grids (Ted Pella, Redding, CA) that were rendered hydrophilic by glow discharging (Emitek K100X). GV samples were negatively stained using 2% Uranyl Acetate. Images were acquired using the Tecnai T12 LaB6 120 kV TEM equipped with a Gatan Ultrascan 2 k×2 k CCD and 'Leginon' automated data collection software suite.

Pressurized absorbance spectroscopy GV samples were diluted to $O.D_{PS,500}$~0.2 and loaded onto a flow-through, 1 cm path-length quartz cuvette (Hellma Analytics, Plainview, NY) that was connected to a $N_2$ cylinder through a pressure controller (Alicat Scientific, Tucson, AZ). The pressure was increased stepwise in 20 kPa increments up to 1 MPa and the $O.D_{PS,500}$ at each step was measured using a spectrophotometer (EcoVis, OceanOptics, Winter Park, FL). Fully collapsed GV sample was used as the blank.

In vitro ultrasound imaging Imaging phantoms were prepared from 1% agarose in PBS. Two times concentrated GV samples were mixed 1:1 with melted 1% agarose at 50° C., and 100 µL of the mixture was quickly loaded into the phantom wells. Imaging was performed using a Verasonics Vantage programmable ultrasound scanning system. The L11-4v or L22-14v 128-element linear array transducers (Verasonics, Kirkland, WA) were used for image acquisition, with a pitch of 0.3 mm or 0.1 mm and elevation focus of 15-20 mm or 6 mm respectively. The phantom was placed on a custom 3-D printed holder and the transducer was mounted on a computer-controlled 3-dimensional translating stage (Velmex, Inc., Bloomfield, NY). During imaging, the transducer was immersed in PBS at an elevation that positioned the focal zone of the ultrasound beam at the center of the sample well. All images were acquired using a conventional B-mode sequence with 128 ray lines.

The acoustic multiplexing and collapse spectrum measurements were obtained by using GV samples at a final OD of 1 and a transmit frequency of 6.25 MHz on the L11-4v, with a 4 cycle pulse and transmit focus of 20 mm, F-number 2 and persistence 90. The images were acquired at a transmit voltage of 1.6 V. To collapse GVs, acoustic pressure was delivered to the specimen by lowering the F number to 0.1 and ramping up the voltage gradually. At each collapse step, the transducer was translated in the y and z planes to ensure homogenous GV collapse over the entire well.

Non-linear imaging experiments were performed using the L11-4v transducer with a transmit frequency of 4.46 MHz and receive filtering using a 2 MHz band pass around 4.46 MHz and 8.92 MHz for the fundamental and second harmonic signals, respectively. GV samples at OD 2.5 were imaged at 2.5 V and F-number 3 using a 3 cycle pulse and a persistence of 90.

In vivo ultrasound imaging Intravenously injected gas vesicles were imaged in 5-7 weeks old female SCID mice using the L11-4v transducer. To be consistent with in vitro experiments, a transmit frequency of 4.46 MHz and reception frequencies of 4.46 MHz and 8.92 MHz were used for the fundamental and non-linear imaging respectively. Imaging was done at 2.5 V using a 3 cycle pulse at an F-number 3 and persistence of 20. The mice were maintained under isofluorane anesthesia on a heated imaging platform. Images were acquired at a rate of 16 frames/sec for ~50 s. A 50 µL volume of gas vesicles at OD 23.5 in PBS was infused ~5 s after the start of the experiment at a flow rate of 0.3 ml $min^{-1}$. Between sample injections, a 10 s high-power burst from the transducer was used to completely collapse any residual GVs in circulation.

Image analysis MATLAB and ImageJ (NIH, Bethesda, MD) were used to process in vitro and in vivo ultrasound data. Regions of interest (ROIs) were manually defined so as to capture signals from the entire sample well or the IVC. ROI dimensions were preserved between different GV samples and the mean intensity per pixel calculated using all pixels within the ROI. Quantification of in vitro harmonic and fundamental GV signals was performed by subtraction of the post-collapse images from the pre-collapse images. In vivo IVC signals were analyzed for all acquired frames over the 50 s imaging window and smoothed infusion time-course curves were generated using locally weighted scatterplot smoothing. Area under the curve (AUC) values were obtained from the raw data normalized to the pre-infusion baseline. Acoustic spectral unmixing was performed using MATLAB after applying a spectral averaging filter with a kernel size of [20 20] pixels to reduce out-of-well noise. Pseudocolor assignments and merging of spectrally unmixed images were performed using ImageJ (greyscale converted representations of color maps are shown next to the images in FIG. 4G).

Zeta potential measurements Zeta potential of GVs with WT-GvpC and GvpC-LRP were measured using Brookhaven Instruments Corporation Zeta-PALS instrument (Hotsville, NY). 40 µL of GVs (in PBS) were added to 1.5 mL of double distilled water at a final concentration of 35 pM and conductance of 1 mS. Electrodes were placed in the cuvette with the samples and average zeta potential for each run was determined from 10 measurements.

In vitro characterization of functionalized GVs Alexa-488 succinimidyl ester fluorescent dye (Invitrogen, Carlsbad, CA) was reacted with GVs in PBS for 2 hours at 10,000:1 molar excess of dye to GVs. Excess succinimidyl ester was quenched with 10 mM Tris. Fluorescently-labeled GVs were purified using dialysis against PBS. Cells were seeded on 22×22 mm coverglass and cultured for 24 hours prior to the start of the experiments. Due to the buoyant nature of GVs, in vitro characterization was carried out using modified 6-well plates that contain 3 pegs to enable inverted cell growth (facing down). For receptor (avP3) targeting experiments, 16 µL of fluorescently-labeled GVs (GvpC$_{WT}$, GvpC$_{WT}$-RGD, and GvpC$_{WT}$-RDG) at 1.2 nM were added to U87 cells (ATCC Manassas, VA) and incubated for 24 hrs. To test phagocytic uptake using GvpC$_{WT}$, GvpC$_{WT}$-mCD47, and GvpC$_{WT}$-R8, 8 µL of fluorescently-labeled GVs at 1.2 nM were added to RAW 264.7 cells (ATCC). After the allotted GV incubation, cells were washed 3× with PBS, fixed with 4% paraformaldehyde, and mounted with DAPI containing mounting media. Confocal fluorescence images were acquired using inverted Zeiss LSM 710 NLO (Thornwood, NY) using a 20× objective.

SpyTag—SpyCatcher functionalization of Ana GVs SpyTag-Ana GVs were prepared using the re-addition protocol described above. SpyCatcher-mNeonGreen (SC-mNG) was expressed and purified from BL21 E. coli using non-denaturing Ni-NTA purification. ST-GVs (OD:5-10) were incubated with SC-mNG at a 2× molar excess of SpyCatcher: SpyTag in PBS for 1 h at room temperature. GVs were spun at 300 g for 4 hours twice in order to remove excess unbound protein; the supernatant containing GVs was resuspended in fresh PBS.

ST-GV (±SC-mNG) and WT-GV (+SC-mNG) samples were prepared in a 1% agarose phantom at final OD 2.5 and imaged with the Verasonics L22-14V transducer at 19 MHz, 5.0V and F-Number 3 with a persistence of 90. The agarose phantom was also imaged through the green channel of a BioRad Chemidoc MP system (Hercules, CA). The fluorescence intensity of the ST-GV (±SC-mNG) and WT-GV (+SC-mNG) samples was determined by first collapsing the samples and then measuring fluorescence intensity (ex 506 nm, em 550 nm) in a Molecular Devices SpectraMax M5 plate reader (Sunnyvale, CA).

Example 1: Overview of Exemplary Procedure to Express and Purify GVs

A detailed exemplary optimized protocol is illustrated to express and purify GVs and quantify, optionally functionalize and genetically engineer them, characterize their size and shape, and use them as contrast agents for non-invasive imaging applications.

The procedure begins with isolation of GVs from cultures of Ana and Halo, or from E. coli expressing a heterologous GV gene cluster from Bacillus megaterium (Mega)[18]. This results in three structure populations with distinct properties (see Example 2 and Table 1).

These GVs are then quantified and characterized using pressure-dependent spectroscopy, dynamic light scattering (DLS) and transmission electron microscopy (TEM).

Protocols for modification and functionalization using genetic and chemical approaches are provided as an added option based on the desired end application. Finally, the GVs are imaged in vitro and in vivo using ultrasound and in vitro using HyperCEST MRI.

Example 2: Experimental Design

Key experimental parameters for each stage of the protocol are taken in consideration in performing an experimental design to produce a GV for ultrasound imaging. One important initial consideration is the choice of GV-producing species. Different of GV-producing microorganisms provide GVs with different characteristics which affect the related use as contrast in ultrasound imaging.

Although this protocol presents methods for producing three different types of GVs—Ana, Halo and Mega—one of these types may be most appropriate for a given application (see Table 1).

TABLE 1

Characteristics of different types of GVs

| | Ana GV | Halo GV | Mega GV |
|---|---|---|---|
| Host/origin | Anabaena flos-aquae | Halobacteria salinarum | Heterologous expression of a gene cluster from Bacillus megaterium in E. coli. |
| Shape | Cylindrical | Spindle | Cylindrical |
| Resistance to pressure-induced collapse | Medium (can be tuned) | Low | High |
| Ultrasound contrast | High Nonlinear after engineering | High Nonlinear | Low |
| Stability in Xe-MRI phantoms | High | Low | High |
| Ease of genetic modification | High | Low | Not established |

For example, for ultrasound, unmodified Halo GVs can be used directly in ultrasound imaging to obtain non-linear signals [20, 24]. Ana GVs are a system of choice if one wishes to genetically tune the properties of GVs for multiplexing, multimodal imaging and targeting applications [1, 25]. Mega GVs produce lower echogenicity under ultrasound compared to Ana and Halo GVs, but have a higher critical collapse pressure that can make them useful for multiplexing.

Halo GVs produce non-linear ultrasound contrast immediately after purification, while Ana GVs require a chemical treatment. With regard to Xe-MRI, Ana and Mega GVs are more stable under pressure and during the bubbling of hyperpolarized xenon compared to Halo GVs[26]. All three species have a unique chemical shift in Xe-MRI, allowing multiplexing

Example 3: Production of GVs from Ana and Halo or Heterologously Expressing E coli GVs are obtained from Ana, Halo or heterologously-expressing *E. coli*. Ana is cultured in low-salinity medium supplemented with trace metals and buffering agents, while Halo is cultured in high salinity medium for GV production.

Ana and Halo cultures natively produce ample GVs after a few weeks of growth[1, 20, 25]. Ana cultures additionally require a controlled gaseous environment and illumination for optimal growth. As understood by those skilled in the art, typically, a freshly inoculated culture of cells may require several rounds (typically 2-3) of subculture to become strongly proliferative. The confluent culture of microbes can then be transferred to a separatory funnel that is left undisturbed for up to a week to allow the buoyant cells producing GVs to float to the top and separate from media. Buoyant cells are then lysed using hyper-osmotic shock for Ana and hypo-osmotic shock for Halo. Subsequently, centrifugally assisted floatation can be used to isolate GVs from the cell lysate to yield a concentrated, milky-white solution of GVs in the buffer of choice[1, 20, 25]. Heterologous production of Mega GVs in *E. coli* can be accomplished by expression from a plasmid encoding a Mega GV gene, followed by detergent-mediated lysis[26].

The procedures leading from inoculation of GV-producing microbes to harvesting and purification is summarized in the Table 9, along with important parameters that affect processing time, yield and quality.

TABLE 9

Experimental Parameters for GV Production, Purification and Storage

| Procedure | Design Parameters |
| --- | --- |
| Inoculation of starter culture | Type of culture (suspension vs. solid), amount of inoculum, total volume of culture |
| Growth of starter culture | Temperature, rotation speed, duration, illumination |
| Sub-culturing | Number of flasks, volume of culture and media |
| Harvesting of GVs | Composition of lysis buffer and duration of lysis, concentration of cells |
| Purification | Selection of centrifugation speed, type of rotor, tube and syringe needle |
| Storage | Storage temperature, buffer and type of vial/tube |

Growth conditions are chosen to facilitate optimal proliferation of each host strain and GV expression. As understood by those skilled in the art, one variable to keep track of is pressure, since GVs collapse irreversibly at hydrostatic pressures of 50 to 800 kPa, depending on species[3]. For example, the cultures should be grown under mild agitation, as excessive shaking can lead to GV collapse. During centrifugation steps, the hydrostatic pressure generated for a particular g-force on the liquid column of GVs can be calculated, to ensure that it is well below the GV critical collapse pressure. Long-term storage of purified GV stocks should preferably be done in screw-top vials, as microcentrifuge tubes with snap-lock caps may cause GV collapse due to pressurization of the sample while opening or closing the tube.

Example 4: Expression and Purification of Ana GVs

*Anabaena flos-aquae* (Ana) was cultured in Gorham's media supplemented with BG-11 solution (Sigma, St. Louis, MO) and 10 mM $NaHCO_3$ at 25° C., 100 rpm shaking and 1% $CO_2$ under a 14 h light cycle and 10 h dark cycle. Once confluency was reached, the cultures were transferred to sterile separating funnels and the buoyant cells were allowed to float to the top and separate from the spent media over a 48 h period. Ana GVs were harvested by hypertonic lysis of the buoyant cells with 500 mM sorbitol and 10% Solulyse (Genlantis, San Diego, CA). Purification was done by repeated centrifugally assisted floatation followed by resuspension in 1×PBS (Corning, Union City, CA). GV concentration was determined by pressure-sensitive OD measurements at 500 nm ($OD_{PS,500}$). Pre-collapsed GVs prepared by application of hydrostatic pressure in a capped syringe were used as the blank.

Example 5: Expression and Purification of Halo GVs (i) An exemplary method for growing Halo cultures for GV production follows. Aliquot Carolina growth medium in to an autoclaved flask under sterile conditions. (ii) Inoculate Halo cultures under sterile conditions using one of the following methods. (1) scrape a small amount of pink culture from an agar plate to add to the flask as inoculum. (2) Use one to two brine crystals containing Halo for inoculation. (3) Inoculate from a healthy pink liquid starter culture into 250 mL of fresh growth medium. (iii) Grow the culture in an incubator at 42° C. with 100 rpm shaking for ~2 weeks or until the inoculated culture becomes confluent.

(iv) An exemplary method for harvesting Halo GVs follows: Gently pour the culture from the flask into a separatory funnel (pre-sterilized with stopcork in place). Allow the culture to remain undisturbed until a visible ring is formed at the top. This typically takes 4-6 days. (v) Remove as much of the spent media as possible by opening the stopcork, retaining only the buoyant layer of milky-pink cells for lysis. (vi) Using equal volume of TMC lysis buffer (pH 7.5), gently wash the cells stuck on the sides of the funnel and retrieve the cells. The volume of TMC buffer used might be varied depending on the cell density to achieve efficient hypo-osmotic lysis.

(vii) An exemplary method for isolation and purification of Halo GVs from lysate follows: Aliquot ~1.6 mL of cells in 2 mL tubes and spin in a microcentrifuge at 300 g for 4 hours at 8° C. It is critical to close the tubes gently; the pressure wave caused from snapping the lid will collapse a large number of Halo GVs. (viii) At the top of the tube, a mixed layer of Halo GVs (white) and unlysed Halo cells (milky-pink) will be visible. Using a blunt end 18.5 or 21.5 G needle, aspirate the pellet at the bottom of the tubes as well as the pink cell lysate. Take care to limit the amount of floating Halo cells and Halo GVs (white) that are aspirated in to the syringe. (ix) Transfer the GVs and unlysed Halo cells to fresh tubes and bring to 1.6 mL with 1×PBS. Centrifuge tubes at 300 g for 4 hours at 8° C. (x) Repeat steps viii and ix. After each step, the amount of milky-pink buoyant cells will reduce and white Halo GVs will increase. Continue with centrifugally-assisted floatation until all the cells have lysed and there is no evidence of pink cell lysate in the subnatant. (xi) Resuspend the purified GVs in PBS and aliquot the milky white GV solution into screw top vials or microcentrifuge tubes. The aliquoted Halo GVs can be stored for up to one year at 4° C. Avoid freezing and subjecting the tube to mechanical shocks, such as dropping to the ground or snapping the cap, as this may collapse the GVs.

Example 6: Expression and Purification of Mega GVs

An exemplary protocol for heterologous expression of Mega GVs in E. coli follows: Transform 50 μL chemically competent Rosetta™ 2(DE3) pLysS cells using >1 ng of pST39 plasmid containing the pNL29 Mega GV gene cluster [26] by mixing the two components in a 1.5 mL tube and incubating on ice for 30 minutes. Heat shock the tube in a 42° C. water bath for 45 seconds, and put the tube back on ice for a minute. Add 500 μL of SOC outgrowth medium and incubate in a shaker at 37° C. and 250 rpm for 1 hour. (ii) Prepare 3 mL of LB broth containing 1× Ampicillin (100 μg/mL), 1× Chloramphenicol (25 μg/mL) and 1% (wt/vol) glucose in a glass culture tube. Resuspend 300 μL of the transformed E. coli in the broth. Grow the culture in a shaker-incubator at 37° C. and 250 rpm until $OD_{600}$ reaches 0.4-0.6. Make 100 μL aliquots of the culture in sterile tubes, and mix with 100 μL of 50% sterile glycerol. Freeze the tubes at −80° C. as E. coli glycerol stocks. The glycerol stocks can be stored at −80° C. and used for up to 3 months. Note that the GV yield is reduced when using frozen stocks, so fresh overnight transformations are preferred. (iii) Resuspend a tube of the aliquoted glycerol stock in 3 mL LB broth containing 1× Ampicillin, 1× Chloramphenicol and 1% (wt/vol) glucose. Grow the E. coli culture to saturation ($OD_{600}$>4). For fresh transformations, aliquot 500 μL of the transformed E. coli from step (i) into 5 mL of LB broth containing 1× Ampicillin, 1× Chloramphenicol and 1% (wt/vol) glucose. Grow overnight until the culture reaches saturation (~16 hours). (iv) Prepare 100 mL LB broth containing 1× Ampicillin, 1× Chloramphenicol and 0.2% (wt/vol) glucose, and inoculate 1 mL of the saturated E. coli culture into the broth. Grow at 37° C. for ~2 hours until $OD_{600}$ reaches 0.4 to 0.6. Induce the culture by adding 20 μM IPTG (final concentration), and grow at 30° C. for an additional 16-24 hours.

(v) An exemplary protocol for harvesting and purifying Mega GVs from E. coli cultures follows: Split the culture equally into three 50 ml Falcon tubes and spin for 1 hour at 500 g and 25° C. Avoid higher speeds because they may cause collapse of GVs. (vi) Insert a 10 mL syringe with needle to >1 cm below the surface of the solution and withdraw the clear liquid component of the solution. Withdraw the liquid slowly to preserve the thin layer of cells floating at the top of the solution, as well as the pellet at the bottom, both of which contain Mega GVs. (vii) To lyse the cells, add 4 ml SoluLyse-Tris reagent per 50 ml of E. coli culture, 250 μg/ml lysozyme and 10 μg/ml DNAseI. Rotate the tubes for 10 minutes at room temperature and then aliquot 1.5 mL of the solution to 2 mL tubes. Spin samples for 4 hours at 800 g and 8° C. Mix the floating GV layer gently with supernatant and transfer to a clean tube. (viii) Spin the samples for 4 h at 800 g. Use a 3 mL syringe to remove the bottom fraction, which sometimes includes a small pellet. Gently resuspend GVs in 1 mL of PBS. Repeat the spin and wash steps 3 times. GVs are susceptible to desiccation; resuspend GVs immediately after withdrawing the liquid. (ix) Mega GVs are natively clustered. To uncluster them, GV-containing solution is mixed with 10 M urea in a 2:3 ratio to achieve 6 M final urea concentration, and the resulting solution is gently rotated for 30 min. (x) Dialyze GVs overnight in 6-8 kDa MWCO tubing against 4 L of PBS. This step can be omitted for experiments with no stringent requirements for buffer conditions. A white layer of unclustered GVs is at the top of the liquid phase after buoyancy purification, as well as a re-suspended milky-white solution of Mega GVs in the PBS. Mega GVs can be stored for up to one year at 4° C. Avoid freezing and subjecting the tube to mechanical shocks, such as dropping to the ground or snapping the cap, as this may collapse the GVs.

Example 7: Quantification and Characterization of Gas Vesicles Protein Structures by Pressure Dependent Spectroscopy As understood by those skilled in the art, GVs can be quantified and characterized using techniques such as pressure-dependent spectroscopy, dynamic light scattering (DLS) and transmission electron microscopy (TEM), among others.

Figure 15:
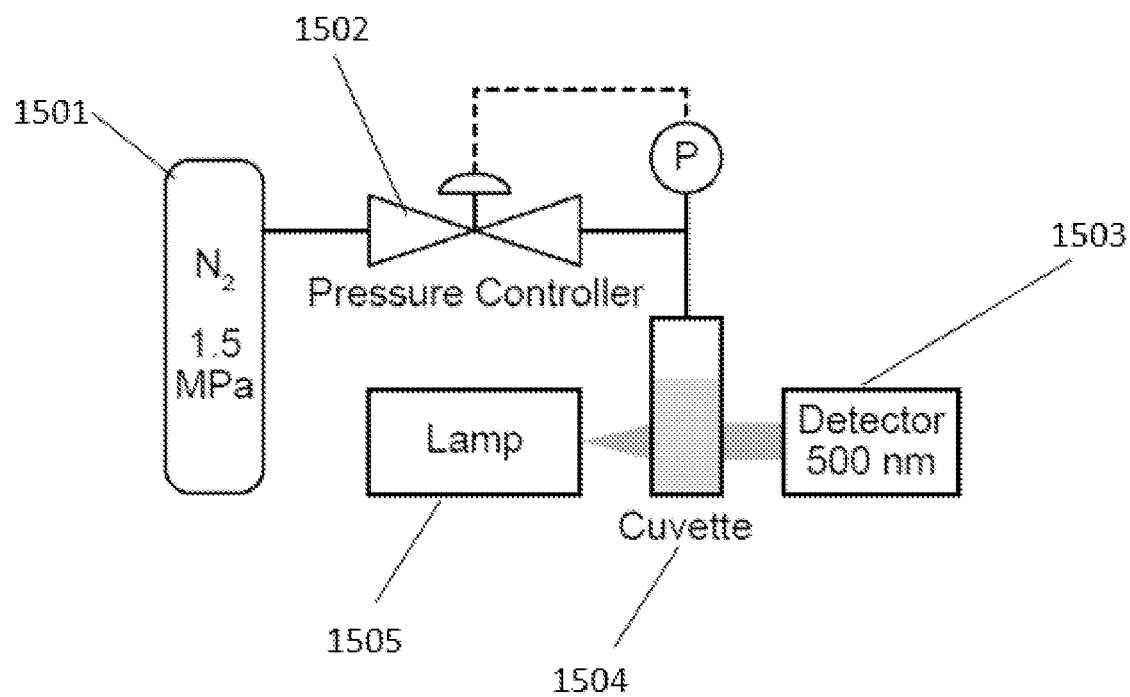
FIG. 15 shows an illustration of an exemplary collapsometry setup used for determining the hydrostatic critical collapse pressure of GVs, wherein 1501 shows a nitrogen cylinder, 1502 shows a pressure controller, 1503 shows an optical density detector set an 500 nm, 1504 shows a cuvette containing GV solution, and 1505 shows a lamp for illumination of the cuvette.

Purified GVs resuspended in a buffer (e.g. phosphate buffered saline, PBS) can be quantified by measuring the optical density at 500 nm, or $OD_{500}$, since GVs scatter visible light. Collapsed GVs (in the same buffer), which do not scatter light, are typically used as the blank control for measurements, yielding a pressure-sensitive OD reading ($OD_{500,\ ps}$). As understood by those skilled in the art, that clustering of GVs, whether by design or due to functionalization with aggregation-prone moieties can potentially confound $OD_{500}$ measurements and contribute to errors in calculating concentration from $OD_{500}$. Pressurized absorbance spectroscopy assays GV mechanical strength by measuring $OD_{500}$ under increasing hydrostatic pressure using a device as shown in FIG. 15.

The concentration of a solution of gas vesicles can be determined by measuring its pressure-sensitive optical density at 500 nm ($OD_{500,ps}$) using a NanoDrop 2000 Spectrophotometer. Load 2 μL of sample on the pedestal for each measurement. Collapsed gas vesicles in the same buffer are used as a blank for measurements. Prepare collapsed GVs by sonication in a water bath until the solution turns completely clear or by manual collapse in a capped syringe. For manual collapse, remove the plunger from a 12 mL Luer-Lock syringe closed with a tip cap and place 5-10 μL of gas vesicle solution at the bottom of the syringe. Making sure that the tip cap is screwed on tight, replace the plunger and push down until there is significant resistance. The increase in pressure will collapse the gas vesicles, turning the milky white solution clear. A shortcut for quick measurements of GV concentration is to blank with the GV resuspension buffer. For most samples, this will give an OD reading that is very close to that measured when using collapsed GVs as a blank. However, for some samples containing GVs that are fluorescent, the collapsed GVs are used as the blank. As would be understood by those skilled in the art, it can be important to ensure that the GVs are homogenously re-suspended in solution just before measurements. For each sample, take the average $OD_{500,ps}$ value after multiple measurements (n>=3) to ensure precision and accuracy.

To characterize the purified GVs, the following exemplary procedure can be used to determine the critical collapse pressure of GVs using pressurized absorbance spectroscopy. Before acquiring measurements, connect the spectrophotometer to a power supply for 30 m to allow it to warm up. Run the Alicat_startup script to initialize the pressure controller. Blank the spectrophotometer with a cuvette filled with PBS or GV resuspension buffer and run OceanOptics_startup_FullTrans to save the data. Establish a zero-transmission baseline with the opaque side of cuvette blocking the light path using the OceanOptics_startup_No-Trans script. Fill cuvette with intact GV sample ($OD_{500\ nm}$=0.2 in PBS) and fasten the cannulae securely. To assist loading, use elongated gel-loading micropipette tips. Open the $N_2$ tank valve, pressure regulator, and pressure controller valve. Run the Collapse script to measure the $OD_{500,ps}$ under increasing hydrostatic pressure (0 kPa-1.4 MPa in 20-kPa increments). Between these measurements, rinse the cuvette with DI $H_2O$, 70% ethanol and acetone to ensure that cuvette is completely clean and dry before adding the next sample. After measurements, close gas the valves and turn off the spectrophotometer.

GV protein concentrations can be measured for example using the Pierce 660 nm protein assay to obtain relationships between optical density and protein content for the GV solutions. The protein concentrations to OD relationships of three types of GVs can be determined, for example as shown in Table 2 below (N=4, 5, 3 for Mega, Ana and Halo GVs respectively and the errors are in SEM). The molecular weight can be derived from the TEM data, assuming a spindle shape for Halo GVs, a cylindrical shape for Mega and Ana GVs, a wall thickness of 18 Å and a protein density of 1.4 g/mL.

TABLE 2

Quantification and calculation of GV molecular weight and molar concentration.

|  | Ana | Halo | Mega |
| --- | --- | --- | --- |
| Protein concentration to $OD_{500}$ ratio ([µg/mL]/OD) | 36.6 ± 2.6 | 13.4 ± 2.2 | 145.5 ± 6.4 |
| Estimated molecular weight (MDa) | 320 | 282 | 71.7 |
| Estimated molar protein concentration to $OD_{500}$ ratio (pM/OD) | 114 | 47.3 | 2,030 |
| Estimated gas fraction to $OD_{500}$ ratio (v/v/OD) | 0.000417 | 0.000178 | 0.000794 |

Additional techniques to quantify and characterize GVs are exemplified in additional examples herein described Example 8: Quantification and Characterization of Gas Vesicles Protein Structures by Dynamic Light Scattering Dynamic light scattering (DLS) can be used to estimate the hydrodynamic size of GVs for routine non-destructive characterization and quality control. DLS can be used to assess GV clustering. As would be understood by those skilled in the art, care should be taken in the interpretation of DLS readings of GVs due to the spherical assumption of the Einstein-Smoluchowski relation and the non-spherical shape of GVs.

An exemplary protocol for preparation of GV specimens for dynamic light scattering (DLS) is as follows: First, dilute the GV samples to $OD_{500,ps}$=0.2 in PBS. Next, measure the particle size on ZetaPALS instrument with an angle of 900 and refractive index 1.33.

Additional protocols would be identifiable by a skilled person upon reading of the present disclosure.

Example 9: Quantification and Characterization of Gas Vesicles Protein Structures by Transmission Electron Microscopy (TEM)

An exemplary protocol for preparation of GV samples for transmission electron-microscopy (TEM) follows: First, buffer-exchange the purified GVs in 10 mM HEPES buffer with 150 mM NaCl or an alternative non-phosphate containing buffer via centrifugally-assisted floatation (same procedure as used for GV isolation) at 8° C. and 300 g. Replace the subnatant with equal volume 10 mM HEPES buffer with 150 mM NaCl. Repeat 3 times. The aim of this step is to prevent phosphate in the PBS from causing unwanted precipitation of the uranyl acetate stain used downstream in step (vi). Therefore, if the GV solution is very concentrated, direct dilution of the GV sample into the above-mentioned HEPES buffer to a final OD of 0.2 would be a quicker alternative. Next, dilute the GVs to a final OD of 0.2. Next, spin 2% Uranyl acetate solution in a benchtop centrifuge at 14,000×g for 5 minutes to pellet any precipitate. Next, charge Formvar TEM grids using the glow discharge system with 15 mA current for 1 minute. Next, place 2 µl of well-mixed GV solution on the charged Formvar TEM grids for 3 minutes.

The sample should be placed on the carbon side of the grid; avoid placing sample on the copper side. For convenience, we use PELCO reverse, anti-capillary tweezers to hold the TEM grid while adding sample and negative stain. Next, add 5 µl of 2% uranyl acetate to the GV solution on the TEM grid for 30 seconds. Next, using a Whatman filter paper, wick the solution by gently touching the edge of the grid. For consistent results, leave a thin film of sample on the grids and leave to air dry. Finally, image the grids using TEM. Standard TEM methods applicable to the present disclosure are known to those skilled in the art.

In particular, negative contrast TEM can be used for imaging GV size, shape, texture and integrity following production and physical or biochemical treatments. Negative staining with uranyl acetate can be used to produce contrast, and use of a buffer such as HEPES is preferred over phosphate buffers that may precipitate with the uranyl acetate. The concentration of the GV solution spotted on the grid directly correlates with the density of GV particles on the grid.

Example 10: Exemplary GV's Engineering: Stripping of Native GvpCs from Ana Gvs

An exemplary protocol for stripping native GvpC off Ana GVs in order to prepare ΔGvpC GVs follows: First, dilute purified Ana GVs in PBS such that $OD_{500,ps}$<10. Next, prepare 3:2 (vol/vol) mix of GV stripping buffer (10M urea in 100 mM Tris buffer) and GV solution in PBS. Pipet 1.7 mL into 2 mL microcentrifuge tubes. Next, centrifuge at 300 g for 4 hours, or until the subnatant is completely clear. Remove the clear subnatant with a syringe using a 21 G flat needle. Retain the milky white supernatant in the tube. Resuspend the GV-containing supernatant in GV stripping Buffer (Round 2 i.e. 6M urea, 60 mM Tris-HCl). Repeat this step 1 time. Next, confirm GvpC removal by performing SDS-PAGE. Incubate a 1:1 (vol/vol) mix of GVs in 2× Laemmli buffer (containing 5% (vol/vol) 2-mercaptoethanol) at 95° C. for 5 m. Centrifuge briefly to collect condensate.

Next, assemble the electrophoresis cell with the comb and tape removed from the polyacrylamide gels. Fill the inner chamber completely with 200 mL 1×TGS buffer. Ensure that the cell is not leaking fluid. Fill the outer chamber up to mark with 600 mL 1×TGS buffer. Next, load the protein ladder and samples in the gel using gel-loading tips. GVs should be at $OD_{500}$>3 prior to the 1:1 dilution. If purified proteins are being run on the same gel for comparison, load >100 ng. In order to prevent contamination between wells, do not exceed the maximum recommended volume per well. Next, connect electrophoresis cell to power supply and run the gel for 55 m at 120V. Next, recover the gel by disassembling the electrophoresis cell and the gel cassette. Incubate the gel in a holder with DI $H_2O$ for 10 m, then stain for 1 h with 10 mL SimplyBlue™ SafeStain. De-stain the gel for at least 1 h with 10 mL DI $H_2O$. Next, image the gel using a Coomassie imaging protocol using the gel imaging system to visualize protein bands. The GvpC band at approximately 25 kDa should be missing.

ΔGvpC GVs can be stored in urea buffer at 4° C. for no more than 1 week. When preparing ΔGvpC GVs for long term storage without any further genetic functionalization or recombinant GvpC addition it can be useful to dialyze the GV solution against PBS in order to completely remove the urea.

Example 11: Exemplary GV's Engineering: Chemical Functionalization of Ana GVs An exemplary protocol for chemical functionalization of GVs follows: As would be understood by those skilled in the art, purified Ana, Halo and Mega GVs contain lysine residues on the surface that can be used to chemically conjugate a variety of moieties such as polyethylene glycol, fluorophores and biotin using an amine-reactive coupling group such as N-hydroxysuccinimide ester. First, measure the concentration of purified GVs using the OD relationships in Table 2. Next, aliquot the NHS-moiety in anhydrous DMSO at 100× of the required molar concentration for the amine-NHS reaction. For Alexa-488-NHS conjugation to Ana GVs, aliquot 5 μl of the 10 mM stock solution of the dye pre-prepared in anhydrous-DMSO. Ensure that the NHS-moiety solution does not contain detergents or surfactants that can affect the integrity and properties of GVs. Next, adjust the concentration and volume of GVs to the desired amount and ensure that the buffer is free of amines (avoid Tris buffer).

For Alexa-488-NHS conjugation to Ana GVs, bring Ana GVs to OD1 in 1 mL of PBS at pH 7.4. If GVs were previously in a buffer containing free amines or PBS with pH less than 7, ensure complete buffer exchange with PBS at pH 7-9 before proceeding with the amine-NHS reaction. Next, add $10^5$ molar excess of the NHS-moiety to GVs, keeping the DMSO concentration at 0.5% or less of the total reaction volume. For Alexa-488-NHS conjugation to Ana GVs, add 5 μl of the 10 mM Alexa-488-NHS in DMSO to 1 mL of Ana GV solution.

Based on the average number of gvpA and gvpC protein monomers that make up Ana GVs, approximately 50,000 lysine residues are present for every Ana GV. One can tune the molar ratio of the two reactants (NHS-moiety:GV) to achieve the desired reaction efficiency. Next, allow the reaction to proceed for 4 hours at room temperature under gentle rotation. Next, quench the unreacted NHS-moieties using Tris-HCl buffer at pH 8 to a final concentration of 10 mM for 20 minutes at room temperature under gentle rotation. Next, add the whole reaction to dialysis tubes (6-8 kDa cutoff) and dialyze against a 4000× volume excess of PBS at 4° C. for 8 hours. Replace the buffer and allow dialysis to continue for an additional 8 hours. If NHS-moiety is not amenable to dialysis, repeated rounds of centrifugally-assisted purification is an alternative method to remove excess reactants and/or for buffer exchange. Chemically functionalized GVs can be stored in PBS buffer for up to one year at 4° C.

Example 12: Use of GVs as Contrast Agents for Non-Invasive Imaging Applications GVs can be used as a contrast agent in ultrasound imaging. The ultrasound pulses can be adjusted to have a peak positive pressure based on the acoustic collapse pressures of the GVs contained in the contrast agent.

A contrast agent comprising a plurality of GVs can be administered to a target site, each having a distinct ultrasound collapse pressure. Those contrast agents can then be selectively and individually removed from the imaging process to produce different images that, then, can be used for differential contrasting (comparing/subtracting one image from another to highlight the differences between the two images) to provide higher structure contrast in a final image.

The acoustic collapse profiles under ultrasound are evaluated for each GV type. GVs can be imaged in multi-well agarose phantoms at a chosen ultrasound frequency while being subjected to ultrasound pulses with increasing peak positive pressure amplitudes ranging from a lower value to a higher value. The acoustic collapse curves can be normalized by fitting the acoustic collapse curve with a Boltzman sigmoid function. From the normalized acoustic collapse curve, a number of acoustic collapse pressure can be derived, including an initial collapse pressure, midpoint collapse pressure and complete collapse pressure. The peak positive pressure of the ultrasound pulses can then be selected according to those derived acoustic collapse pressures.

To create a background contrast, a base image can be obtained by applying the ultrasound pulses having a peak positive pressure lower than the lowest initial collapse pressure of all the GV types in the contrast agent.

When two or more GV types are contained in the contrast agent, a maximally informative collapse pressure can be calculated based on the acoustic collapse pressure curves of a pair of spectrally adjacent GVs as described in the detailed description. The ultrasound pulses can then be selected to have a peak positive pressure equal to the maximally informative collapse pressure in order to maximally collapse one of the two GV types, but minimally collapse the other GV type.

An exemplary method to provide ultrasound imaging with the contrast of the GVs herein described is provided in FIG. 27.

Example 13: gvpC from *Halobacterium salinarum*, *Anabaena flos-aquae*, *Halobacterium mediterranei*, *Microchaete diplosiphon* and *Nostoc* sp GvpC protein can be isolated GVs from *Halobacterium salinarum*, *Anabaena flos-aquae*, *Halobacterium mediterranei*, *Microchaete diplosiphon* and *Nostoc* sp., and others identifiable by a skilled person. DNA sequences of gvpC proteins encoded by these species are shown in Table 3.

TABLE 3

DNA sequences of gvpC protein from exemplary species:

| Species | GenBank accession No. | DNA Sequence | SEQ ID NO: |
|---|---|---|---|
| *Anabaena flos-aquae* | X07544.1 | ATGATTTCTTTAATGGCAAAAATCCGGCAAGAAC ATCAGTCAATAGCAGAGAAAGTGGCTGAACTAT CTCTTGAGACCAGAGAATTCTTGTCCGTCACGAC AGCGAAAAGACAAGAGCAAGCTGAAAAACAAG CTCAAGAACTGCAAGCATTCTACAAGGATCTTCA GGAAACAAGTCAGCAGTTTTTATCAGAAACAGC CCAAGCCAGAATTGCTCAAGCTGAAAAACAAGC TCAAGAACTGTTAGCATTCCACAAAGAACTTCAA GAAACAAGTCAGCAGTTTTTATCAGCAACAGCCC AAGCCAGAATTGCTCAAGCTGAAAAACAAGCGC AAGAACTGTTAGCATTTTATCAAGAAGTTCGGGA AACAAGTCAGCAGTTTTTATCAGCAACAGCCCAA GCAAGAATTGCTCAAGCTGAAAAACAAGCTCAA GAACTGTTAGCATTCCACAAAGAACTTCAAGAA ACAAGTCAGCAGTTTTTATCAGCAACAGCCGACG CAAGAACTGCTCAAGCTAAGGAACAGAAGGAAT CTCTCCTGAAATTCCGTCAGGATTTGTTTGTGAG TATCTTTGGTTAATAA | 1 |
| *Halobacterium salinarum* | NC_002608.1 GeneID: 1449258 | ATGAGTGTCACAGACAAACGCGACGAGATGAGT ACTGCCCGCGATAAGTTCGCAGAATCACAGCAG GAGTTCGAATCATACGCTGACGAGTTTGCAGCCG ATATCACGGCAAAGCAAGACGATGTCAGCGACC TTGTCGATGCGATCACCGACTTCCAGGCGGAGAT GACCAACACGACGGATGCATTTCACACATATGGT GACGAGTTCGCCGCTGAGGTTGACCACCTCCGTG CCGATATTGACGCCCAGCGGGACGTGATCCGTG AGATGCAGGATGCGTTCGAGGCATATGCTGACA TCTTCGCTACAGATATCGCAGACAAACAAGATAT CGGCAATCTTCTGGCTGCGATTGAGGCGCTCCGA ACAGAGATGAACTCAACCCACGGGGCATTCGAA GCATATGCGGACGACTTCGCAGCCGATGTCGCTG CGCTCCGTGATATATCTGATCTGGTTGCAGCAAT CGACGACTTCAAGAGGAATTCATCGCCGTGCA GGACGCATTTGACAACTACGCTGGTGACTTCGAT GCGGAGATCGACCAGCTCCACGCTGCCATCGCTG ACCAGCACGACAGCTTCGACGCTACCGCGGACG CCTTCGCAGAGTACCGAGATGAGTTCTATCGCAT AGAGGTGGAAGCACTGCTTGAGGCGATCAACGA CTTCCAGCAGGACATCGGTGACTTCCGAGCGGA GTTTGAAACGACTGAGGACGCGTTCGTTGCCTTC GCCCGTGACTTCTATGGCCACGAGATCACGGCCG AGGAAGGCGCCGCCGAAGCGGAAGCCGAACCCG TCGAGGCTGACGCGGACGTCGAAGCGGAAGCAG AAGTCTCTCCAGACGAAGCTGGCGGAGAATCCG CCGGTACCGAGGAAGAAGAGACAGAGCCGGCCG AGGTGGAAACAGCGGCTCCAGAAGTAGAGGGGA GTCCTGCGGACACGGCAGACGAAGCGGAAGATA CGGAAGCAGAGGAGGAGACAGAGGAAGAGGCA CCGGAAGACATGGTGCAGTGCCGGGTGTGCGGC GAATACTATCAGGCCATCACGGAGCCCCATCTCC AGACCCATGATATGACGATTCAGGAGTACCGCG ACGAGTACGGTGAGGATGTCCCCCTTCGGCCGG ATGATAAAACATGA | 3 |
| *Halobacterium mediterranei* | CP007551.1 Protein ID: AHZ21249.1 | ATGAGTGTCAAAGACAAACGTGAAAAGATGACC GCCACCCGCGAGGAATTCGCGGAAGTACAGCAA GCGTTCGCGGCCTATGCCGACGAGTTCGCTGCCG ATGTTGACGATAAACGAGACGTAAGCGAACTCG TCGATGGGATTGATACCCTGCGACGGAGATGA ACAGCACTAACGATGCGTTTCGTGCATACAGTGA GGAATTCGCCGCCGACGTCGAGCACTTCCATACG TCGGTTGCTGACCGACGCGACGCCTTCGACGCGT ATGCCGACATTTTCGCGACAGATGTCGCGGAGAT GCAGGATGTGAGTGACCTCCTCGCCGCAATAGA CGACCTCCGGGCGGAGATGGACGAAACTCACGA AGCGTTCGACGCCTACGCGGATGCATTCGTGACC GACGTGGCTACCCTTCGCGATGTGTCGGACCTGC TGACGGCGATTTCGGAACTCCAGTCGGAATTCGT CTCTGTGCAGGGCGAATTTAACGACTACGCTAGT GAGTTCGGTGCCGACATCGACCAGTTCCACGCCG TTTGTCGCCGAAAAACGCGATGGTCACAAAGACG TTGCTGACGCCTTCCTCCAGTACCGAGAGGAATT TCACGGCGTCGAGGTACAGTCCTTATTGGACAAC ATCGCTGCCTTCCAGCGAGAAATGGGGGACTAC | 5 |

TABLE 3-continued

DNA sequences of gvpC protein from exemplary species:

| Species | GenBank accession No. | DNA Sequence | SEQ ID NO: |
|---|---|---|---|
| | | CGGAAAGCGTTCGAAACGACTGAGGAAGCGTTC<br>GCCTCCTTCGCTCGCGACTTCTACGGGCAGGGCG<br>CTGCTCCCATGGCGACACCCTTGAACAACGCGGC<br>TGAAACAGCCGTGACTGGCACGGAGACCGAGGT<br>AGACATACCTCCGATAGAAGACTCCGTAGAACC<br>CGACGGTGAAGACGAGGACTCGAAAGCAGATGA<br>CGTCGAAGCCGAAGCCGAAGTCGAGACGGTAGA<br>AATGGAGTTCGGTGCGGAGATGGACACAGAAGC<br>CGACGAAGACGTCCAATCGGAGTCGGTCAGAGA<br>AGACGACCAGTTCCTGGACGACGAGACGCCAGA<br>GGATATGGTCCAGTGTCTGGTGTGCGGCGAATAT<br>ACGACATGACGATCAAGAAATACCGCGAAGAGT<br>ACGGCGAGGACGTGCCACTCCGCCCGGATGATA<br>AAGCATGA | |
| Microchaete diplosiphon | X06085.1 | ATGACTCCTTTAATGATCAGAATCCGGCAAGAGC<br>ATCGAGGAATAGCAGAGGAAGTAACTCAACTAT<br>TTAAAGATACTCAAGAATTCTTGTCCGTGACCAC<br>AGCGCAAAGACAAGCGCAAGCTAAAGAACAAGC<br>TGAAAATCTGCATCAGTTCCATAAGGATCTGGAG<br>AAAGACACTGAAGAGTTTTTAACAGATACAGCT<br>AAAGAAAGAATGGCTAAAGCCAAACAGCAAGCT<br>GAAGATCTGTTCCAATTCCATAAGGAAATGGCA<br>GAAAACACCCAAGAGTTTTTGTCAGAAACAGCT<br>AAAGAAAGAATGGCGCAAGCTCAAGAGCAAGCT<br>CGACAATTGCGCGAATTCCATCAAAACCTTGAGC<br>AAACAACCAACGAATTTTTAGCTGACACAGCTA<br>AAGAAAGAATGGCGCAAGCTCAAGAACAAAAAC<br>AACAGCTACATCAATTCCGTCAGGATTTGTTTGC<br>TAGCATTTTTGGTACATTTTAG | 7 |
| Nostoc sp. | BA000019.2<br>Protein ID<br>BAB73951.1 | ATGACGGCTTTAATGGTAAGAATCCGGCAAGAG<br>CATCGGTCGATAGCTGAGGAAGTAACTCAACTAT<br>TTAGAGAGACTCATGAATTCTTGTCCGCTACAAC<br>AGCACACAGACAAGAGCAAGCCAAACAGCAAGC<br>GCAACAGCTACATCAGTTCCACCAAAATCTGGA<br>GCAGACAACCCACGAGTTTTTAACAGAAACCAC<br>AACACAAAGGGTTGCTCAAGCTGAAGCACAGGC<br>AAATTTTTTGCATAAGTTTCACCAAAATCTAGAA<br>CAGACCACCCAAGAGTTTCTAGCAGAAACAGCA<br>AAAAACAGAACTGAGCAAGCCAAAGCACAAAGT<br>CAATATCTGCAACAATTTCGTAAGGATTTGTTTG<br>CTAGTATTTTTGGCACATTTTAG | 9 |

The protein sequence of gvpC for these species can be found at Uniprot and other databases identifiable by skilled persons. Amino acid sequences of gvpC proteins encoded by *Halobacterium salinarum*, *Anabaena flos-aquae*, *Halobacterium mediterranei*, *Microchaete diplosiphon* and *Nostoc* sp are shown in Table 4.

TABLE 4

Protein sequences of gvpC from exemplary species:

| Species | UniProt ID No. | Amino acid Sequence | SEQ ID NO: |
|---|---|---|---|
| Anabaena flos-aquae | P09413 | MISLMAKIRQEHQSIAEKVAELSLETREFLSVTTA<br>KRQEQAEKQAQELQAFYKDLQETSQQFLSETAQ<br>ARIAQAEKQAQELLAFHKELQETSQQFLSATAQA<br>RIAQAEKQAQELLAFYQEVRETSQQFLSATAQAR<br>IAQAEKQAQELLAFHKELQETSQQFLSATADART<br>AQAKEQKESLLKFRQDLEVSIFG | 2 |
| Halobacterium salinarum | P24574 | MSVTDKRDEMSTARDKFAESQQEFESYADEFAA<br>DITAKQDDVSDLVDAITDFQAEMTNTTDAFHTY<br>GDEFAAEVDHLRADIDAQRDVIREMQDAFEAYA<br>DIFATDIADKQDIGNLLAAIEALRTEMNSTHGAFE<br>AYADDFAADVAALRDISDLVAAIDDFQEEFIAVQ<br>DAFDNYAGDFDAEIDQLHAAIADQHDSFDATAD<br>AFAEYRDEFYRIEVEALLEAINDFQQDIGDFRAEF<br>ETTEDAFVAFARDFYGHEITAEEGAAEAEAEPVE<br>ADADVEAEAEVSPDEAGGESAGTEEEETEPAEVE<br>TAAPEVEGSPADTADEAEDTEAEEETEEEAPEDM | 4 |

TABLE 4-continued

Protein sequences of gvpC from exemplary species:

| Species | UniProt ID No. | Amino acid Sequence | SEQ ID NO: |
|---|---|---|---|
| | | VQCRVCGEYYQAITEPHLQTHDMTIQEYRDEYG EDVPLRPDDKT | |
| Halobacterium mediterranei | Q02228 | MSVKDKREKMTATREEFAEVQQAFAAYADEFA ADVDDKRDVSELVDGIDTLRTEMNSTNDAFRAY SEEFAADVEHFHTSVADRRDAFDAYADIFATDV AEMQDVSDLLAAIDDLRAEMDETHEAFDAYAD AFVTDVATLRDVSDLLTAISELQSEFVSVQGEFN GYASEFGADIDQFHAVVAEKRDGHKDVADAFL QYREEFHGVEVQSLLDNIAAFQREMGDYRKAFE TTEEAFASFARDFYGQGAAPMATPLNNAAETAV TGTETEVDIPPIEDSVEPDGEDEDSKADDVEAEAE VETVEMEFGAEMDTEADEDVQSESVREDDQFLD DETPEDMVQCLVCGEYYQAITEPHLQTHDMTIK KYREEYGEDVPLRPDDKA | 6 |
| Microchaete diplosihon | P08041 | MTPLMIRIRQEHRGIAEEVTQLFKDTQEFLSVTTA QRQAQAKEQAENLHQFHKDLEKDTEEFLTDTAK ERMAKAKQQAEDLFQFHKEMAENTQEFLSETAK ERMAQAQEQARQLREFHQNLEQTTNEFLADTAK ERMAQAQEQKQQLHQFRQDLFASIFGTF | 8 |
| Nostoc sp. | Q8YUS9 | MTALMVRIRQEHRSIAEEVTQLFRETHEFLSATT AHRQEQAKQQAQQLHQFHQNLEQTTHEFLTETT TQRVAQAEAQANFLHKFHQNLEQTTQEFLAETA KNRTEQAKAQSQYLQQFRKDLFASIFGTF | 10 |

Example 14: Exemplary Methods for Producing gvpC Variant Proteins

Polynucleotides encoding gvpC DNA sequences such as those shown in Table 3 can be cloned into suitable expression plasmids, such as pET28a(+) plasmid (Novagen, Temecula, CA) downstream of a suitable promoter, such as a T7 promoter. Additionally, one or more tags as described herein can be encoded in the polynucleotide sequence of the plasmid to produce a tagged gvpC protein.

Recombinant gvpC constructs such as those described herein, comprising deletions of nucleotides encoding one or more amino acids of the WT gvpC sequence can be made using techniques such as restriction cloning, KLD mutagenesis, or Gibson assembly, among other techniques known in the art, using commercially available reagents and lab supplies, known to those skilled in the art.

Example 15: Expression and Purification of Ana GvpC Variants

The Ana GvpC gene sequence codon-optimized for *Escherichia coli* expression was synthesized by Life Technologies, Santa Clara, CA. Ana GvpC was cloned into a pET28a(+) plasmid (Novagen, Temecula, CA) downstream of a T7 promoter with an N or C-terminal His-tag. All constructs were made via restriction cloning, KLD mutagenesis, or Gibson assembly using enzymes from New England Biolabs, Ipswich, Massachusetts. Purified plasmids with the genetically engineered GvpC constructs were transformed into BL21(DE3) cells (Invitrogen, Carlsbad, CA). Starter cultures were diluted 1:250 in Terrific Broth (Sigma, St. Louis, MO) and allowed to reach $OD_{600}$~0.4-0.7. Protein expression was induced by addition of IPTG (to a final concentration of 1 mM), and cells were harvested by centrifugation after overnight expression at 30° C.

GvpC in the form of inclusion bodies were purified by lysing the cells using Solulyse supplemented with DNAseI (10 μg/mL) and lysozyme (400 μg/mL) at room temperature. Inclusion bodies were recovered by centrifugation at 27,000 g for 15 min in an ultracentrifuge. The inclusion body pellets were resuspended in 10 mM Tris-HCl buffer with 500 mM NaCl and 6 M urea (pH: 8.0) and incubated with Ni-NTA resin (Qiagen, Valencia, CA) for 2 h at 4° C. After washing, proteins were eluted using 250 mM imidazole. Bradford assay was used to measure the concentration of the purified protein. Purified GvpC variants were verified to be >95% pure by SDS-PAGE analysis.

Example 16: Ana GV Stripping and Re-Addition of Engineered GvpC Variants

Native Ana GVs were stripped of their outer GvpC layer by treatment with 6 M urea solution buffered with 100 mM Tris-HCl (pH 8.5). Two rounds of centrifugally assisted floatation followed by removal of the subnatant layer were done to ensure complete removal of native GvpC, as confirmed by SDS-PAGE. Stripped Ana GVs were then combined with 2× molar excess of the engineered GvpC variant in 6M urea buffer after accounting for a 1:25 binding ratio of GvpC:GvpA. Estimating 12,768 GvpA molecules per Ana GV and 564.2 pM of GVs per $O.D_{PS,500}$ (1 cm pathlength), the molar concentration of GvpA per $O.D_{PS,500}$ of Ana GVs was determined to be 7.2 μM and used for calculating the amount of engineered GvpC to be added. The engineered GvpC was then allowed to slowly refold onto the surface of the stripped Ana GVs by dialysis against 1×PBS for >12 h at 4° C. using a regenerated cellulose membrane with a 6-8 kDa M.W. cutoff (Spectrum Labs, Rancho Dominguez, CA). Dialyzed samples were subjected to at least 2 rounds of centrifugally assisted floatation to remove any excess unbound GvpC.

Example 17: Preparation of Recombinant GvpC Variants Engineered to Attach a HIS Tag An exemplary protocol for preparation and purification of recombinant GvpC with a C-terminal hexahistidine tag follows: First, transform >1 ng pure plasmid encoding recombinant GvpC with a C-terminal hexahistidine tag into BL21 (DE3) competent cells and grow culture in terrific broth with 50 µg/ml kanamycin overnight. Next, dilute 500 µL of the starter culture 1:1 with 50% glycerol in water and store at −80° C. Future starter cultures can be grown from aliquots of this glycerol stock instead of fresh transformations. Next, dilute starter culture 1:250 in terrific broth with 50 g/ml kanamycin and grow to $OD_{600}$~0.4-0.7 with shaking (250 rpm) at 37° C. Induce at a final concentration of 1 mM IPTG. Grow culture for 6-12 h at 30° C. with shaking. Next, pellet the cells in ultracentrifuge tubes at 5,500 g for 15 min at 4° C. and discard the supernatant. Cell pellets can be stored at −20° C. Protein extraction is typically more effective with frozen cells. Next, resuspend the pellets in 10 mL Solulyse with 10 µg/mL DNAse. Rotate at room temperature for 10 min. Next, centrifuge at 20,000 g for 15 m at 4° C. to clear the lysate and discard the supernatant. Resuspend the pellet in 10 mL Solulyse and lysozyme (0.25 mg/mL). Rotate at room temperature for 10 m. Add 5 mL Solulyse and vortex. Centrifuge at 20,000 g for 20 m at 4° C. and discard the supernatant. Thoroughly resuspend the pellet in 5 mL of inclusion body solubilization buffer. Centrifuge at 20,000 g for 20 m at 4° C. Add 1.5 mL Ni-NTA slurry to the supernatant, incubate at 4° C. with shaking (60 rpm) for 2 h or more. Pour into a polyprep column and collect all the flow-through, wash and elutions in the next steps. Collecting all fractions is good practice for troubleshooting and analyzing purification steps using SDS-PAGE. Wash with 10 column volumes of inclusion body wash buffer. Elute with 2 column volumes of inclusion body elution buffer. To quantify the eluted protein using the Bradford assay, prepare a standard curve of bovine serum albumin (BSA) at a final concentrations of 100, 250, 500, 750, 1000 and 1500 µg/mL in 60 µL of 3× diluted inclusion body elution buffer in PBS. Prepare dilutions of eluted protein 1:2 in PBS with a final volume 60 µL. Prepare a negative control of 3× diluted inclusion body elution buffer in PBS. To 25 µL of the sample and BSA standards, add 1 mL of Bradford reagent, vortex and incubate at room temperature for 5-10 m. Prepare all samples in duplicate. Blank the spectrophotometer with a negative control sample and measure the $OD_{595}$. Measure the $OD_{595}$ of the standard curve samples. Plot the $OD_{595}$ versus the concentration, and compute linear regression fit. Measure the $OD_{595}$ of the eluted protein samples. Use the linear fit from Step 37 to compute the unknown concentrations, and multiply by 3 (dilution factor) to obtain concentration of stock elution solution. The elutions can be stored separately at 4° C. Elution 1 has >80% of collected pure protein and is used for the subsequent experiments. Elution 2 is more dilute and is typically stored as backup or for running protein controls for SDS-PAGE.

Example 18: Preparation of Recombinant GvpC Variants Engineered to Attach a Spy Catch Tag An exemplary protocol for preparation of SpyCatcher-functionalized GVs follows: Mix SpyTag-functionalized GVs with SpyCatcher-fused proteins according to the formulation: 2*OD*395 nM*volume (in L) of SpyTag GVs=nmol SpyCatcher-fused protein. This results in a 2-fold excess of SpyCatcher to SpyTag in the reaction, based on the stoichiometry described in Step 39. Note that the SpyCatcher-mNeonGreen (SC-mNG) fusion protein used in [1] is expressed separately in E. coli as described herein and using a suitable the plasmid containing SC-mNG (details in the reagents section). SC-mNG is expressed as a soluble protein and hexahistidine-tagged, enabling purification using the same Ni-NTA slurry used for recombinant GvpC purification. Unlike GvpC inclusion bodies, soluble proteins are in the supernatant after cell lysis with Solulyse/DNAse (Step 24), allowing direct incubation of the supernatant with the slurry (Step 30). Wash and elution (Steps 31-33) are performed with soluble protein wash buffer and soluble protein elution buffer respectively, and the protein is desalted into PBS using PD10 desalting columns. Protein quantification is done using the Pierce or Bradford assay before use. Incubate 1 hour or more at room temperature. Centrifuge at 300 g for 3 hours or until subnatant is clear. Remove clear subnatant with syringe with 21.5 G needle. Retain milky white supernatant in the tube. Resuspend supernatant in PBS. Repeat this centrifugation step one time. Store at 4° C.

Example 19: Preparation of Recombinant GvpC Variants

GVs comprising recombinant gvpC can be prepared using any method known in the art. An exemplary protocol for preparation of GVs with recombinant GvpC follows: Add recombinant GvpC to ΔGvpC GVs according to the formulation: 2*OD*198 nM*volume (in L) of GVs=nmol recombinant GvpC. This provides a 2-fold stoichiometric excess of GvpC relative to binding sites on an average Ana GV, assuming a 1:25 molar ratio of GvpC:GvpA binding based on previous work[27]. The exact volume of recombinant GvpC to be added is calculated based on the molar mass of the particular variant and the concentration of eluted GvpC (measured by Bradford assay). For truncated GvpC variants with a lower GV binding affinity, a higher stoichiometric excess may be added to promote attachment of GvpC to the GV surface. However, note that adding too much excess of GvpC might lead to protein aggregation during dialysis. Soak the dialysis tubing in PBS for 5 minutes. Add samples (GVs+recombinant GvpC) into dialysis tubing and clip both sides. Dialyze in 4 L PBS with stirring on low speed for at least 12 h. The length of dialysis tubing used for each sample depends on the total volume of the dialysate, which is determined by the amount of engineered GVs required for the end application. The type of dialysis tubing used (molecular weight cutoff) can change depending on the GvpC variant, as truncated variants may have a much lower molecular weight. Transfer the dialysate into 2-mL centrifuge tubes and spin at 300 g for 3 hours, or until subnatant is clear. Remove subnatant with syringe with a 21.5 G flat needle. Retain the milky white supernatant in the tube. Resuspend GVs in PBS. Repeat this centrifugation step one time. The GVs can be stored at 4° C.

Example 20: Modular Genetic Engineering of Acoustic Protein Structures

Figure 2A:
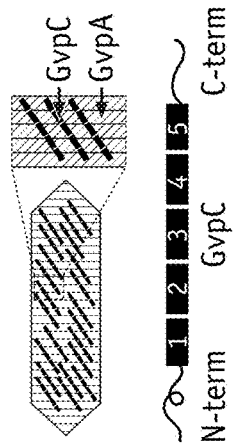
FIGS. 2A-2E show schematics showing GVs as a molecular engineering platform for acoustic protein structures.
Figure 2B:
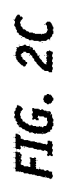
Figure 2C:
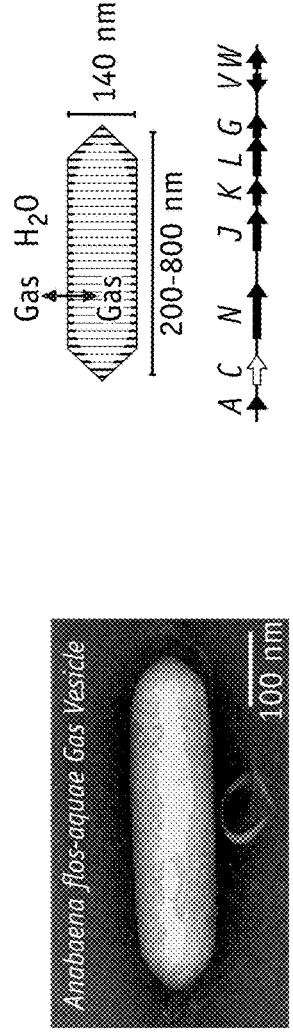
Figure 2D:
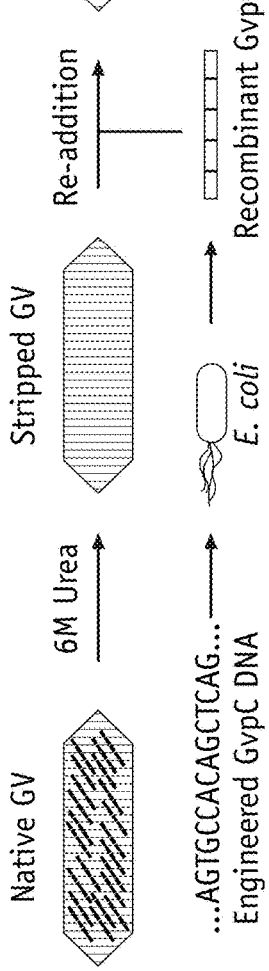
Figure 2E:
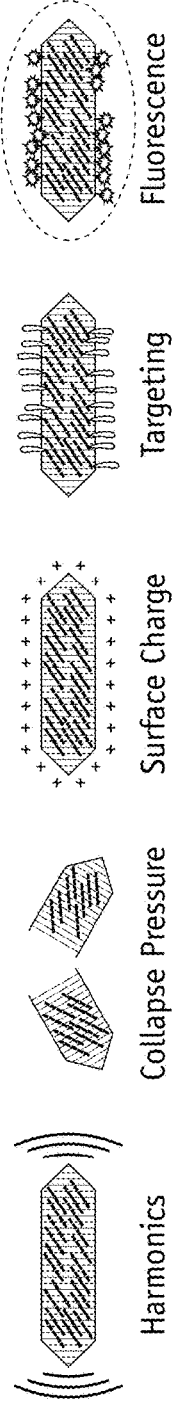
Figure 3:
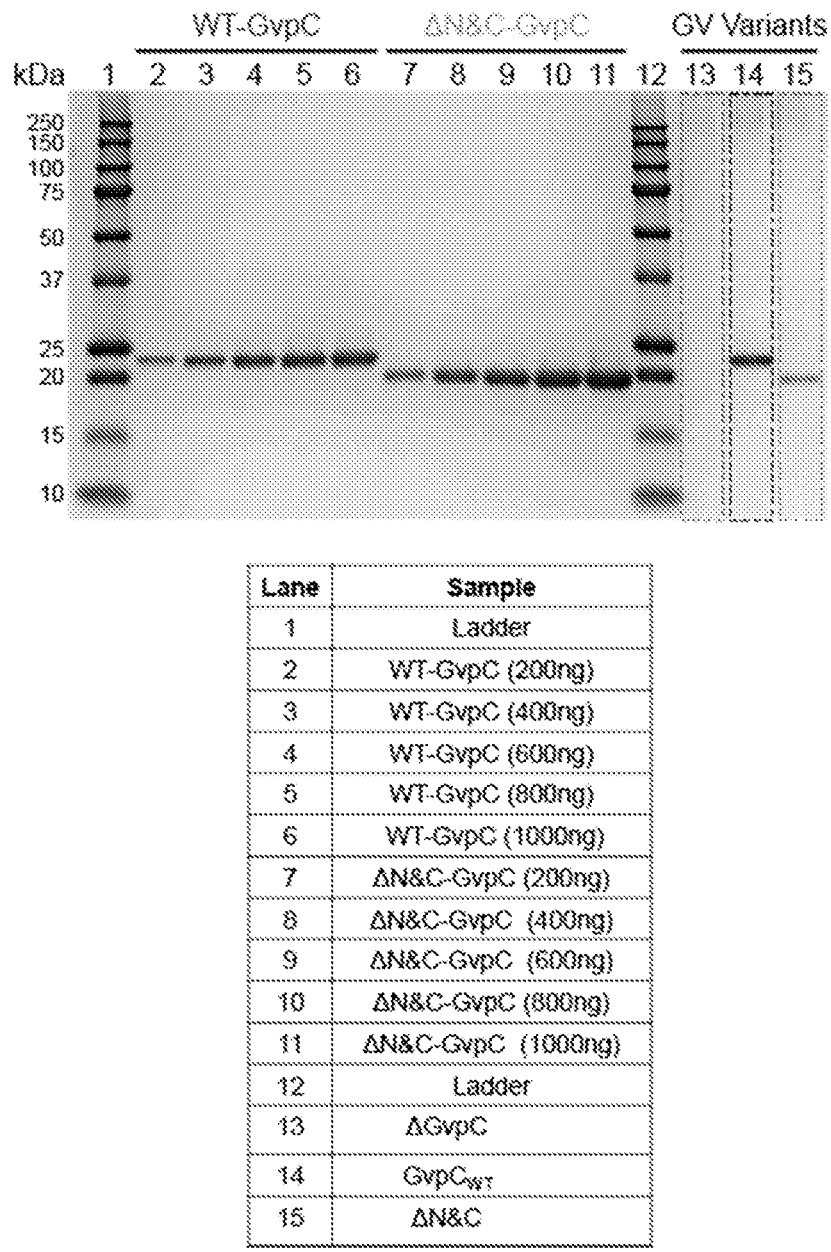
FIG. 3 shows an exemplary SDS-PAGE analysis confirming the complete removal of GvpC from native Ana GVs (lane 13) and the re-addition of engineered proteins (lane 14-15). Quantification of re-added GvpC on urea-stripped Ana GVs was done by comparison against a standard curve (200-1000 ng) of the pure proteins (lanes 2-6 for WT-GvpC and lanes 7-11 for ΔN&C-GvpC). The number of re-added GvpC molecules was determined to be ~1980 per GV for $GvpC_{WT}$ and ~877 per GV for ΔN&C respectively.

To enable modular molecular engineering of Ana GVs, a platform was established in which genetically engineered GvpC variants are recombinantly expressed in Escherichia coli and subsequently added to Ana GVs that have been purified from Anabaena flos-aquae and stripped of their native GvpC proteins (FIG. 2D). The GVs were isolated by hypertonic and detergent-mediated lysis, followed by purification with centrifugally assisted floatation. Native GvpC was removed by treating the GVs with 6M urea, which leaves the GvpA-based shell intact.[28, 29] Genetically engineered variants of Ana GvpC were produced containing N- or C-terminal hexahistidine sequences in Escherichia coli and purified the resulting inclusion bodies by nickel chromatography in 6M urea. Dialysis of recombinant GvpC in the presence of stripped Ana GVs into physiological buffer resulted in Ana GVs with a new, engineered GvpC layer (FIG. 2D). SDS-PAGE analysis confirmed the complete removal of GvpC from native Ana GVs and the re-addition of engineered proteins (FIG. 3).

Example 21: Tuning of Collapse Pressure for Acoustic Multiplexing

Figure 5:
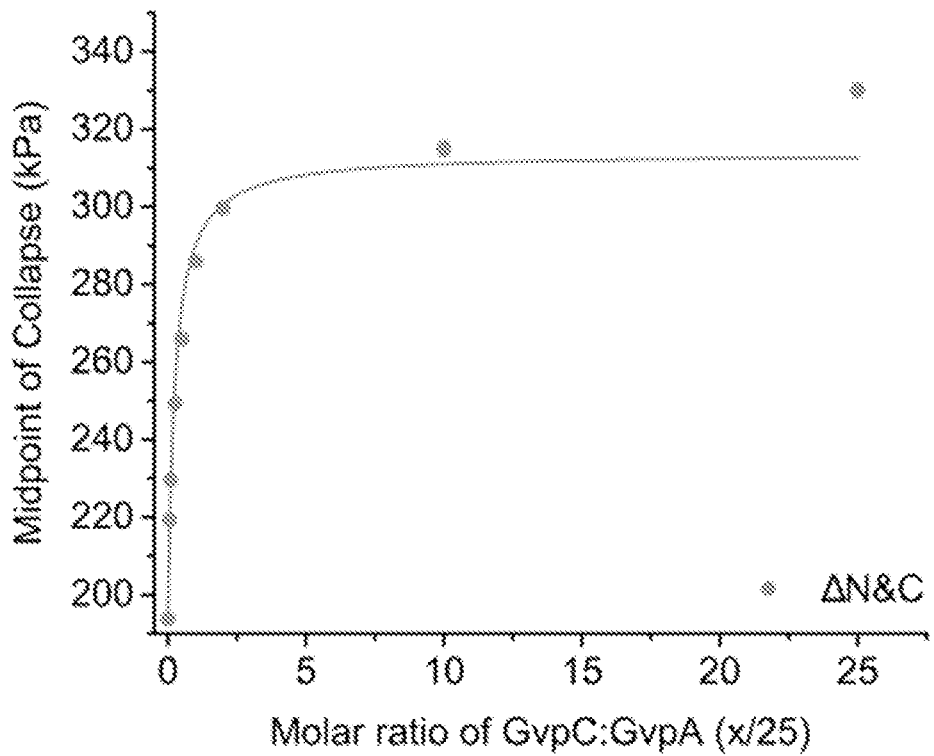
FIG. 5 shows a graph reporting exemplary results of midpoint of collapse (hydrostatic) plotted as a function of re-added GvpC concentration for the ΔN&C variant. The midpoint of collapse was determined by fitting the raw data with a Boltzmann sigmoid function of the form $f(p)=(1+e^{(p-p_c)/\Delta p})^{-1}$ with $p_c$ representing the average midpoint of collapse. Fit parameters and $R^2$ values for each of the GV variants are provided in the table below the graph. The saturation curve was plotted by fitting the data to a bimolecular binding function of the form $f(x)=C_1*x/(K_d+x)+C_2$.
Figure 6:
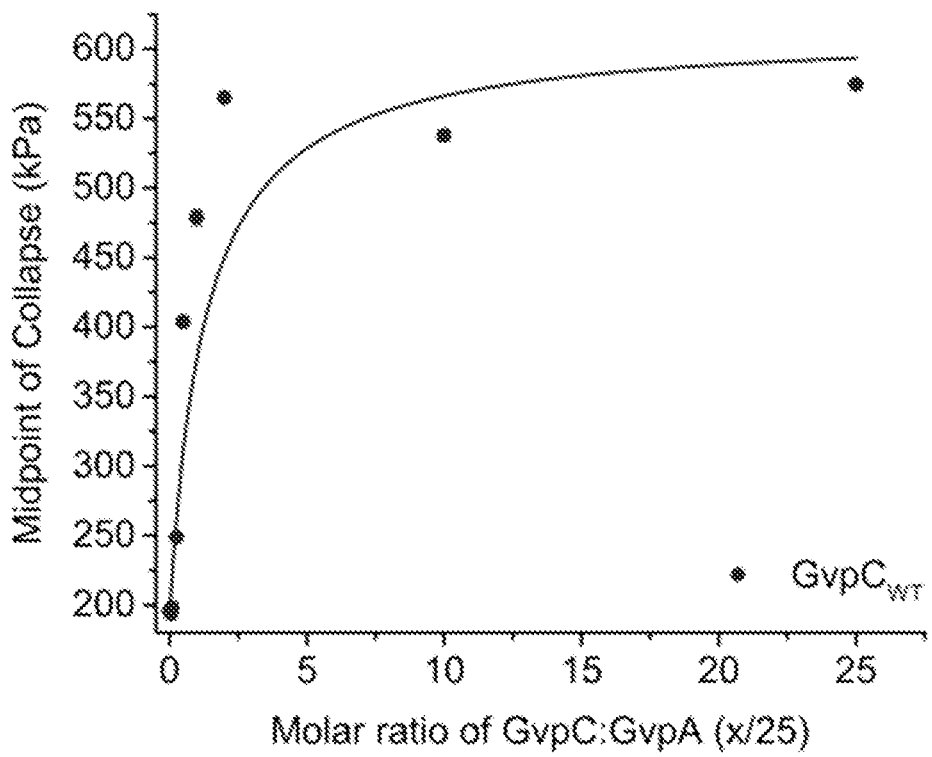
FIG. 6 shows a graph reporting exemplary results of midpoint of collapse (hydrostatic) plotted as a function of re-added GvpC concentration for the $GvpC_{WT}$ variant. The midpoint of collapse was determined by fitting the raw data with a Boltzmann sigmoid function of the form $f(p)=(1+e^{(p-p_c)/\Delta p})^{-1}$ with $p_c$ representing the average midpoint of collapse. Fit parameters and $R^2$ values for each of the GV variants are provided in the table below the graph. The saturation curve was plotted by fitting the data to a bimolecular binding function of the form $f(x)=C_1*x/(K_d+x)+C_2$.

The gaseous interior of GVs can be collapsed with hydrostatic and acoustic pressure, erasing their ultrasound scattering signal and enabling multiplexed imaging of GVs with distinct collapse pressure thresholds.[30] To determine whether genetic tuning could enable enhanced multiplexing, three Ana GV variants were engineered with distinct mechanical properties. ΔGvpC comprises GVs completely lacking the outer GvpC layer; ΔN&C contains a truncated form of GvpC without its N- and C-terminal regions; $GvpC_{WT}$ has an engineered GvpC protein that closely resembles the wild-type sequence (FIG. 4A). The hydrostatic collapse behavior of these structures was assessed using pressurized absorbance spectroscopy, in which the optical density of GVs (which scatter 500 nm light when intact) is measured under increasing hydrostatic pressure. This provides a rapid assessment of GV mechanics and allows comparisons to literature [3]. These three variants spanned a dynamic range of 380 kPa (FIG. 4B, Table 5). ΔGvpC had the lowest collapse pressure midpoint at 195.3±0.3 kPa, the ΔN&C variant showed an intermediate value of 374.3±1 kPa and $GvpC_{WT}$ had the highest value of 569.9±4 kPa (Table 5, N=7, ±SEM). To ensure that the decrease in collapse pressure for the ΔN&C variant was not due to unsaturated binding caused by reduced affinity of this GvpC variant for GvpA, collapse midpoints were measured as a function of re-added GvpC concentration and confirmed that binding was near saturation (FIG. 5, FIG. 6).

Table 5 shows hydrostatic midpoint of collapse for engineered Ana GVs used in acoustic multiplexing experiments (FIG. 4B). The data was fitted with a Boltzmann sigmoid function of the form $f(p)=(1+e^{(p-p_c)/\Delta p})^{-1}$ with $p_c$ representing the average midpoint of collapse. Fit parameters and $R^2$ values for each of the GV variants are provided in the table.

TABLE 5

Hydrostatic midpoint of collapse for engineered Ana GVs used in acoustic multiplexing experiments

| GV Variants | Midpoint of Collapse ($P_c$) (kPa) | $P_c$ (SEM) (kPa) | ΔP (kPa) | ΔP (SEM) (kPa) | Adj. R-Square |
|---|---|---|---|---|---|
| ΔGvpC | 195.30 | 0.27 | 17.01 | 0.24 | 0.999 |
| ΔN&C | 374.30 | 1.01 | 41.46 | 0.89 | 0.999 |
| $GvpC_{WT}$ | 569.85 | 3.64 | 84.87 | 3.21 | 0.992 |

Additional exemplary gvpC variants were engineered, the aligned protein sequences of which are shown in FIGS. 11A-11C, and as described in Table 6.

TABLE 6

Exemplary gvpC variants

| Ana gvpC Variant | Engineered protein features |
|---|---|
| ΔN&C-CERY1 | GvpC comprising deletions of N- and C- terminal regions, and an ERY1 tag fused to the C-terminus of gvpC and a His-tag in the N-terminal region |

TABLE 6-continued

Exemplary gvpC variants

| Ana gvpC Variant | Engineered protein features |
|---|---|
| ΔNterm | GvpC comprising a deletion of N-terminal region and a His-tag fused to the C-terminus |
| N-rep3-C | GvpC comprising N-terminal region, repeat 3, and C-terminal region, and a His-tag fused to the C-terminus |
| SR3CERY1 | GvpC comprising N-terminal region containing a His-tag, repeat 3, and an ERY1 tag fused to the C-terminus |
| WTCERY1 | GvpC comprising a His-tag in the N-terminal region, repeat regionsand anERY1 tag fused to the C-terminus |
| N-rep1-C | GvpC comprising N-terminal region, repeat 1, a C-terminal region and a His-tag fused to the C-terminus |
| SR1CERY1 | GvpC comprising N-terminal region, repeat 1, and C-terminal region, a His-tag in the N-terminal region and anERY1 tag fused to the C-terminus |
| ΔN&C | GvpC comprising deletions of N- and C- terminal regions and a His-tag fused to the C-terminus |
| N-rep2endto3mid-C | GvpC comprising N-terminal region, a region from a midpoint of repeat 2 to within a midpoint of repeat 3, and C-terminal region, and a His-tag fused to the C-terminus |
| N-His-GvpC | GvpC comprising a His-tag in the N-terminal region |
| ΔCterm | GvpC comprising a deletion of C-terminal region and a His-tag fused to thelast repeat |
| GvpCWT-ACPP | GvpC comprising a His-tag in the N-terminal region and an ACPP tag fused to the C-terminus |
| GvpCWT-hPRM | GvpC comprising a His-tag in the N-terminal region and an hPRM tag fused to the C-terminus |
| GvpCWT-LRP | GvpC comprising a His-tag in the N-terminal region and an LRP tag fused to the C-terminus |
| GvpCWT-mCD47 | GvpC comprising a His-tag in the N-tenninal region and a mCD47 tag fused to the C-terminus |
| GvpCWT-R8 | GvpC comprising a His-tag in the N-terminal region and an R8 tag fused to the C-terminus |
| GvpCWT-RGD | GvpC comprising a His-tag in the N-terminal region and an RGD tag fused to the C-terminus |
| GvpCWT-RDG | GvpC comprising a His-tag in the N-terminal region and an RDG tag fused to the C-terminus |
| GvpC-SpyTag | GvpC comprising a SpyTag fused to the C-terminus, and a His-tag fused to the C-terminus of the SpyTag |
| N-rep1to3-C | GvpC comprising an N-terminal region, repeats 1 to 3, a C-terminal region, and a His-tag fused to the C-terminus |
| N-rep1to2-C | GvpC comprising an N-terminal region, repeats 1 to 2, a C-terminal region, and a His-tag fused to the C-terminus |
| N-rep1to4-C | GvpC comprising an N-terminal region, repeats 1 to 4, a C-terminal region, and a His-tag fused to the C-terminus |
| GvpCWT | GvpC comprising a His-tag fused to the C-terminus |

FIG. 18 shows a predicted alignment of the tandem repeat regions (Rep) in gvpC from Anabaena flos-aquae, wherein the five repeat regions 1-5 (rep1, rep2, rep3, rep4, and rep5) are preceded by an upstream N-terminal region and are followed by a downstream C-terminal region. Some of the variants described here were produced by deletions of various parts of the N- and/or C-terminal regions, or one or more repeat regions, as described in Table 6.

Figures 19A, 19B:
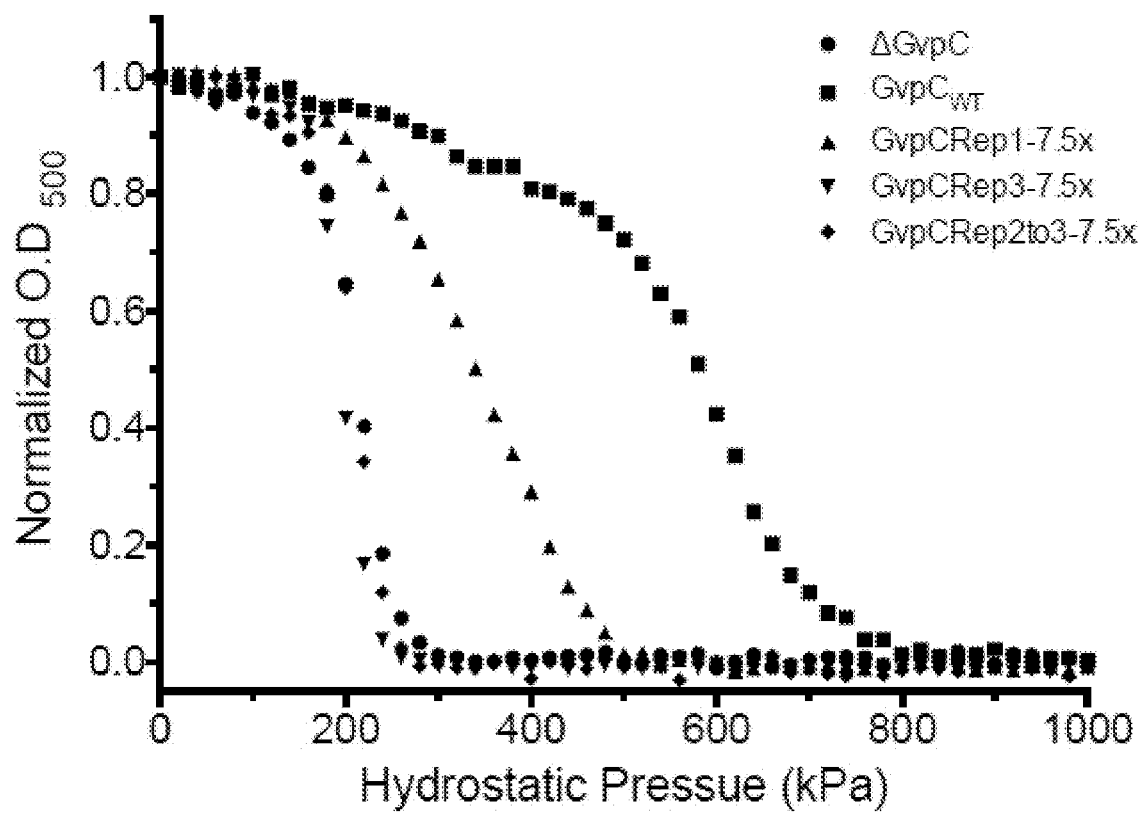
FIGS. 19A-19B shows examples of GvpC engineering that enables tuning of GV collapse pressure for acoustic multiplexing.
Figure 20:
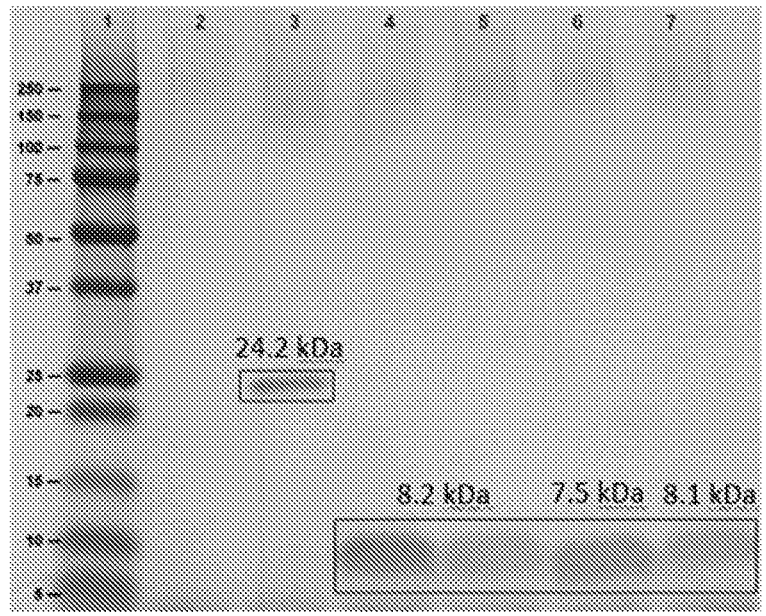
FIG. 20 shows an exemplary SDS-PAGE analysis confirms that the indicated gvpC variants bound to gvpA of intact GVs (shown in boxes around bands). The results indicate that truncated single repeat variants bind to GVs but do not strengthen the GV wall to the same extent. All samples were between OD$_{500}$: 5.5 to 6.5 before 1:1 dilution with SDS-loading buffer.
Figures 21A, 21B:
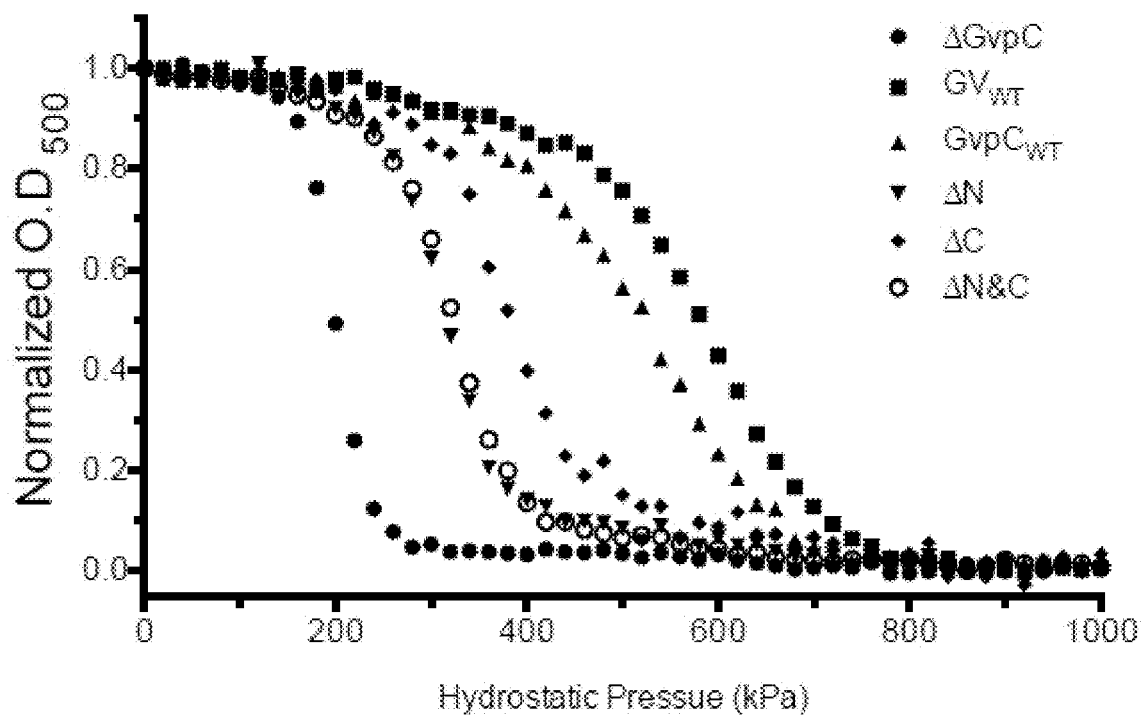
FIGS. 21A-21B show examples of GvpC engineering that enables tuning of GV collapse pressure for acoustic multiplexing.

The hydrostatic collapse behavior of the additional gvpC variants structures was assessed, as above, using pressurized absorbance spectroscopy. FIGS. 19A-19B show that Rep1 (also described herein as N-rep1-C) strengthens GVs more than Rep2to3 (also described herein as N-rep2endto3mid-C) or Rep3 (also described herein as N-rep3-C). FIG. 20 shows that all three variants Rep1, Rep2to3 and Rep3 bind to GVs, indicating that gvpc binding to GVs is not sufficient to strengthen GVs, but binding of different gvpc variants impart different strengthening to GVs. In addition to GVs comprising the ΔN&C variant described above (also described herein as Δnose/tail), hydrostatic collapse behavior of GVs comprising additional variants Δnose (also described herein as ΔNterm) and Δtail (also described herein as ΔCterm) were assessed (FIGS. 21A-21B), and show that truncating the N-terminus of gvpc decreases collapse pressure to a greater extent than truncating the C-terminal tail, and deleting N&C at the same time produces GVs with lower collapse pressure than either truncation done separately. Hydrostatic collapse behavior of GVs comprising variants gvpcΔ4, gvpcΔ3, gvpcΔ2, and gvpcΔ1 were also assessed (FIGS. 21A-21B).

The data on all variants described herein are summarized in FIG. 17. FIG. 17 also shows that adding molar excess of GvpC prior to dialysis increases collapse pressure up to a certain threshold, above which the collapse pressure plateaus and does not increase any further (also see FIG. 5 and FIG. 6). Furthermore, appending a His-Tag (6 amino acids) to the N-terminus of the wild-type GvpC sequence does not cause a substantial change in collapse pressure. Deletion of 5th and 4th repeat has little effect on collapse, while deletion of 2nd repeat has a much bigger effect. Thus, removing repeats from the C-terminal end typically has a lower effect on the collapse pressure compared to removing repeats close to the N-terminal end.

Overall, deletions of repeats cause less decrease of collapse pressure than deletions to the terminal regions of GvpC. N-terminal repeats appear to be important for GvpC-based strengthening, in particular, as deletion of repeat 2 decreases collapse pressure by ~150 kPa, while deletion of repeats 5 and 4 do not have a substantial impact on collapse pressure, and the observation that repeat 3 (consensus repeat sequence) binds to GVs but does not strengthen, while repeat 1 binds and strengthens GVs.

Next, collapse profiles under ultrasound were evaluated under. GVs were imaged in multi-well agarose phantoms at 6.25 MHz while being subjected to ultrasound pulses with increasing peak positive pressure amplitudes ranging from 290 kPa to 1.23 MPa.

The acoustic collapse curve can be normalized by fitting the acoustic collapse curve with a Boltzmann sigmoid function. Exemplary parameters for fitting the acoustic collapse curve with the Boltzmann sigmoid function can be found in Table 7. Table 7 also lists the acoustic midpoint of collapse for engineered Ana GVs used in multiplexing experiments (FIG. 4C).

TABLE 7

Exemplary parameters used in Boltzmann sigmoid function fitting

| GV Variants | Midpoint of Collapse (Pc) (kPa) | $P_c$ (SEM) (kPa) | ΔP (kPa) | ΔP (SEM) (kPa) | Adj. R-Square |
|---|---|---|---|---|---|
| ΔGvpC | 571.00 | 1.51 | 14.48 | 1.03 | 0.998 |
| ΔN&C | 657.04 | 3.94 | 77.47 | 3.70 | 0.997 |
| GvpC$_{WT}$ | 868.81 | 6.56 | 94.00 | 5.57 | 0.994 |

The data was fitted with the form $f(p)=(1+e^{(p-p_c)/\Delta p})^{-1}$ with $p_c$ representing the average midpoint of collapse. Fit parameters and $R^2$ values for each of the GV variants are provided in the table.

Similar to trends observed for hydrostatic collapse, the ΔGvpC variant collapses under the lowest acoustic pressure, followed by ΔN&C and GvpC$_{WT}$ (FIG. 4C, Table 7). Notably, the collapse midpoints in the acoustic regime were substantially higher than in the hydrostatic regime. This is explained by GVs having a gas efflux time of approximately 1.5 μs,[31] which is too slow for gas molecules contained in the GV to exit the structure during the 80 ns positive half-cycle of 6.25 MHz ultrasound, allowing the gas to compressively reinforce the GV shell. On the other hand, under hydrostatic conditions, pressure changes occur on the time scale of seconds, allowing gas molecules to exit the GV during pressurization and resulting in the shell carrying the full compressive load by itself. [32] It is also noted that the acoustic collapse curves appear somewhat more closely spaced than hydrostatic collapse curves, which can be explained by the applied acoustic pressure field having a non-uniform profile over the imaged GV sample. Fitting a Boltzmann sigmoidal function to these collapse curves reveals a unique acoustic collapse spectrum for each engineered GV (FIG. 4D).

To take advantage of the distinct acoustic collapse spectra of different GV variants for multiplexed imaging, pressure spectral unmixing was used to obtain multiplexed images of our three GV variants. FIG. 4F shows ultrasound images taken at a non-destructive baseline pressure before and after exposing the GV samples to three sequentially increasing collapse pulses. The spectrally unmixed images (FIG. 4G) uniquely identify acoustic signals from each GV variant. FIG. 7 shows the matrix of coefficients used to generate these images. This combination of engineered GVs and pressure spectral unmixing can be useful in many scenarios requiring ultrasound imaging of multiple molecular targets in the same sample.

Example 22: Maximally Informative Acoustic Pressure of a GV in Mixture of GV Variants For any two spectrally adjacent GVs, the maximally informative pressure refers to as an acoustic pressure that can maximize the collapse of one GV but minimize the collapse of the other GV.

Figure 4D:
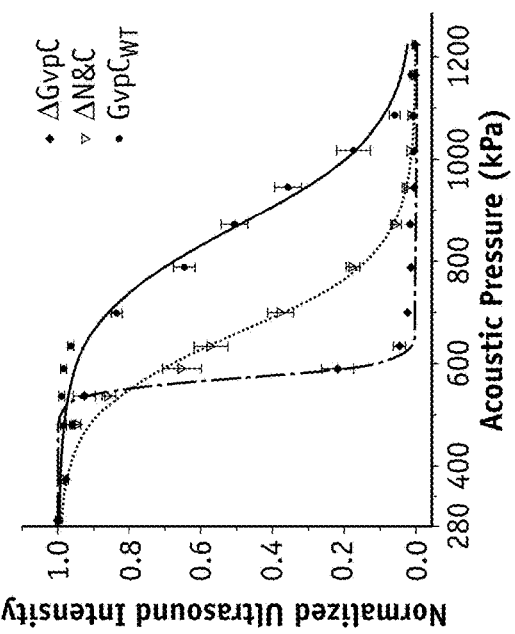

As shown in FIG. 4D, ΔGvpC and ΔN&C are two spectrally adjacent GVs, ΔN&C and GvpC$_{WT}$ are two spectrally adjacent GVs, while ΔGvpC and GvpC$_{WT}$ are not spectrally adjacent.

The maximally informative acoustic pressure can be measured by constructing an acoustic collapse curve for each GV used in the contrast agent as shown in FIG. 4C as described above. The maximally informative pressure between the two GV types can be calculated based on fitted sigmoid function $f(p)$. For two GV types having a fitted sigmoid $f_1(p)$ and $f_2(p)$, the maximally informative collapse pressure, $p_{max}$, is chosen so as to maximize the difference between $f_1(p_{max})$ and $f_2(p_{max})$.

For example, as shown in FIG. 4D, the first maximal informative acoustic pressure applied during the multiplexing ultrasound imaging is estimated as 630 kPa. The first maximal informative acoustic pressure is capable of maximally collapsing the ΔGvpC variant while minimally collapsing the other two variants, i.e. ΔN&C and GvpC$_{WT}$. The second maximal informative acoustic pressure is estimated as 790 kPa. The second maximal informative acoustic pressure is capable of maximally collapsing the ΔN&C variant while minimally collapsing the remaining variant, i.e. GvpC$_{WT}$. The third, and the last, maximal informative acoustic pressure is 1230 kPa. This maximal informative acoustic pressure is applied to collapse the remaining GvpC$_{WT}$ variant, i.e. it is greater than the acoustic pressures plotted on the GvpC$_{WT}$ curve in FIG. 4D.

Example 23: Modulation of Harmonic Ultrasound Signals

Non-linear signals from ultrasound contrast agents can dramatically enhance their ability to be distinguished from background tissues, which mainly scatter linearly. [33, 34] In the initial description of gas vesicles as ultrasound reporters, it was found that GVs from *Halobacterium salinarum* (Halo GVs) produce strong non-linear signals in the form of harmonics of the insonation frequency, while Ana GVs show no harmonic response.[30] Since Halo GVs also have a significantly lower critical collapse pressure than Ana GVs,[3] it is hypothesized that altering Ana GV shell mechanics by engineering GvpC could yield Ana GVs with harmonic signals.

Figure 8A:
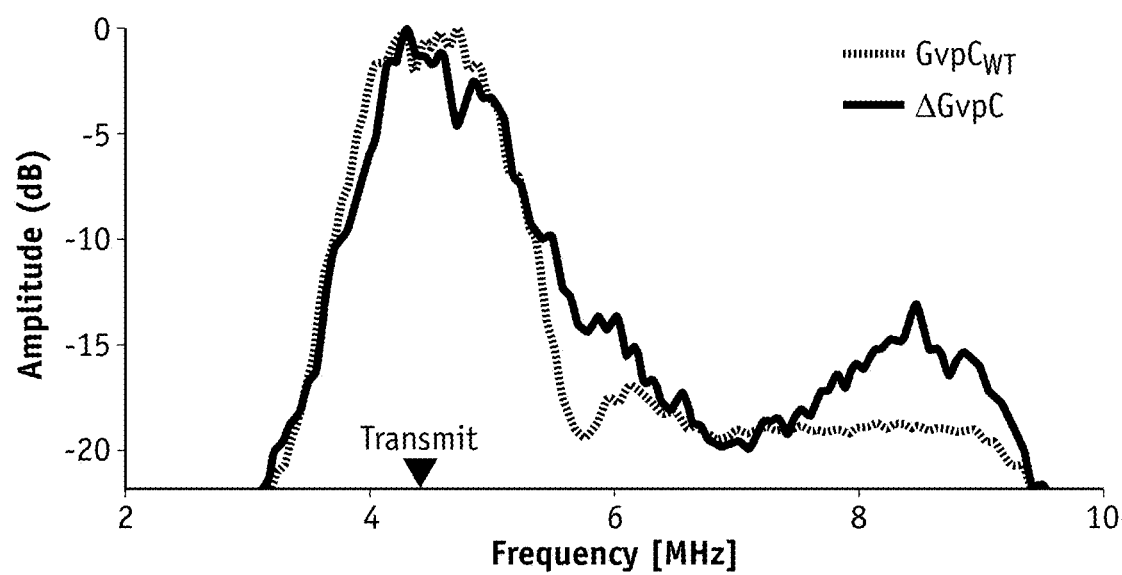

Accordingly, the frequency response of engineered Ana GVs to 4.46 MHz pulses over a receive bandwidth of 2-10 MHz was characterized. Consistent with the hypothesis, ΔGvpC showed a sharp peak at the second harmonic frequency of 8.9 MHz in addition to the fundamental peak at the transmitted frequency, while GvpC$_{WT}$ showed only a linear signal (FIG. 8A). Ultrasound images formed by bandpass filtering around the fundamental and second harmonic frequencies showed a substantial difference in the harmonic acoustic response of GV variants (p<0.01, N=7, paired t-test), for the same level of fundamental signal (FIGS. 8B-8E). The harmonic signals from ΔGvpC were 3.71-fold higher than GvpC$_{WT}$ (FIG. 8E). These results demonstrate for the first time that protein engineering can be used to modulate the acoustic properties of a structure.

Figure 9A:
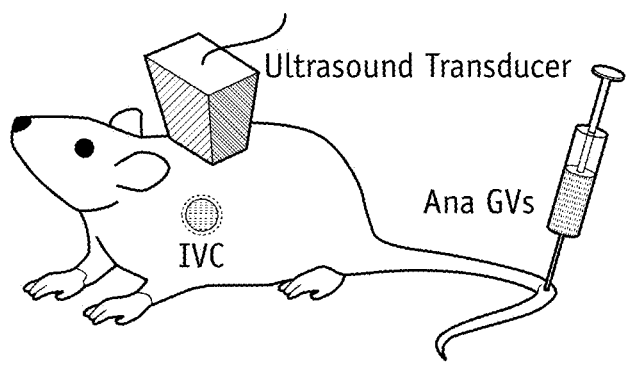
FIGS. 9A-9E show exemplary images and graphed results showing that GV engineering enables modulation of harmonic signals in vivo.
Figure 9B:
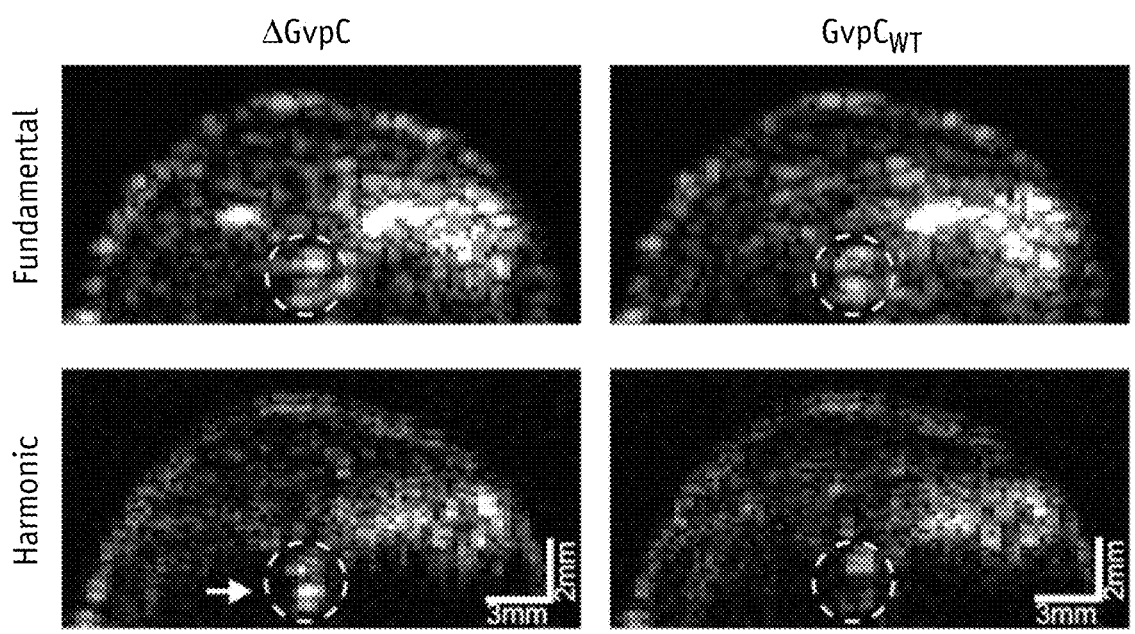
Figure 9C:
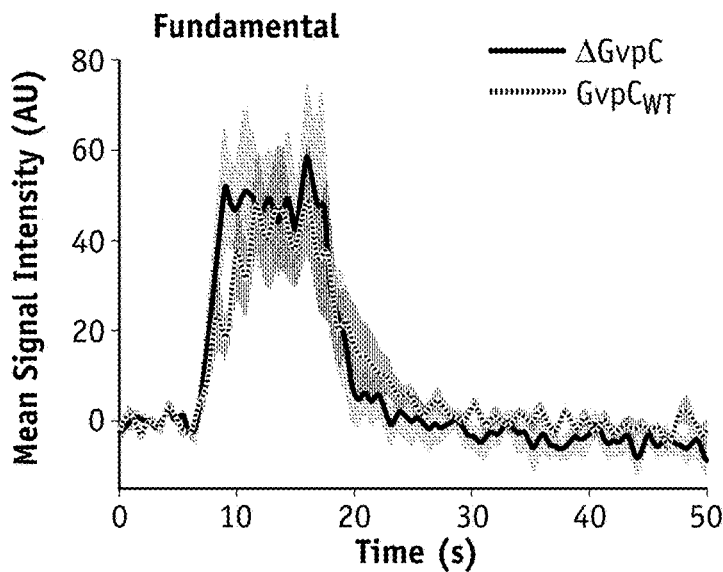
Figure 9D:
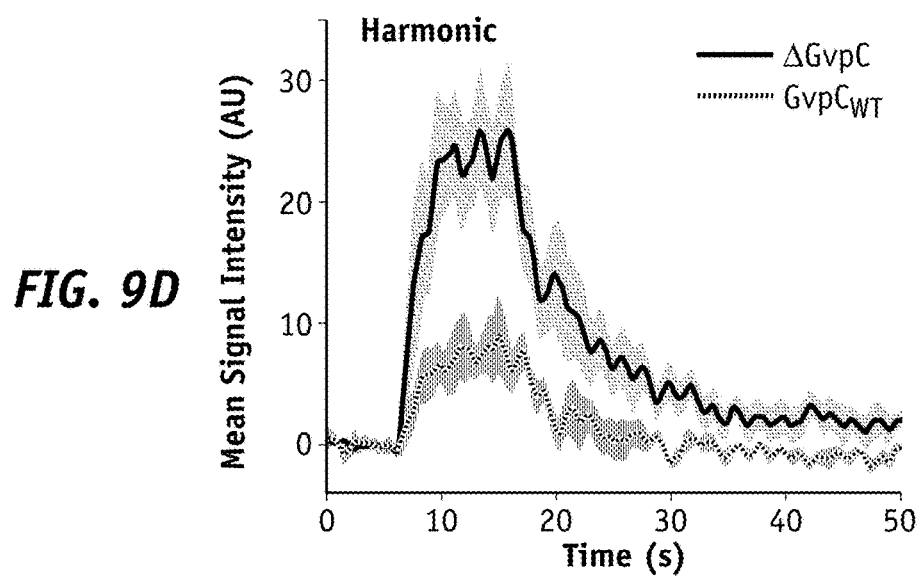
Figure 9E:
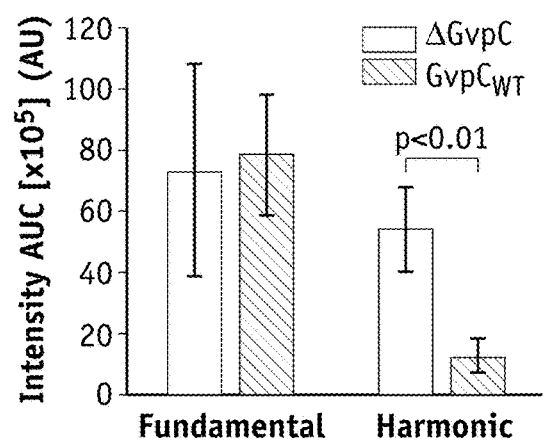

To show that engineered Ana GV variants are capable of producing harmonic signals in vivo, intravenous injections of the ΔGvpC and GvpC$_{WT}$ variants into live, anaesthetized mice were performed. Ultrasound imaging of the inferior vena cava (IVC) was performed in fundamental and second-harmonic modes (transmission at 4.46 MHz and reception filtered around 4.46 MHz and 8.9 MHz center frequencies, respectively). FIG. 9A provides a schematic illustration of the in vivo experiment. Five seconds after the start of the injection, enhanced non-linear signals were observed for the ΔGvpC variant compared to GvpC$_{WT}$, while their fundamental signals were comparable (FIGS. 9B-9D). Repeated trials showed a statistically significant difference (p<0.01, N=6, paired t-test) in the harmonic response of the two variants for the same level of fundamental signal (FIG. 9E), consistent with in vitro results. The ability to genetically tune the harmonic properties of GV contrast agents will dramatically enhance their utility for in vitro and in vivo imaging.

Figure 10A:
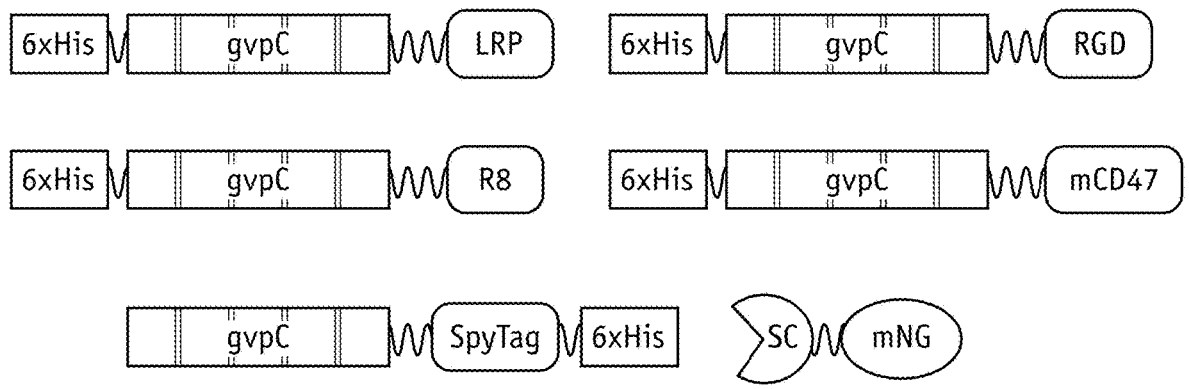
Figure 10B:
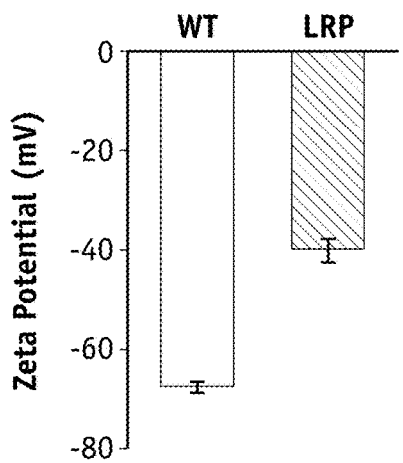

Example 24: Tuning of Surface Charge, Targeting Specificity and Multimodal Imaging After demonstrating the ability of GvpC to serve as a genetic platform for tuning the mechanical and acoustic properties of GVs, its capacity to enable the engineering of GV surface properties and add functionality was examined. To do so, the C-terminus of GvpC was used as modular sites for protein fusion (FIG. 10A, FIGS. 11A-11C). As a first proof of concept, the ability of GvpC fusions to modulate GV surface charge was tested, an important property that influences the behavior of structures in solution and in vivo.[35] GvpC was fused with the lysine rich protein (LRP), which contains 100 positive charges at physiological pH. Re-addition of this protein to GVs resulted in structures with 28±4 mV higher zeta potential compared to GvpC$_{WT}$ (FIG. 10B).

Next, the ability of GvpC fusions to endow GVs with functionality for specific cellular targeting was tested. A well-studied receptor-targeting peptide is RGD, which binds effectively to a wide range of integrins.[36] GVs engineered to express GvpC$_{RGD}$ on their surface were compared with wild type GvpC and scrambled GvpC$_{RDG}$ controls in terms of their ability to target the integrin-overexpressing U87 glioblastoma cell line in vitro. The GVs were chemically conjugated with the Alexa Fluor-488 fluorophore for visualization using confocal microscopy. GVs functionalized with RGD exhibited a marked increase in cell binding compared to controls (FIGS. 10C-10D). This technique presents a generalizable approach for future studies targeting GVs to molecular markers in vivo.

Using a similar engineering strategy, GvpC fusions was created to modulate the interaction of GVs with macrophages, which are both imaging targets and important actors in nanoparticle clearance from circulation. CD47, present on endogenous cell membranes in humans, mice, and other mammals, is a well-studied putative marker of self. Discher and colleagues recently described a minimized peptide from the human CD47 protein, dubbed the 'self' peptide, which led to reduced uptake of cells and nanoparticles by the mononuclear phagocytic system.[37] On the other hand, polycationic peptides such as polyarginine (R8) promote particle uptake by phagocytic cells.[38] By fusing each of these molecules to GvpC, we tested whether genetic engineering could modulate GV uptake in RAW 264.7 murine macrophages. As visualized by confocal microscopy, GVs genetically functionalized with GvpC$_{mCD47}$ showed reduced macrophage uptake compared to GVs with GvpC$_{WT}$. On the other hand, GVs functionalized with GvpC$_{R8}$ were taken up much more efficiently (FIGS. 10E-10F). These molecular strategies can be used in future studies to enable cellular labeling for in vivo tracking applications or to enhance the circulation lifetime of targeted GVs.

Figure 10G:
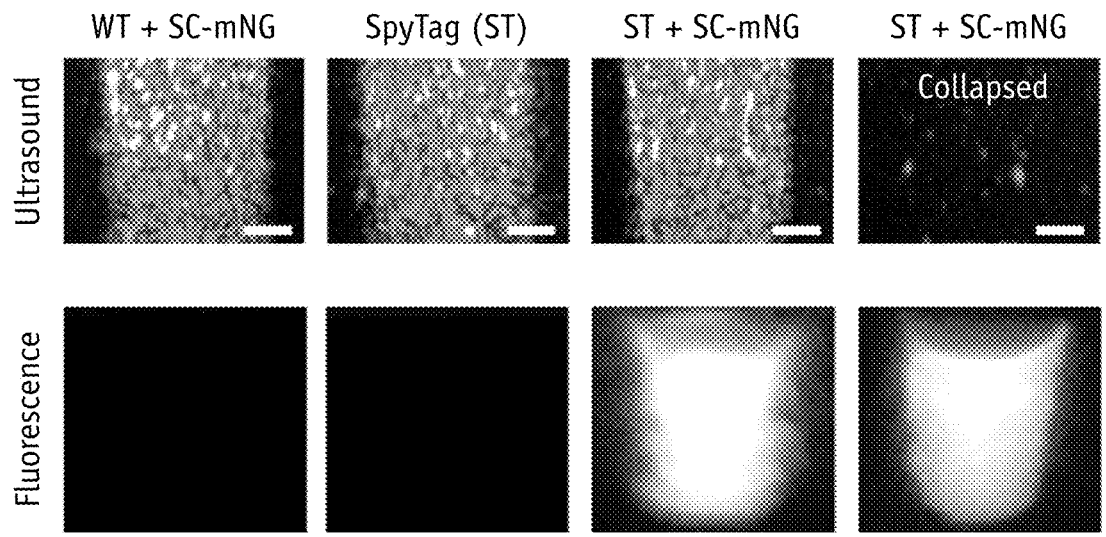
Figure 10H:
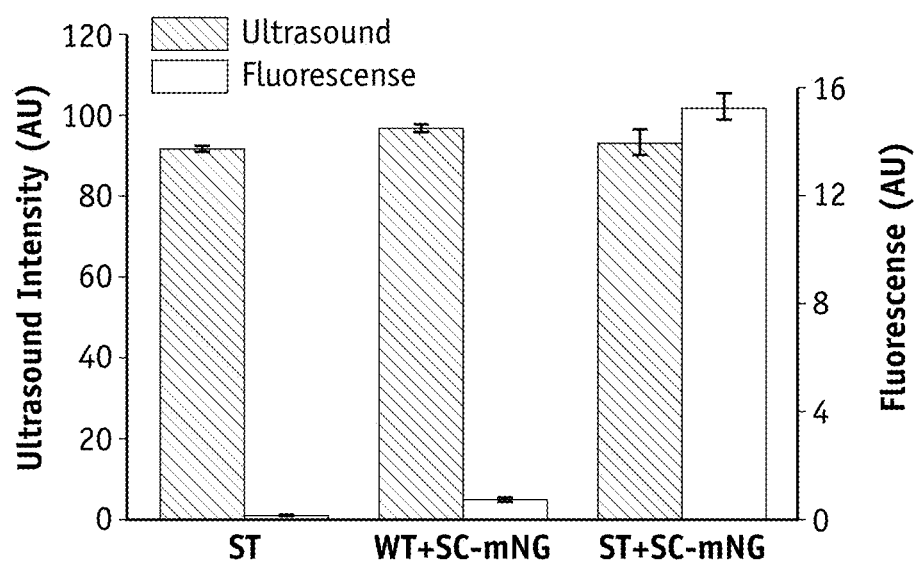
Figure 12:
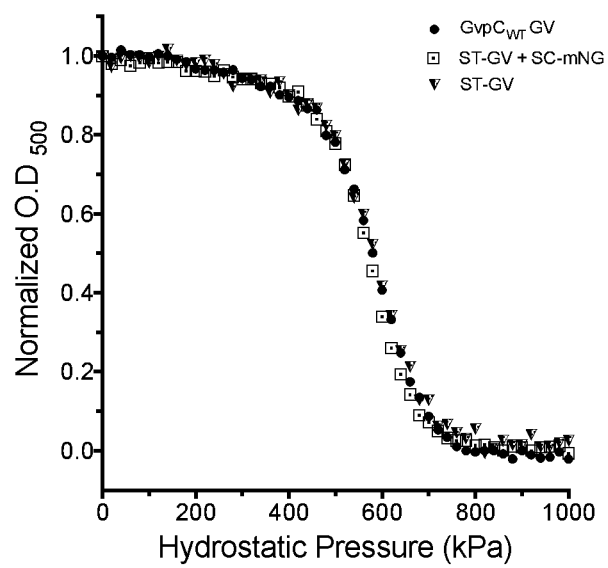
FIG. 12 shows a graph reporting exemplary optical density measurements of engineered Ana GVs as a function of hydrostatic pressure. The data was fitted with the Boltzmann sigmoid function $f(p)=(1+e^{(p-p_c)/\Delta p})^{-1}$ and the table provides the midpoint of collapse as well as other fit parameters and $R^2$ values. The data show that the collapse profile is unaltered even after reacting the ST-GVs with SC-mNG fluorescent protein.
Figure 13:
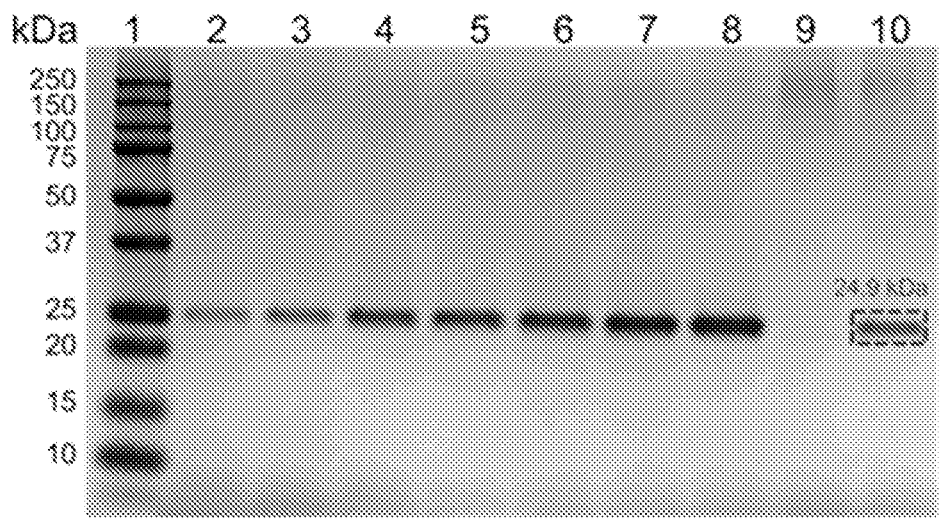
FIG. 13 shows an exemplary SDS-PAGE quantification of SpyTag functionalities on the surface of engineered Ana GVs. Comparison of ST-Ana GVs (lane 10) against a standard curve comprising GvpC-ST concentrations ranging from 100-1000 ng (lanes 2-8) shows that each modified GV has ~1000 SpyTag functionalities. Stripped Ana GVs used for GvpC-ST re-addition (lane 9) have negligible amount of native GvpC.
Figure 14:
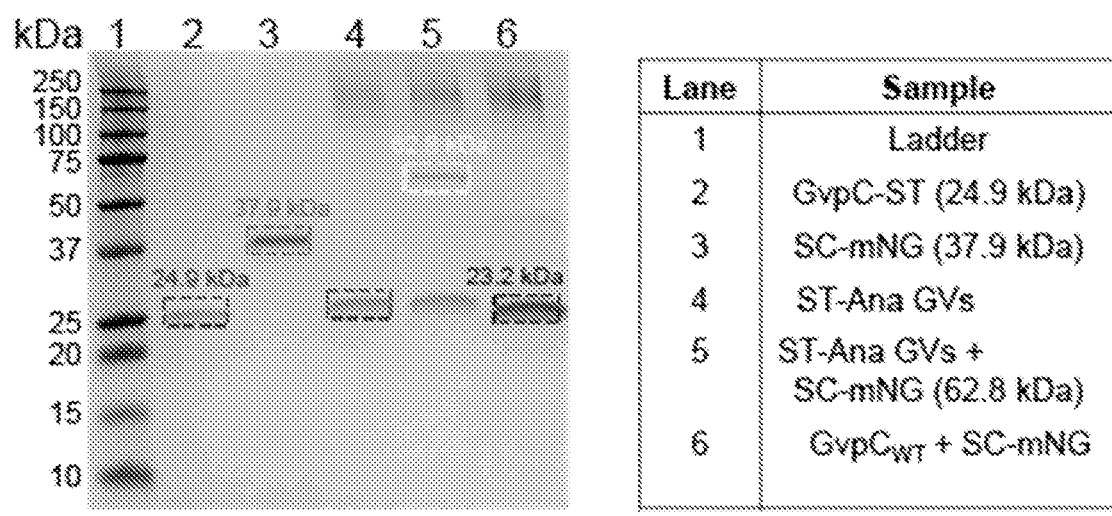
FIG. 14 shows SDS-PAGE analysis confirms SpyTag-SpyCatcher bond formation (dashed box around band in lane 5) upon a one-hour incubation of ST-GVs having an outer layer of GvpC-SpyTag (dashed boxes around bands in lanes 2 and 4) with SpyCatcher-mNeonGreen (dashed box around band in lane 3). Incubation of Ana GVs containing an outer layer of WT-GvpC (dashed box around band in lane 6) with SC-mNG, followed by buoyancy purification to remove unreacted fluorescent molecules results in GVs that are not fluorescent as shown in the left image in bottom row of images in FIG. 10G. This also highlights the specificity of the SpyTag-SpyCatcher reaction and confirms that all the unreacted fluorescent molecules are completely removed during buoyancy purification.

Finally, to further simplify future GV functionalization, a highly modular approach was developed, in which the GV surface can be specifically covalently conjugated to other recombinant proteins through a facile process that does not involve urea treatment and dialysis. To achieve this goal, GvpC was fused with SpyTag (ST), a 13-residue peptide that forms a covalent amide bond with a partner SpyCatcher protein under physiological conditions.[39] This system allows SpyTagged GVs to be functionalized with Spy-Catcher fusions in a rapid biocompatible reaction. It was found that GvpC$_{ST}$ binds to GVs with similar stoichiometry to GvpC$_{WT}$ and provides reinforcement against pressure-induced collapse (FIG. 12). Each modified GV had an average of 1,000 SpyTag functionalities (FIG. 13). To demonstrate the utility of this modular functionalization approach, these GVs were reacted with the recombinantly expressed fluorescent protein SpyCatcher-mNeonGreen (SC-mNG) to enable multimodal acoustic and fluorescent imaging. The resulting fluorescent GVs were purified by buoyancy enrichment. SDS-PAGE analysis confirmed Spy-Tag-SpyCatcher covalent bond formation (FIG. 14), and FIG. 10G shows multimodal imaging of mNG-labeled GVs with ultrasound and fluorescence. The ultrasound images show similar echogenicity between fluorescently-labeled GVs, wild-type and unreacted controls. GvpC$_{WT}$ Ana GVs do not show any fluorescence after reaction with SC-mNG (FIG. 10G), highlighting the specificity of the SpyTag-SpyCatcher reaction and confirming that buoyancy enrichment eliminates unreacted fluorescent proteins (FIG. 14). Notably, labeled ST-GVs remain fluorescent after acoustic pressure-induced collapse, which may be useful for follow-up histological examinations after ultrasound imaging. These results establish the GvpC$_{ST}$-SpyCatcher system as a highly modular and convenient approach to generate functionalized GVs, thereby enabling the first dual-mode imaging of these structures.

As shown in FIG. 17, attachments to the C-terminus appear to be tolerated well as it does not cause substantial decrease in collapse pressure as compared deleting the terminal regions. However, appending functional tag residues to the C-terminus of GvpCWT reduces collapse pressure depending on the length and exact properties of the amino acid sequence. Small sequences such as RGD and RDG do not appear to affect the collapse pressure to a substantial extent, however mCD47 and longer tags such as LRP (100 residues) reduce it to a greater extent. Also, Spytag-Spycatcher is a suitable method to functionalize GVs with big molecules such as fluorescent proteins without changing their collapse pressure (mechanical and acoustic properties).

Example 25: Engineering gvpC Variants in Species Other than *Anabaena flos-aquae*

It is expected that gvpC in other species can be engineered to produce variants in a similar manner to that described herein for *Anabaena flos-aquae*.

Evidence suggests that gvpC from different species may be functionally similar. For example, evidence from Buchholz et al. (1993) showed GVs from 3 different species can be stripped of its native GvpC to decrease hydrostatic collapse, and wild-type *Anabaena* GvpC can be re-added to all of them to enable an almost complete recovery of collapse pressure [27]

In addition, FIGS. 16A-16E show the wild-type amino acid GvpC sequences from 5 different organisms, where FIG. 16A shows *Halobacterium salinarum* gvpC, FIG. 16B shows *Anabaena flos-aquae* gvpC, FIG. 16C shows *Halobacterium mediterranei* gvpC, FIG. 16D shows *Microchaete diplosiphon* gvpC, and FIG. 16E shows *Nostoc* sp. gvpC. In each of these figures, sequences are shown with predicted aligned of the tandem repeat regions (Rep) within each gvpC protein, preceded by the N-terminal region (N-term) and followed by the C-terminal region (C-term).

Based on the structural similarity of gvpC from these five species, comprising repeated regions flanked by N- and C-terminal regions, it is expected that, as in *Anabaena flos-aquae* gvpC, engineering gvpC from these other species will enable production of variants that have altered hydrostatic and acoustic collapse pressure values and altered harmonic behavior compared to the wild-type gvpC, that will be useful for imaging applications. In particular, it is expected that removing repeats from the C-terminal end will typically have a lower effect on the collapse pressure compared to removing repeats close to the N-terminal end, that truncating the N-terminus of gvpc from these other species will decrease collapse pressure to a greater extent than truncating the C-terminal tail, and deleting N&C at the same time will produce GVs with lower collapse pressure than either truncation done separately.

It is also expected that adding molar excess of GvpC compared to gvpA prior to dialysis increases collapse pressure up to a certain threshold, above which the collapse pressure plateaus and does not increase any further. In addition, it is expected that appending a His-Tag to the N-terminus of the wild-type GvpC from these other species does not cause a substantial change in collapse pressure.

Appending tags to gvpC from these other species is also expected to result in functionalized gvpC variants with similar behaviors as described herein for gvpC from *Anabaena flos-aquae*.

Example 26: Exemplary GVs Producing Microorganisms

FIGS. 22A-22B show a list of GV producing microbes and FIG. 23 describes the different genes present in the gene cluster for haloarchael GVs (which have the largest number of different gyp genes) and their predicted function and features.

Example 27: Correspondence Between Hydrostatic Collapse Pressure and Acoustic Collapse Pressure In this example, hydrostatic and acoustic collapse pressures were measured for four GV types: Ana ΔGvpC, Ana ΔN&C, Ana WT, and Halo WT. The data is shown in Table 8.

TABLE 8

Measurement of hydrostatic and acoustic collapse pressures for four GV types

| GV Type | Hydrostatic Collapse Midpoint | Acoustic Collapse Midpoint |
|---|---|---|
| Ana ΔGvpC | 195.3 | 571 |
| Ana ΔN&C | 374.3 | 657.04 |
| Ana WT | 569.85 | 868.81 |
| Halo | 59 | 550 |

Figure 24:
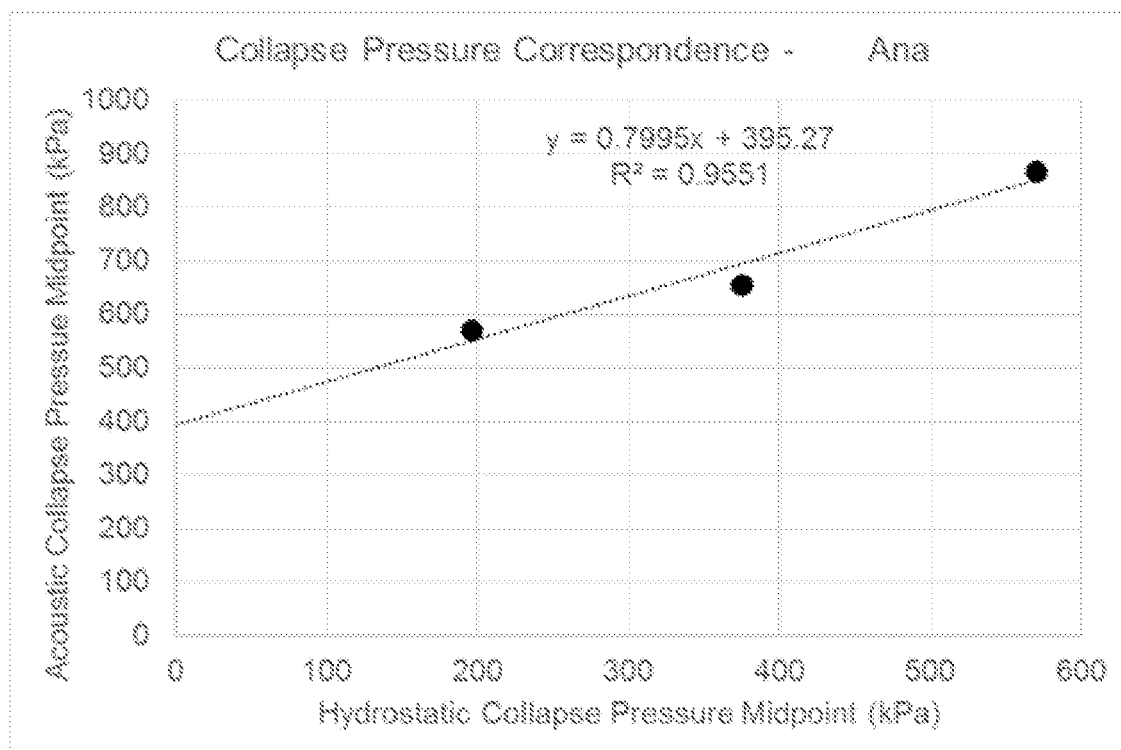
FIG. 24 shows a chart illustrating an exemplary diagram showing acoustic collapse pressure midpoints and hydrostatic collapse pressure midpoints for exemplary Ana GVs.

The collapse pressure correspondence between acoustic collapse pressure midpoints and hydrostatic collapse pressure midpoints for Ana GVs is plotted in FIG. 24, in which C is 395 and M is 0.8.

Figure 25:
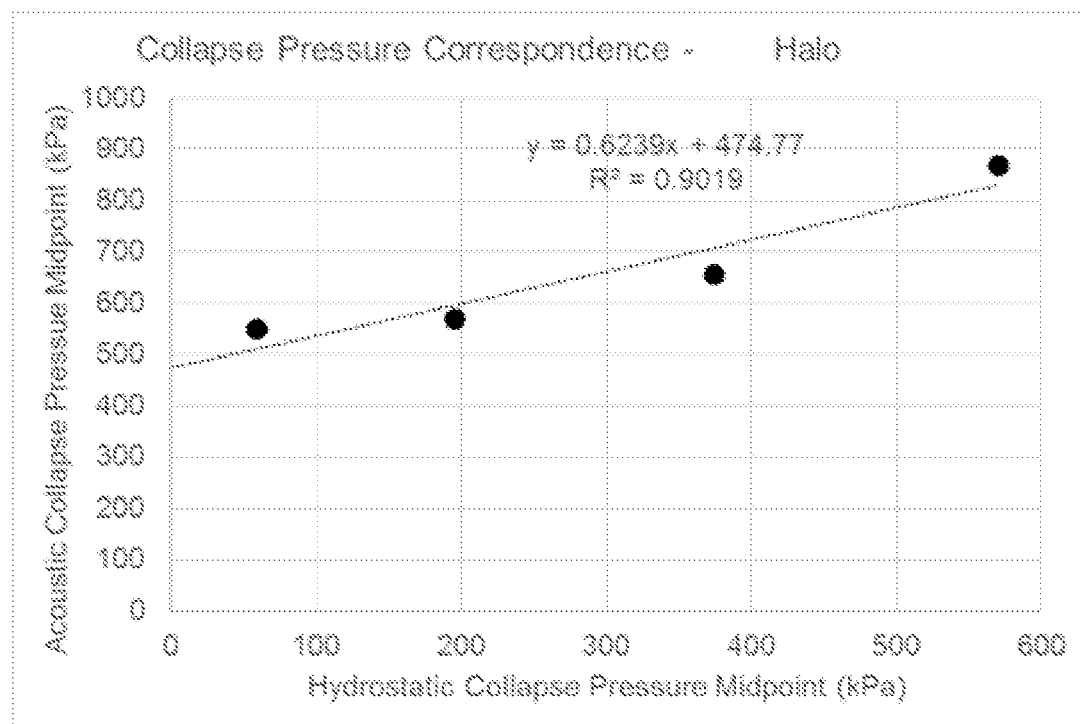
FIG. 25 shows a chart illustrating an exemplary diagram showing acoustic collapse pressure midpoints and hydrostatic collapse pressure midpoints for exemplary Halo GVs.

The collapse pressure correspondence between acoustic collapse pressure midpoints and hydrostatic collapse pressure midpoints for Halo GVs is plotted in FIG. 25. C is 475 and M is 0.64.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional gas vesicles, related components, genetic or chemical variants, as well as in compositions, methods and systems herein described, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Lakshmanan, A., et al., *Molecular Engineering of Acoustic Protein Nanostructures*. ACS Nano, 2016. 10(8): p. 7314-7322.
2. Pfeifer, F., *Distribution, formation and regulation of gas vesicles*. Nat. Rev. Microbiol., 2012. 10(10): p. 705-15.
3. Walsby, A. E., *Gas vesicles*. Microbiol. Rev., 1994. 58(1): p. 94-144.
4. Walsby, A. E., *Gas-vacuolate bacteria (apart from cyanobacteria)*, in *The Prokaryotes*. 1981, Springer. p. 441-447.
5. Walsby, A. E., *Cyanobacteria: planktonic gas-vacuolate forms*. The Prokaryotes, a Handbook on Habitats, Isolation, and Identification of Bacteria, 2013. 1: p. 224-235.
6. Woese, C. R., *Bacterial evolution*. Microbiological reviews, 1987. 51(2): p. 221.
7. Walsby, A. E., *Gas vesicles*. Microbiol Rev, 1994. 58(1): p. 94-144.
8. Hayes, P. and R. Powell, *The gvpA/C cluster of Anabaena flos-aquae has multiple copies of a gene encoding GvpA*. Archives of microbiology, 1995. 164(1): p. 50-57.
9. Kinsman, R. and P. Hayes, *Genes encoding proteins homologous to halobacterial Gvps N, J, K, F & L are located downstream of gvpC in the cyanobacterium Anabaena flos-aquae*. DNA Sequence, 1997. 7(2): p. 97-106.
10. Yi, G., S.-H. Sze, and M. R. Thon, *Identifying clusters of functionally related genes in genomes*. Bioinformatics, 2007. 23(9): p. 1053-1060.
11. Pfeifer, F., *Distribution, formation and regulation of gas vesicles*. Nat Rev Microbiol, 2012. 10(10): p. 705-15.
12. Myers, E. W. and W. Miller, *Optimal alignments in linear space*. Computer applications in the biosciences: CABIOS, 1988. 4(1): p. 11-17.
13. Smith, T. F. and M. S. Waterman, *Comparison of biosequences*. Advances in applied mathematics, 1981. 2(4): p. 482-489.
14. Needleman, S. B. and C. D. Wunsch, *A general method applicable to the search for similarities in the amino acid sequence of two proteins*. Journal of molecular biology, 1970. 48(3): p. 443-453.
15. Pearson, W. R. and D. J. Lipman, *Improved tools for biological sequence comparison*. Proceedings of the National Academy of Sciences, 1988. 85(8): p. 2444-2448.
16. Karlin, S. and S. F. Altschul, *Methods for assessing the statistical significance of molecular sequence features by using general scoring schemes*. Proceedings of the National Academy of Sciences, 1990. 87(6): p. 2264-2268.
17. Karlin, S. and S. F. Altschul, *Applications and statistics for multiple high-scoring segments in molecular sequences*. Proceedings of the National Academy of Sciences, 1993. 90(12): p. 5873-5877.
18. Li, N. and M. C. Cannon, *Gas vesicle genes identified in Bacillus megaterium and functional expression in Escherichia coli*. J Bacteriol, 1998. 180(9): p. 2450-8.
19. Maresca, D., et al., *Nonlinear Ultrasound Imaging of Nanoscale Acoustic Biomolecules*. Applied Physics Letters, 2017. 110(7).
20. Shapiro, M. G., et al., *Biogenic gas nanostructures as ultrasonic molecular reporters*. Nat. Nanotechnol., 2014. 9(4): p. 311-316.
21. Dawson, P. E., et al., *Synthesis of proteins by native chemical ligation*. Science, 1994. 266(5186): p. 776-780.
22. Nilsson, B. L., M. B. Soellner, and R. T. Raines, *Chemical synthesis of proteins*. Annu. Rev. Biophys. Biomol. Struct., 2005. 34: p. 91-118.
23. Zordan, R. E., et al., *Avoiding the ends: internal epitope tagging of proteins using transposon Tn7*. Genetics, 2015. 200(1): p. 47-58.

24. Cherin, E., et al., *Acoustic Behavior of Halobacterium salinarum Gas Vesicles in the High-Frequency Range: Experiments and Modeling*. Ultrasound in Medicine & Biology, 2017. 43(5): p. 1016-1030.
25. Maresca, D., et al., *Nonlinear ultrasound imaging of nanoscale acoustic biomolecules*. Applied Physics Letters, 2017. 110(7): p. 073704.
26. Shapiro, M. G., et al., *Genetically encoded reporters for hyperpolarized xenon magnetic resonance imaging*. Nat. Chem., 2014. 6(7): p. 629-634.
27. Buchholz, B., P. Hayes, and A. Walsby, *The distribution of the outer gas vesicle protein, GvpC, on the Anabaena gas vesicle, and its ratio to GvpA*. Microbiology, 1993. 139(10): p. 2353-2363.
28. Hayes, P., B. Buchholz, and A. Walsby, *Gas vesicles are strengthened by the outer-surface protein, GvpC*. Archives of microbiology, 1992. 157(3): p. 229-234.
29. Kinsman, R., A. Walsby, and P. Hayes, *GvpCs with reduced numbers of repeating sequence elements bind to and strengthen cyanobacterial gas vesicles*. Molecular microbiology, 1995. 17(1): p. 147-154.
30. Shapiro, M. G., et al., *Biogenic gas nanostructures as ultrasonic molecular reporters*. Nature nanotechnology, 2014. 9(4): p. 311.
31. Walsby, A. E., N. P. Revsbech, and D. H. Griffel, *The gas-permeability coefficient of the cyanobacterial gas vesicle wall*. Journal of General Microbiology, 1992. 138: p. 837-845.
32. Cherin, M., et al., *Acoustic behavior of Halobacterium salinarum gas vesicles in the high frequency range: experiments and modeling*. Submitted.
33. Burns, P. N., *Harmonic imaging with ultrasound contrast agents*. Clin. Radiol., 1996. 51: p. 50-55.
34. Maresca, D., et al., *Imaging microvasculature with contrast-enhanced ultraharmonic ultrasound*. Ultrasound in medicine & biology, 2014. 40(6): p. 1318-1328.
35. Blanco, E., H. Shen, and M. Ferrari, *Principles of nanoparticle design for overcoming biological barriers to drug delivery*. Nature biotechnology, 2015. 33(9): p. 941-951.
36. Ruoslahti, E., *RGD and other recognition sequences for integrins*. Annual review of cell and developmental biology, 1996. 12(1): p. 697-715.
37. Rodriguez, P. L., et al., *Minimal "Self" peptides that inhibit phagocytic clearance and enhance delivery of nanoparticles*. Science, 2013. 339(6122): p. 971-975.
38. Brock, R., *The uptake of arginine-rich cell-penetrating peptides: putting the puzzle together*. Bioconjugate chemistry, 2014. 25(5): p. 863-868.
39. Zakeri, B., et al., *Peptide tag forming a rapid covalent bond to a protein, through engineering a bacterial adhesin*. Proc. Natl. Acad. Sci. U.S.A, 2012. 109(12): p. E690-7.

The invention claimed is:

1. A system for multiplexed ultrasound imaging comprising:
a first contrast agent comprising a first set of purified gas vesicles (GVs) of a first gas vesicle protein structure (GVPS) type exhibiting a first acoustic collapse pressure profile and a first selectable acoustic collapse pressure value, and
a second contrast agent comprising a second set of purified GVs of a second GVPS type exhibiting a second acoustic collapse pressure profile and a second selectable acoustic collapse pressure value,
each GVPS type exhibiting a different acoustic collapse pressure profile defined as a collapse function from which a collapse amount can be determined and a different selectable acoustic collapse pressure value from their corresponding acoustic collapse pressure profile.

2. The system of claim 1, wherein the difference between the midpoint collapse pressure values of the first GVPS type and the midpoint collapse pressure values of the second GVPS type is at least 86 kPa.

3. The system of claim 1, wherein the percentage difference between the midpoint collapse pressure values of the first GVPS type and the midpoint collapse pressure values of the second GVPS type is at least twenty percent.

4. The system of claim 1, wherein at least one of the first GVPS type and the second GVPS type comprises a wild type GVPS type.

5. The system of claim 4, wherein the wild type GVPS type is from *Anabaena flosaquae* type, *Halobacteria salinarum* and/or *Bacillus megaterium*.

6. The system of claim 1 wherein at least one of the first GVPS type and the second GVPS type comprises an engineered variant of a wild type GVPS type.

7. The system of claim 6, wherein the engineered variant of the wild type GVPS type has a protein shell comprising a wild type GvpC of a different GVPS type than the wild type GVPS type.

8. The system of claim 6, wherein the engineered variant of the wild type GVPS type has a protein shell comprising a genetically modified GvpC variant of a same or different GVPS type than the wild type GVPS type.

9. The system of claim 6, wherein the engineered variant of the wild type GVPS type has a protein shell comprising a modified amount of a wild type GvpC of a same or different GVPS type than the wild type GVPS type.

10. The system of claim 6, wherein the engineered variant of the wild type GVPS type has a protein shell comprising a modified amount of an engineered GvpC variant of a same or different GVPS type than the wild type GVPS type.

11. The system of claim 6, wherein the engineered variant of a wild type GVPS type has a protein shell comprising at least one variant GvpC protein comprising one or more of:
a deletion of at least one of the N-terminal region and C-terminal region;
a deletion of 3 or more repeated regions;
a deletion of at least one repeated region immediately following the N-terminal region;
an addition to the C terminal or the N terminal region of an affinity tag, a chromatography tag, a lysine residue, an amine-reactive crosslinker, a fluorophore, and/or a cell targeting moiety; and
a substitution of a sub-sequence within one or more repeated regions.

12. The system of claim 6, wherein the engineered variant of a wild type GVPS type has a protein shell comprising a variant GvpC protein comprising one or more of: an addition to the C terminal or the N terminal region of an affinity tag, a chromatography tag, a lysine residue, an amine-reactive crosslinker, a fluorophore, and a cell targeting moiety.

13. The system of claim 6, wherein the engineered variant GVPS type comprises at least one variant GvpC protein comprising:
   one of SEQ ID NO: 6-10 or
   a sequence comprising repeats, wherein
      each repeat has a sequence length between 18 and 45 amino acids; greater than 50% of the repeats comprise a consensus sequence of at least 3 amino acids at a terminal end; and
      the repeats have a greater than 50% sequence similarity of the amino acids in each repeat of one of the SEQ ID NO: 6-10.

14. The system of claim 1, wherein the first GVPS type is selected from *Anabaena flosaquae* type or *Halobacteria salinarum* type and the second GVPS type is created by a heterologous expression of a gene cluster from *Bacillus megaterium* in *E. coli*.

15. The system of claim 1, wherein at least one of the first set of purified GVs and the second set of purified GVs comprised an engineered GvpC layer different than the native GvpC of that GVPS type.

16. The system of claim 15, wherein the engineered GvpC layer comprises one of $\Delta$GvpC, $\Delta$N&C and GvpC$_{WT}$ variants.

17. The system of claim 1, wherein the first GVPS type is engineered to be a $\Delta$GvpC variant of *Anabaena flosaquae* type and the second GVPS type is engineered to be a GvpC$_{WT}$ variant of *Anabaena flosaquae* type.

18. The system of claim 1, wherein at least one of the first contrast agent and the second contrast agent further comprises one or more of: water, physiological saline, balanced salt solutions, buffers, aqueous dextrose, and glycerol.

19. The system of claim 1, wherein at least one of the first contrast agent and the second contrast agent further comprises one or more of: a detergent, a wetting agent, an emulsifying agent, a dispersing agent, and a preservative.

20. The system of claim 1, further comprising an ultrasound imaging device.

21. The system of claim 20, wherein the ultrasound imaging device uses Doppler ultrasound imaging.

* * * * *

```
                              SEQUENCE LISTING

Sequence total quantity: 93
SEQ ID NO: 1           moltype = DNA  length = 585
FEATURE                Location/Qualifiers
source                 1..585
                       mol_type = genomic DNA
                       organism = Anabaena flos-aquae
CDS                    1..585
                       note = GvpC
SEQUENCE: 1
atgatttctt taatggcaaa aatccggcaa gaacatcagt caatagcaga gaaagtggct   60
gaactatctc ttgagaccag agaattcttg tccgtcacga cagcgaaaag acaagagcaa  120
gctgaaaaac aagctcaaga actgcaagca ttctacaagg atcttcagga aacaagtcag  180
cagttttat cagaaacagc ccaagccaga attgctcaag ctgaaaaaca agctcaagaa  240
ctgttagcat tccacaaaga acttcaagaa acaagtcagc agtttttatc agcaacagcc  300
caagccagaa ttgctcaagc tgaaaaacaa gcgcaagaac tgttagcatt ttatcaagaa  360
gttcgggaaa caagtcagca gttttttatca gcaacagccc aagcaagaat tgctcaagct  420
gaaaaacaag ctcaagaact gttagcattc cacaaagaac ttcaagaaac aagtcagcag  480
tttttatcag caacagccga cgcaagaact gctcaagcta aggaacagaa ggaatctctc  540
ctgaaattcc gtcaggattt gtttgtgagt atctttggtt aataa               585

SEQ ID NO: 2           moltype = AA   length = 193
FEATURE                Location/Qualifiers
source                 1..193
                       mol_type = protein
                       organism = Anabaena flos-aquae
SEQUENCE: 2
MISLMAKIRQ EHQSIAEKVA ELSLETREFL SVTTAKRQEQ AEKQAQELQA FYKDLQETSQ   60
QFLSETAQAR IAQAEKQAQE LLAFHKELQE TSQQFLSATA QARIAQAEKQ AQELLAFYQE  120
VRETSQQFLS ATAQARIAQA EKQAQELLAF HKELQETSQQ FLSATADART AQAKEQKESL  180
LKFRQDLFVS IFG                                                    193

SEQ ID NO: 3           moltype = DNA   length = 1149
FEATURE                Location/Qualifiers
source                 1..1149
                       mol_type = genomic DNA
                       organism = Halobacterium salinarum
CDS                    1..1149
                       note = GvpC
SEQUENCE: 3
atgagtgtca cagacaaacg cgacgagatg agtactgccc gcgataagtt cgcagaatca   60
cagcaggagt tcgaatcata cgctgacgag tttgcagccg atatcacggc aaagcaagac  120
gatgtcagcg accttgtcga tgcgatcacc gacttccagg cggagatgac caacacgacg  180
gatgcatttc acacatatgg tgacgagttc gccgctgagg ttgaccacct ccgtgccgat  240
attgacgccc agcgggacgt gatccgtgag atgcaggatg cgttcgaggc atatgctgac  300
```

-continued

```
atcttcgcta cagatatcgc agacaaacaa gatatcggca atcttctggc tgcgattgag   360
gcgctccgaa cagagatgaa ctcaaccac ggggcattcg aagcatatgc ggacgacttc    420
gcagccgatg tcgctgcgct ccgtgatata tctgatctgg ttgcagcaat cgacgacttc   480
caagaggaat tcatcgccgt gcaggacgca tttgacaact acgctggtga cttcgatgcg   540
gagatcgacc agctccacgc tgccatcgct gaccagcacg acagcttcga cgctaccgcg   600
gacgccttcg cagagtaccg agatgagttc tatcgcatag aggtggaagc actgcttgag   660
gcgatcaacg acttccagca ggacatcggt gacttccgag cggagtttga aacgactgag   720
gacgcgttcg ttgccttcgc ccgtgacttc tatggccacg agatcacggc cgaggaaggc   780
gccgccgaag cggaagccga acccgtcgag gctgacgcgg acgtcgaagc ggaagcagaa   840
gtctctctccag acgaagctgg cggagaatcc gccggtaccg aggaagaaga gacagagccg  900
gccgaggtgg aaacgcggc tccagaagta gaggggagtc ctgcggacac ggcagacgaa   960
gcggaagata cggaagcaga ggaggagaca gaggaagagg caccggaaga catggtgcag  1020
tgccgggtgt gcggcgaata ctatcaggcc atcacggagc ccatctcca gacccatgat  1080
atgacgattc aggagtaccg cgacgagtac ggtgaggatg tcccccttcg gccggatgat 1140
aaacatga                                                          1149

SEQ ID NO: 4          moltype = AA  length = 382
FEATURE               Location/Qualifiers
source                1..382
                      mol_type = protein
                      organism = Halobacterium salinarum
SEQUENCE: 4
MSVTDKRDEM STARDKFAES QQEFESYADE FAADITAKQD DVSDLVDAIT DFQAEMTNTT    60
DAFHTYGDEF AAEVDHLRAD IDAQRDVIRE MQDAFEAYAD IFATDIADKQ DIGNLLAAIE   120
ALRTEMNSTH GAFEAYADDF AADVAALRDI SDLVAAIDDF QEEFIAVQDA FDNYAGDFDA   180
EIDQLHAAIA DQHDSFDATA DAFAEYRDEF YRIEVEALLE AINDFQQDIG DFPRAEFETTE  240
DAFVAFARDF YGHEITAEEG AAEAEAEPVE ADADVEAEAE VSPDEAGGES AGTEEEETEP   300
AEVETAAPEV EGSPADTADE AEDTEAEEET EEEAPEDMVQ CRVCGEYYQA ITEPHLQTHD   360
MTIQEYRDEY GEDVPLRPDD KT                                           382

SEQ ID NO: 5          moltype = DNA  length = 1146
FEATURE               Location/Qualifiers
source                1..1146
                      mol_type = genomic DNA
                      organism = Halobacterium mediterranei
CDS                   1..1146
                      note = GvpC
SEQUENCE: 5
atgagtgtca aagacaaacg tgaaaagatg accgccaccc gcgaggaatt cgcggaagta    60
cagcaagcgt tcgcggccta tgccgacgag ttcgctgccg atgttgacga taaacgagac   120
gtaagcgaac tcgtcgatgg gattgatacc ctgcggacgg agatgaacag cactaacgat   180
gcgtttcgtg catacagtga ggaattcgcc gccgacgtcg agcacttcca tacgtcggtt   240
gctgaccgac gcgacgcctt cgacgcgtat gccgacattt cgttcgacga tgtcgcggag   300
atgcaggatg tgagtgacct cctcgccgca atagacgacc tccgggcgga gatggacgaa   360
actcacgaag cgttcgacgc ctacgcggat gcattcgtga ccgacgtggc tacccttcgc   420
gatgtgtcgg acctgctgac ggcgatttcg gaactccagt cggaattcgt ctctgtgcag   480
ggcgaattta acggctacgc tagtgagttc ggtgccgaca tcgaccagtt ccacgcgtt    540
gtcgccgaaa aacgcgatgg tcacaaagac gttgctgacg ccttcctcca gtaccgagag   600
gaatttcacg cgtcgaggt acagtcctta ttggacaaca tcgctgcctt ccagcgagaa   660
atgggggact accggaaagc gttcgaaacg actgaggaag cgttcgcctc cttcgctcgc   720
gacttctacg ggcagggcgc tgctcccatg gcgacaccct tgaacaacgc ggctgaaaca   780
gccgtgactg gcacggagac cgaggtagac atacctccga tagaagactc cgtagaaccc   840
gacggtgaag acgaggactc gaaagcagat gacgtcgaag ccgaagccga agtcgagacg   900
gtagaaatgg agttcggtgc ggagatggac acagaagccg acgaagacgt ccaatcggag   960
tcggtcagag aagacgacca gttcctggac gacgagcaga cagaggatat ggtccagtgt  1020
ctggtgtgcg gcgaatatta tcaggcgatt acagaaccc accttcagac acgacatg   1080
acgatcaaga aataccgcga agagtacggc gaggacgtgc actccgccc ggatgataaa  1140
gcatga                                                             1146

SEQ ID NO: 6          moltype = AA  length = 381
FEATURE               Location/Qualifiers
source                1..381
                      mol_type = protein
                      organism = Halobacterium mediterranei
SEQUENCE: 6
MSVKDKREKM TATREEFAEV QQAFAAYADE FAADVDDKRD VSELVDGIDT LRTEMNSTND    60
AFRAYSEEFA ADVEHFHTSV ADRRDAFDAY ADIFATDVAE MQDVSDLLAA IDDLRAEMDE   120
THEAFDAYAD AFVTDVATLR DVSDLLTAIS ELQESEFVSVQ GEFNGYASEF GADIDQPHAV  180
VAEKRDGHKD VADAFLQYRE EFHGVEVQSL LDNIAAFQRE MGDYRKAFET TEEEAFASFAR  240
DFYGQGAAPM ATPLNNAAET AVTGTETEVD IPPIEDSVEP DGEDEDSKAD DVEAEAEVET   300
VEMEFGAEMD TEADEDVQSE SVREDDQFLD DETPEDMVQC LVCGEYYQAI TEPHLQTHDM   360
TIKKYREEYG EDVPLRPDDK A                                            381

SEQ ID NO: 7          moltype = DNA  length = 489
FEATURE               Location/Qualifiers
source                1..489
                      mol_type = genomic DNA
                      organism = Microchaete diplosiphon
CDS                   1..489
```

-continued

```
                        note = GvpC
SEQUENCE: 7
atgactcctt taatgatcag aatccggcaa gagcatcgag gaatagcaga ggaagtaact    60
caactattta aagatactca agaattcttg tccgtgacca cagcgcaaag acaagcgcaa   120
gctaaagaac aagctgaaaa tctgcatcag ttccataagg atctggagaa agacactgaa   180
gagtttttaa cagatacagc taaagaaaga atggctaaag ccaaacagca agctgaagat   240
ctgttccaat tccataagga aatggcagaa acacccaag agttttttgtc agaaacagct   300
aaagaaagaa tggcgcaagc tcaagagcaa gctcgacaat tgcgcgaatt ccatcaaaac   360
cttgagcaaa caaccaacga atttttagct gacacagcta agaaagaat ggcgcaagct   420
caagaacaaa aacaacagct acatcaattc cgtcaggatt tgtttgctag cattttggt    480
acatttttag                                                          489

SEQ ID NO: 8            moltype = AA  length = 162
FEATURE                 Location/Qualifiers
source                  1..162
                        mol_type = protein
                        organism = Microchaete diplosiphon
SEQUENCE: 8
MTPLMIRIRQ EHRGIAEEVT QLFKDTQEFL SVTTAQRQAQ AKEQAENLHQ FHKDLEKDTE    60
EFLTDTAKER MAKAKQQAED LFQFHKEMAE NTQEFLSETA KERMAQAQEQ ARQLREFHQN   120
LEQTTNEFLA DTAKERMAQA QEQKQQLHQF RQDLFASIFG TF                      162

SEQ ID NO: 9            moltype = DNA  length = 390
FEATURE                 Location/Qualifiers
source                  1..390
                        mol_type = genomic DNA
                        organism = Nostoc sp.
CDS                     1..390
                        note = GvpC
SEQUENCE: 9
atgacggctt taatggtaag aatccggcaa gagcatcggt cgatagctga ggaagtaact    60
caactattta gagagactca tgaattcttg tccgctacaa cagcacacag acaagagcaa   120
gccaaacagc aagcgcaaca gctacatcag ttccaccaaa atctggagca gacaacccac   180
gagttttta cagaaaccac aacacaaagg gttgctcaag ctgaagcaaa ggcaaaatt    240
ttgcataagt ttcaccaaaa tctagaacag accacccaag agtttctagc agaaacagca   300
aaaaacagaa ctgagcaagc caaagcacaa agtcaatatc tgcaacaatt tcgtaaggat   360
ttgtttgcta gtattttttgg cacatttttag                                  390

SEQ ID NO: 10           moltype = AA  length = 129
FEATURE                 Location/Qualifiers
source                  1..129
                        mol_type = protein
                        organism = Nostoc sp.
SEQUENCE: 10
MTALMVRIRQ EHRSIAEEVT QLFRETHEFL SATTAHRQEQ AKQQAQQLHQ FHQNLEQTTH    60
EFLTETTTQR VAQAEAQANF LHKFHQNLEQ TTQEFLAETA KNRTEQAKAQ SQYLQQFRKD   120
LFASIFGTF                                                           129

SEQ ID NO: 11           moltype = AA  length = 15
FEATURE                 Location/Qualifiers
REGION                  1..15
                        note = Synthetic construct
REGION                  1..15
                        note = MISC_FEATURE - AviTag
source                  1..15
                        mol_type = protein
                        organism = synthetic construct
SEQUENCE: 11
GLNDIFEAQK IEWHE                                                     15

SEQ ID NO: 12           moltype = AA  length = 26
FEATURE                 Location/Qualifiers
REGION                  1..26
                        note = Synthethic contruct
REGION                  1..26
                        note = MISC_FEATURE - Calmodulin-tag
source                  1..26
                        mol_type = protein
                        organism = synthetic construct
SEQUENCE: 12
KRRWKKNFIA VSAANRFKKI SSSGAL                                         26

SEQ ID NO: 13           moltype = AA  length = 6
FEATURE                 Location/Qualifiers
REGION                  1..6
                        note = Synthethic construct
REGION                  1..6
                        note = MISC_FEATURE - polyglutamate tag
source                  1..6
```

```
                            mol_type = protein
                            organism = synthetic construct
SEQUENCE: 13
EEEEEE                                                              6

SEQ ID NO: 14               moltype = AA   length = 13
FEATURE                     Location/Qualifiers
REGION                      1..13
                            note = Synthetic construct
REGION                      1..13
                            note = MISC_FEATURE - E-tag
source                      1..13
                            mol_type = protein
                            organism = synthetic construct
SEQUENCE: 14
GAPVPYPDPL EPR                                                      13

SEQ ID NO: 15               moltype = AA   length = 8
FEATURE                     Location/Qualifiers
REGION                      1..8
                            note = Synthetic construct
REGION                      1..8
                            note = MISC_FEATURE - FLAG-tag
source                      1..8
                            mol_type = protein
                            organism = synthetic construct
SEQUENCE: 15
DYKDDDDK                                                            8

SEQ ID NO: 16               moltype = AA   length = 9
FEATURE                     Location/Qualifiers
REGION                      1..9
                            note = Synthethic construct
REGION                      1..9
                            note = MISC_FEATURE - HA-tag
source                      1..9
                            mol_type = protein
                            organism = synthetic construct
SEQUENCE: 16
YPYDVPDYA                                                           9

SEQ ID NO: 17               moltype = AA   length = 6
FEATURE                     Location/Qualifiers
REGION                      1..6
                            note = Synthetic construct
REGION                      1..6
                            note = MISC_FEATURE - His-tag
source                      1..6
                            mol_type = protein
                            organism = synthetic construct
SEQUENCE: 17
HHHHHH                                                              6

SEQ ID NO: 18               moltype = AA   length = 10
FEATURE                     Location/Qualifiers
REGION                      1..10
                            note = Synthetic construct
REGION                      1..10
                            note = MISC_FEATURE - Myc-tag
source                      1..10
                            mol_type = protein
                            organism = synthetic construct
SEQUENCE: 18
EQKLISEEDL                                                          10

SEQ ID NO: 19               moltype = AA   length = 18
FEATURE                     Location/Qualifiers
REGION                      1..18
                            note = Synthetic construct
REGION                      1..18
                            note = MISC_FEATURE - NE-tag
source                      1..18
                            mol_type = protein
                            organism = synthetic construct
SEQUENCE: 19
TKENPRSNQE ESYDDNES                                                 18

SEQ ID NO: 20               moltype = AA   length = 15
FEATURE                     Location/Qualifiers
```

```
                                   REGION              1..15
                                                       note = Synthethic construct
                                   REGION              1..15
                                                       note = MISC_FEATURE - S-tag
                                   source              1..15
                                                       mol_type = protein
                                                       organism = synthetic construct
SEQUENCE: 20
KETAAAKFER QHMDS                                                                                      15

SEQ ID NO: 21      moltype = AA   length = 38
                                   FEATURE            Location/Qualifiers
                                   REGION             1..38
                                                      note = Synthethic construct
                                   REGION             1..38
                                                      note = MISC_FEATURE - SBP-tag
                                   source             1..38
                                                      mol_type = protein
                                                      organism = synthetic construct
SEQUENCE: 21
MDEKTTGWRG GHVVEGLAGE LEQLRARLEH HPQGQREP                                                             38

SEQ ID NO: 22      moltype = AA   length = 13
                                   FEATURE            Location/Qualifiers
                                   REGION             1..13
                                                      note = Synthethic construct
                                   REGION             1..13
                                                      note = MISC_FEATURE - Softag 1
                                   source             1..13
                                                      mol_type = protein
                                                      organism = synthetic construct
SEQUENCE: 22
SLAELLNAGL GGS                                                                                        13

SEQ ID NO: 23      moltype = AA   length = 8
                                   FEATURE            Location/Qualifiers
                                   REGION             1..8
                                                      note = Synthetic construct
                                   REGION             1..8
                                                      note = MISC_FEATURE - Softag 3
                                   source             1..8
                                                      mol_type = protein
                                                      organism = synthetic construct
SEQUENCE: 23
TQDPSRVG                                                                                               8

SEQ ID NO: 24      moltype = AA   length = 8
                                   FEATURE            Location/Qualifiers
                                   REGION             1..8
                                                      note = Synthethic construct
                                   REGION             1..8
                                                      note = MISC_FEATURE - Strep-tag
                                   source             1..8
                                                      mol_type = protein
                                                      organism = synthetic construct
SEQUENCE: 24
WSHPQFEK                                                                                               8

SEQ ID NO: 25      moltype = AA   length = 6
                                   FEATURE            Location/Qualifiers
                                   REGION             1..6
                                                      note = Synthethic construct
                                   REGION             1..6
                                                      note = MISC_FEATURE - TC tag
                                   source             1..6
                                                      mol_type = protein
                                                      organism = synthetic construct
SEQUENCE: 25
CCPGCC                                                                                                 6

SEQ ID NO: 26      moltype = AA   length = 14
                                   FEATURE            Location/Qualifiers
                                   REGION             1..14
                                                      note = Synthethic construct
                                   REGION             1..14
                                                      note = MISC_FEATURE - V5 tag
                                   source             1..14
                                                      mol_type = protein
                                                      organism = synthetic construct
```

```
SEQUENCE: 26
GKPIPNPLLG LDST                                                            14

SEQ ID NO: 27           moltype = AA  length = 11
FEATURE                 Location/Qualifiers
REGION                  1..11
                        note = Synthetic construct
REGION                  1..11
                        note = MISC_FEATURE - VSV-tag
source                  1..11
                        mol_type = protein
                        organism = synthetic construct
SEQUENCE: 27
YTDIEMNRLG K                                                               11

SEQ ID NO: 28           moltype = AA  length = 8
FEATURE                 Location/Qualifiers
REGION                  1..8
                        note = Synthetic construct
REGION                  1..8
                        note = MISC_FEATURE - Xpress tag
source                  1..8
                        mol_type = protein
                        organism = synthetic construct
SEQUENCE: 28
DLYDDDDK                                                                    8

SEQ ID NO: 29           moltype = AA  length = 16
FEATURE                 Location/Qualifiers
REGION                  1..16
                        note = Synthetic construct
REGION                  1..16
                        note = MISC_FEATURE - Isopeptag
source                  1..16
                        mol_type = protein
                        organism = synthetic construct
SEQUENCE: 29
TDKDMTITFT NKKDAE                                                          16

SEQ ID NO: 30           moltype = AA  length = 13
FEATURE                 Location/Qualifiers
REGION                  1..13
                        note = Synthetic construct
REGION                  1..13
                        note = MISC_FEATURE - SpyTag
source                  1..13
                        mol_type = protein
                        organism = synthetic construct
SEQUENCE: 30
AHIVMVDAYK PTK                                                             13

SEQ ID NO: 31           moltype = AA  length = 12
FEATURE                 Location/Qualifiers
REGION                  1..12
                        note = Synthetic construct
REGION                  1..12
                        note = MISC_FEATURE - SnoopTag
source                  1..12
                        mol_type = protein
                        organism = synthetic construct
SEQUENCE: 31
KLGDIEFIKV NK                                                              12

SEQ ID NO: 32           moltype = AA  length = 8
FEATURE                 Location/Qualifiers
REGION                  1..8
                        note = MISC_FEATURE - Exemplary consensus sequence in GvpC
                         repeat
source                  1..8
                        mol_type = protein
                        organism = Anabaena flos-aquae
SEQUENCE: 32
QAQELLAF                                                                    8

SEQ ID NO: 33           moltype = AA  length = 4
FEATURE                 Location/Qualifiers
REGION                  1..4
                        note = MISC_FEATURE - Exemplary consensus sequence in GvpC
                         repeat
```

```
source                      1..4
                            mol_type = protein
                            organism = Microchaete diplosiphon
SEQUENCE: 33
LHQF                                                                        4

SEQ ID NO: 34               moltype = AA  length = 4
FEATURE                     Location/Qualifiers
REGION                      1..4
                            note = MISC_FEATURE - Exemplary consensus sequence in GvpC
                             repeat
source                      1..4
                            mol_type = protein
                            organism = Microcystis aeruginosa
SEQUENCE: 34
LSQF                                                                        4

SEQ ID NO: 35               moltype = AA  length = 190
FEATURE                     Location/Qualifiers
REGION                      1..190
                            note = Synthethic construct
REGION                      1..190
                            note = MISC_FEATURE - Exemplary genetically engineered GvpC
                             variant deltaN&C-CERY1
source                      1..190
                            mol_type = protein
                            organism = synthetic construct
SEQUENCE: 35
MGHHHHHHSG VAELSLETRE FLSVTTAKRQ EQAEKQAQEL QAFYKDLQET SQQFLSETAQ          60
ARIAQAEKQA QELLAFHKEL QETSQQFLSA TAQARIAQAE KQAQELLAFY QEVRETSQQF         120
LSATAQARIA QAEKQAQELL AFHKELQETS QQFLSATADA RTAQAKEQKE SLLKFGSGWM         180
VLPWLPGTLD                                                               190

SEQ ID NO: 36               moltype = AA  length = 186
FEATURE                     Location/Qualifiers
REGION                      1..186
                            note = Synthetic construct
REGION                      1..186
                            note = MISC_FEATURE - Exemplary genetically engineered GvpC
                             variant deltaNterm
source                      1..186
                            mol_type = protein
                            organism = synthetic construct
SEQUENCE: 36
MGVAELSLET REFLSVTTAK RQEQAEKQAQ ELQAFYKDLQ ETSQQFLSET AQARIAQAEK          60
QAQELLAFHK ELQETSQQFL SATAQARIAQ AEKQAQELLA FYQEVRETSQ QFLSATAQAR         120
IAQAEKQAQE LLAFHKELQE TSQQFLSATA DARTAQAKEQ KESLLKFRQD LFVSIFGSLE         180
HHHHHH                                                                   186

SEQ ID NO: 37               moltype = AA  length = 70
FEATURE                     Location/Qualifiers
REGION                      1..70
                            note = Synthetic construct
REGION                      1..70
                            note = MISC_FEATURE - Exemplary genetically engineered GvpC
                             variant N-rep3-C
source                      1..70
                            mol_type = protein
                            organism = synthetic construct
SEQUENCE: 37
MISLMAKIRQ EHQSIAEKHK ELQETSQQFL SATAQARIAQ AEKQAQELLA FRQDLFVSIF          60
GSLEHHHHHH                                                                70

SEQ ID NO: 38               moltype = AA  length = 84
FEATURE                     Location/Qualifiers
REGION                      1..84
                            note = Synthetic construct
REGION                      1..84
                            note = MISC_FEATURE - Exemplary genetically engineered GvpC
                             variant SR3CERY1
source                      1..84
                            mol_type = protein
                            organism = synthetic construct
SEQUENCE: 38
MGHHHHHHSG ISLMAKIRQE HQSIAEKHKE LQETSQQFLS ATAQARIAQA EKQAQELLAF          60
RQDLFVSIFG SGWMVLPWLP GTLD                                                84

SEQ ID NO: 39               moltype = AA  length = 216
FEATURE                     Location/Qualifiers
```

```
REGION                  1..216
                        note = Synthetic construct
REGION                  1..216
                        note = MISC_FEATURE - Exemplary genetically engineered GvpC
                         variant WTCERY1
source                  1..216
                        mol_type = protein
                        organism = synthetic construct
SEQUENCE: 39
MGHHHHHHSG ISLMAKIRQE HQSIAEKVAE LSLETREFLS VTTAKRQEQA EKQAQELQAF    60
YKDLQETSQQ FLSETAQARI AQAEKQAQEL LAFHKELQET SQQFLSATAQ ARIAQAEKQA   120
QELLAFYQEV RETSQQFLSA TAQARIAQAE KQAQELLAFH KELQETSQQF LSATADARTA   180
QAKEQKESLL KFRQDLFVSI FGSGWMVLPW LPGTLD                            216

SEQ ID NO: 40           moltype = AA  length = 71
FEATURE                 Location/Qualifiers
REGION                  1..71
                        note = Synthetic construct
REGION                  1..71
                        note = MISC_FEATURE - Exemplary genetically engineered GvpC
                         variant N-rep1-C
source                  1..71
                        mol_type = protein
                        organism = synthetic construct
SEQUENCE: 40
MGISLMAKIR QEHQSIAEKV AELSLETREF LSVTTAKRQE QAEKQAQELQ AFRQDLFVSI    60
FGSLEHHHHH H                                                        71

SEQ ID NO: 41           moltype = AA  length = 84
FEATURE                 Location/Qualifiers
REGION                  1..84
                        note = Synthetic construct
REGION                  1..84
                        note = MISC_FEATURE - Exemplary genetically engineered GvpC
                         variant SR1CERY1
source                  1..84
                        mol_type = protein
                        organism = synthetic construct
SEQUENCE: 41
MGHHHHHHSG ISLMAKIRQE HQSIAEKVAE LSLETREFLS VTTAKRQEQA EKQAQELQAF    60
RQDLFVSIFG SGWMVLPWLP GTLD                                          84

SEQ ID NO: 42           moltype = AA  length = 176
FEATURE                 Location/Qualifiers
REGION                  1..176
                        note = Synthetic construct
REGION                  1..176
                        note = MISC_FEATURE - Exemplary genetically engineered GvpC
                         variant deltaN&C
source                  1..176
                        mol_type = protein
                        organism = synthetic construct
SEQUENCE: 42
MGVAELSLET REFLSVTTAK RQEQAEKQAQ ELQAFYKDLQ ETSQQFLSET AQARIAQAEK    60
QAQELLAFHK ELQETSQQFL SATAQARIAQ AEKQAQELLA FYQEVRETSQ QFLSATAQAR   120
IAQAEKQAQE LLAFHKELQE TSQQFLSATA DARTAQAKEQ KESLLKFSLE HHHHHH       176

SEQ ID NO: 43           moltype = AA  length = 64
FEATURE                 Location/Qualifiers
REGION                  1..64
                        note = Synthetic construct
REGION                  1..64
                        note = MISC_FEATURE - Exemplary genetically engineered GvpC
                         variant N-rep2endto3mid-C
source                  1..64
                        mol_type = protein
                        organism = synthetic construct
SEQUENCE: 43
MISLMAKIRQ EHQSIAEKQA QELLAFHKEL QETSQQFLSA TAQARRQDLF VSIFGSLEHH    60
HHHH                                                                64

SEQ ID NO: 44           moltype = AA  length = 202
FEATURE                 Location/Qualifiers
REGION                  1..202
                        note = Synthetic construct
REGION                  1..202
                        note = MISC_FEATURE - Exemplary genetically engineered GvpC
                         variant N-His-GvpC
source                  1..202
```

```
                        mol_type = protein
                        organism = synthetic construct
SEQUENCE: 44
MGHHHHHHSG ISLMAKIRQE HQSIAEKVAE LSLETREFLS VTTAKRQEQA EKQAQELQAF     60
YKDLQETSQQ FLSETAQARI AQAEKQAQEL LAFHKELQET SQQFLSATAQ ARIAQAEKQA    120
QELLAFYQEV RETSQQFLSA TAQARIAQAE KQAQELLAFH KELQETSQQF LSATADARTA    180
QAKEQKESLL KFRQDLFVSI FG                                             202

SEQ ID NO: 45           moltype = AA   length = 190
FEATURE                 Location/Qualifiers
REGION                  1..190
                        note = Synthetic construct
REGION                  1..190
                        note = MISC_FEATURE - Exemplary genetically engineered GvpC
                         variant deltaCterm
source                  1..190
                        mol_type = protein
                        organism = synthetic construct
SEQUENCE: 45
MGISLMAKIR QEHQSIAEKV AELSLETREF LSVTTAKRQE QAEKQAQELQ AFYKDLQETS     60
QQFLSETAQA RIAQAEKQAQ ELLAFHKELQ ETSQQFLSAT AQARIAQAEK QAQELLAFYQ    120
EVRETSQQFL SATAQARIAQ AEKQAQELLA FHKELQETSQ QFLSATADAR TAQAKEQKES    180
LLKFHHHHHH                                                           190

SEQ ID NO: 46           moltype = AA   length = 230
FEATURE                 Location/Qualifiers
REGION                  1..230
                        note = Synthetic construct
REGION                  1..230
                        note = MISC_FEATURE - Exemplary genetically engineered GvpC
                         variant GvpCWT-ACPP
source                  1..230
                        mol_type = protein
                        organism = synthetic construct
SEQUENCE: 46
MGHHHHHHSG ISLMAKIRQE HQSIAEKVAE LSLETREFLS VTTAKRQEQA EKQAQELQAF     60
YKDLQETSQQ FLSETAQARI AQAEKQAQEL LAFHKELQET SQQFLSATAQ ARIAQAEKQA    120
QELLAFYQEV RETSQQFLSA TAQARIAQAE KQAQELLAFH KELQETSQQF LSATADARTA    180
QAKEQKESLL KFRQDLFVSI FGSGRRRRRR RRRGGGPLGL AGEEEEEEEE                230

SEQ ID NO: 47           moltype = AA   length = 260
FEATURE                 Location/Qualifiers
REGION                  1..260
                        note = Synthetic construct
REGION                  1..260
                        note = MISC_FEATURE - Exemplary genetically engineered GvpC
                         variant GvpCWT-hPRM
source                  1..260
                        mol_type = protein
                        organism = synthetic construct
SEQUENCE: 47
MGHHHHHHSG ISLMAKIRQE HQSIAEKVAE LSLETREFLS VTTAKRQEQA EKQAQELQAF     60
YKDLQETSQQ FLSETAQARI AQAEKQAQEL LAFHKELQET SQQFLSATAQ ARIAQAEKQA    120
QELLAFYQEV RETSQQFLSA TAQARIAQAE KQAQELLAFH KELQETSQQF LSATADARTA    180
QAKEQKESLL KFRQDLFVSI FGARYRCCRS QSRSRYYRQR QRSRRRRRS CQTRRRAMRC     240
CRPRYRPRCR RHTGTRTRPL                                                260

SEQ ID NO: 48           moltype = AA   length = 304
FEATURE                 Location/Qualifiers
REGION                  1..304
                        note = Synthetic construct
REGION                  1..304
                        note = MISC_FEATURE - Exemplary genetically engineered GvpC
                         variant GvpCWT-LRP
source                  1..304
                        mol_type = protein
                        organism = synthetic construct
SEQUENCE: 48
MGHHHHHHSG ISLMAKIRQE HQSIAEKVAE LSLETREFLS VTTAKRQEQA EKQAQELQAF     60
YKDLQETSQQ FLSETAQARI AQAEKQAQEL LAFHKELQET SQQFLSATAQ ARIAQAEKQA    120
QELLAFYQEV RETSQQFLSA TAQARIAQAE KQAQELLAFH KELQETSQQF LSATADARTA    180
QAKEQKESLL KFRQDLFVSI FGSGKKKKKK KKKKKKKKKK KKKKKKKKKK KKKKKKKKKK    240
KKKKKKKKKK KKKKKKKKKK KKKKKKKKKK KKKKKKKKKK KKKKKKKKKK KKKKKKKKKK    300
KKKK                                                                 304

SEQ ID NO: 49           moltype = AA   length = 225
FEATURE                 Location/Qualifiers
REGION                  1..225
                        note = Synthetic construct
```

```
REGION                        1..225
                              note = MISC_FEATURE - Exemplary genetically engineered GvpC
                                variant GvpCWT-mCD47
source                        1..225
                              mol_type = protein
                              organism = synthetic construct
SEQUENCE: 49
MGHHHHHHSG ISLMAKIRQE HQSIAEKVAE LSLETREFLS VTTAKRQEQA EKQAQELQAF   60
YKDLQETSQQ FLSETAQARI AQAEKQAQEL LAFHKELQET SQQFLSATAQ ARIAQAEKQA  120
QELLAFYQEV RETSQQFLSA TAQARIAQAE KQAQELLAFH KELQETSQQF LSATADARTA  180
QAKEQKESLL KFRQDLFVSI FGSGGNYTCE VTELTREGET IIELK                  225

SEQ ID NO: 50                 moltype = AA   length = 212
FEATURE                       Location/Qualifiers
REGION                        1..212
                              note = Synthetic construct
REGION                        1..212
                              note = MISC_FEATURE - Exemplary genetically engineered GvpC
                                variant GvpCWT-R8
source                        1..212
                              mol_type = protein
                              organism = synthetic construct
SEQUENCE: 50
MGHHHHHHSG ISLMAKIRQE HQSIAEKVAE LSLETREFLS VTTAKRQEQA EKQAQELQAF   60
YKDLQETSQQ FLSETAQARI AQAEKQAQEL LAFHKELQET SQQFLSATAQ ARIAQAEKQA  120
QELLAFYQEV RETSQQFLSA TAQARIAQAE KQAQELLAFH KELQETSQQF LSATADARTA  180
QAKEQKESLL KFRQDLFVSI FGSGRRRRRR RR                                212

SEQ ID NO: 51                 moltype = AA   length = 213
FEATURE                       Location/Qualifiers
REGION                        1..213
                              note = Synthetic construct
REGION                        1..213
                              note = MISC_FEATURE - Exemplary genetically engineered GvpC
                                variant GvpCWT-RGD
source                        1..213
                              mol_type = protein
                              organism = synthetic construct
SEQUENCE: 51
MGHHHHHHSG ISLMAKIRQE HQSIAEKVAE LSLETREFLS VTTAKRQEQA EKQAQELQAF   60
YKDLQETSQQ FLSETAQARI AQAEKQAQEL LAFHKELQET SQQFLSATAQ ARIAQAEKQA  120
QELLAFYQEV RETSQQFLSA TAQARIAQAE KQAQELLAFH KELQETSQQF LSATADARTA  180
QAKEQKESLL KFRQDLFVSI FGSGCDCRGD CFC                               213

SEQ ID NO: 52                 moltype = AA   length = 213
FEATURE                       Location/Qualifiers
REGION                        1..213
                              note = Synthetic construct
REGION                        1..213
                              note = MISC_FEATURE - Exemplary genetically engineered GvpC
                                variant GvpCWT-RDG
source                        1..213
                              mol_type = protein
                              organism = synthetic construct
SEQUENCE: 52
MGHHHHHHSG ISLMAKIRQE HQSIAEKVAE LSLETREFLS VTTAKRQEQA EKQAQELQAF   60
YKDLQETSQQ FLSETAQARI AQAEKQAQEL LAFHKELQET SQQFLSATAQ ARIAQAEKQA  120
QELLAFYQEV RETSQQFLSA TAQARIAQAE KQAQELLAFH KELQETSQQF LSATADARTA  180
QAKEQKESLL KFRQDLFVSI FGSGCDCRDG CFC                               213

SEQ ID NO: 53                 moltype = AA   length = 203
FEATURE                       Location/Qualifiers
REGION                        1..203
                              note = Synthetic construct
REGION                        1..203
                              note = MISC_FEATURE - Exemplary genetically engineered GvpC
                                variant GvpCWT
source                        1..203
                              mol_type = protein
                              organism = synthetic construct
SEQUENCE: 53
MGISLMAKIR QEHQSIAEKV AELSLETREF LSVTTAKRQE QAEKQAQELQ AFYKDLQETS   60
QQFLSETAQA RIAQAEKQAQ ELLAFHKELQ ETSQQFLSAT AQARIAQAEK QAQELLAFYQ  120
EVRETSQQFL SATAQARIAQ AEKQAQELLA FHKELQETSQ QFLSATADAR TAQAKEQKES  180
LLKFRQDLFV SIFGSLEHHH HHH                                          203

SEQ ID NO: 54                 moltype = AA   length = 220
FEATURE                       Location/Qualifiers
REGION                        1..220
```

```
                         note = Synthetic construct
REGION                   1..220
                         note = MISC_FEATURE - Exemplary genetically engineered GvpC
                            variant GvpC-SpyTag
source                   1..220
                         mol_type = protein
                         organism = synthetic construct
SEQUENCE: 54
MGISLMAKIR QEHQSIAEKV AELSLETREF LSVTTAKRQE QAEKQAQELQ AFYKDLQETS       60
QQFLSETAQA RIAQAEKQAQ ELLAFHKELQ ETSQQFLSAT AQARIAQAEK QAQELLAFYQ      120
EVRETSQQFL SATAQARIAQ AEKQAQELLA FHKELQETSQ QFLSATADAR TAQAKEQKES      180
LLKFRQDLFV SIFGSGAHIV MVDAYKPTKG SGLEHHHHHH                            220

SEQ ID NO: 55            moltype = AA  length = 137
FEATURE                  Location/Qualifiers
REGION                   1..137
                         note = Synthetic construct
REGION                   1..137
                         note = MISC_FEATURE - Exemplary genetically engineered GvpC
                            variant N-rep1to3-C
source                   1..137
                         mol_type = protein
                         organism = synthetic construct
SEQUENCE: 55
MGISLMAKIR QEHQSIAEKV AELSLETREF LSVTTAKRQE QAEKQAQELQ AFYKDLQETS       60
QQFLSETAQA RIAQAEKQAQ ELLAFHKELQ ETSQQFLSAT AQARIAQAEK QAQELLAFRQ      120
DLFVSIFGSL EHHHHHH                                                    137

SEQ ID NO: 56            moltype = AA  length = 104
FEATURE                  Location/Qualifiers
REGION                   1..104
                         note = Synthetic construct
REGION                   1..104
                         note = MISC_FEATURE - Exemplary genetically engineered GvpC
                            variant N-rep1to2-C
source                   1..104
                         mol_type = protein
                         organism = synthetic construct
SEQUENCE: 56
MGISLMAKIR QEHQSIAEKV AELSLETREF LSVTTAKRQE QAEKQAQELQ AFYKDLQETS       60
QQFLSETAQA RIAQAEKQAQ ELLAFRQDLF VSIFGSLEHH HHHH                       104

SEQ ID NO: 57            moltype = AA  length = 170
FEATURE                  Location/Qualifiers
REGION                   1..170
                         note = Synthetic construct
REGION                   1..170
                         note = MISC_FEATURE - Exemplary genetically engineered GvpC
                            variant N-rep1to4-C
source                   1..170
                         mol_type = protein
                         organism = synthetic construct
SEQUENCE: 57
MGISLMAKIR QEHQSIAEKV AELSLETREF LSVTTAKRQE QAEKQAQELQ AFYKDLQETS       60
QQFLSETAQA RIAQAEKQAQ ELLAFHKELQ ETSQQFLSAT AQARIAQAEK QAQELLAFYQ      120
EVRETSQQFL SATAQARIAQ AEKQAQELLA FRQDLFVSIF GSLEHHHHHH                 170

SEQ ID NO: 58            moltype = AA  length = 44
FEATURE                  Location/Qualifiers
REGION                   1..44
                         note = MISC_FEATURE - GvpC repeat r7
source                   1..44
                         mol_type = protein
                         organism = Halobacterium salinarum
SEQUENCE: 58
DAFVAFARDF YGHEITAEEG AAEAEAEPVE ADADVEAEAE VSPD                        44

SEQ ID NO: 59            moltype = AA  length = 40
FEATURE                  Location/Qualifiers
REGION                   1..40
                         note = MISC_FEATURE - GvpC repeat r6
source                   1..40
                         mol_type = protein
                         organism = Halobacterium salinarum
SEQUENCE: 59
DAFAEYRDEF YRIEVEALLE AINDFQQDIG DFRAEFETTE                             40

SEQ ID NO: 60            moltype = AA  length = 32
FEATURE                  Location/Qualifiers
```

```
REGION                  1..32
                        note = MISC_FEATURE - GvpC repeat r5
source                  1..32
                        mol_type = protein
                        organism = Halobacterium salinarum
SEQUENCE: 60
DAFDNYAGDF DAEIDQLHAA IADQHDSFDA TA                                      32

SEQ ID NO: 61           moltype = AA  length = 32
FEATURE                 Location/Qualifiers
REGION                  1..32
                        note = MISC_FEATURE - GvpC repeat r2
source                  1..32
                        mol_type = protein
                        organism = Halobacterium salinarum
SEQUENCE: 61
DAFHTYGDEF AAEVDHLRAD IDAQRDVIRE MQ                                      32

SEQ ID NO: 62           moltype = AA  length = 38
FEATURE                 Location/Qualifiers
REGION                  1..38
                        note = MISC_FEATURE - GvpC repeat r3
source                  1..38
                        mol_type = protein
                        organism = Halobacterium salinarum
SEQUENCE: 62
DAFEAYADIF ATDIADKQDI GNLLAAIEAL RTEMNSTH                                38

SEQ ID NO: 63           moltype = AA  length = 39
FEATURE                 Location/Qualifiers
REGION                  1..39
                        note = MISC_FEATURE - GvpC repeat r1
source                  1..39
                        mol_type = protein
                        organism = Halobacterium salinarum
SEQUENCE: 63
QEFESYADEF AADITAKQDD VSDLVDAITD FQAEMTNTT                               39

SEQ ID NO: 64           moltype = AA  length = 38
FEATURE                 Location/Qualifiers
REGION                  1..38
                        note = MISC_FEATURE - GvpC repeat r4
source                  1..38
                        mol_type = protein
                        organism = Halobacterium salinarum
SEQUENCE: 64
GAFEAYADDF AADVAALRDI SDLVAAIDDF QEEFIAVQ                                38

SEQ ID NO: 65           moltype = AA  length = 42
FEATURE                 Location/Qualifiers
REGION                  1..42
                        note = MISC_FEATURE - GvpC repeat r7
source                  1..42
                        mol_type = protein
                        organism = Haloferax mediterranei
SEQUENCE: 65
EAFASFARDF YGQGAAPMAT PLNNAAETAV TGTETEVDIP PI                           42

SEQ ID NO: 66           moltype = AA  length = 40
FEATURE                 Location/Qualifiers
REGION                  1..40
                        note = MISC_FEATURE - GvpC repeat r6
source                  1..40
                        mol_type = protein
                        organism = Haloferax mediterranei
SEQUENCE: 66
DAFLQYREEF HGVEVQSLLD NIAAFQREMG DYRKAFETTE                              40

SEQ ID NO: 67           moltype = AA  length = 38
FEATURE                 Location/Qualifiers
REGION                  1..38
                        note = MISC_FEATURE - GvpC repeat r1
source                  1..38
                        mol_type = protein
                        organism = Haloferax mediterranei
SEQUENCE: 67
QAFAAYADEF AADVDDKRDV SELVDGIDTL RTEMNSTN                                38

SEQ ID NO: 68           moltype = AA  length = 38
```

```
FEATURE                 Location/Qualifiers
REGION                  1..38
                        note = MISC_FEATURE - GvpC repeat r3
source                  1..38
                        mol_type = protein
                        organism = Haloferax mediterranei
SEQUENCE: 68
DAFDAYADIF ATDVAEMQDV SDLLAAIDDL RAEMDETH                                    38

SEQ ID NO: 69           moltype = AA  length = 38
FEATURE                 Location/Qualifiers
REGION                  1..38
                        note = MISC_FEATURE - GvpC repeat r4
source                  1..38
                        mol_type = protein
                        organism = Haloferax mediterranei
SEQUENCE: 69
EAFDAYADAF VTDVATLRDV SDLLTAISEL QSEFVSVQ                                    38

SEQ ID NO: 70           moltype = AA  length = 25
FEATURE                 Location/Qualifiers
REGION                  1..25
                        note = MISC_FEATURE - GvpC repeat r2
source                  1..25
                        mol_type = protein
                        organism = Haloferax mediterranei
SEQUENCE: 70
DAFRAYSEEF AADVEHFHTS VADRR                                                  25

SEQ ID NO: 71           moltype = AA  length = 32
FEATURE                 Location/Qualifiers
REGION                  1..32
                        note = MISC_FEATURE - GvpC repeat r5
source                  1..32
                        mol_type = protein
                        organism = Haloferax mediterranei
SEQUENCE: 71
GEFNGYASEF GADIDQFHAV VAEKRDGHKD VA                                          32

SEQ ID NO: 72           moltype = AA  length = 33
FEATURE                 Location/Qualifiers
REGION                  1..33
                        note = MISC_FEATURE - GvpC repeat r1
source                  1..33
                        mol_type = protein
                        organism = Anabaena flos-aquae
SEQUENCE: 72
VAELSLETRE FLSVTTAKRQ EQAEKQAQEL QAF                                         33

SEQ ID NO: 73           moltype = AA  length = 33
FEATURE                 Location/Qualifiers
REGION                  1..33
                        note = MISC_FEATURE - GvpC repeat r5
source                  1..33
                        mol_type = protein
                        organism = Anabaena flos-aquae
SEQUENCE: 73
HKELQETSQQ FLSATADART AQAKEQKESL LKF                                         33

SEQ ID NO: 74           moltype = AA  length = 33
FEATURE                 Location/Qualifiers
REGION                  1..33
                        note = MISC_FEATURE - GvpC repeat r4
source                  1..33
                        mol_type = protein
                        organism = Anabaena flos-aquae
SEQUENCE: 74
YQEVRETSQQ FLSATAQARI AQAEKQAQEL LAF                                         33

SEQ ID NO: 75           moltype = AA  length = 33
FEATURE                 Location/Qualifiers
REGION                  1..33
                        note = MISC_FEATURE - GvpC repeat r2
source                  1..33
                        mol_type = protein
                        organism = Anabaena flos-aquae
SEQUENCE: 75
YKDLQETSQQ FLSETAQARI AQAEKQAQEL LAF                                         33
```

```
SEQ ID NO: 76            moltype = AA   length = 33
FEATURE                  Location/Qualifiers
REGION                   1..33
                         note = MISC_FEATURE - GvpC repeat r3
source                   1..33
                         mol_type = protein
                         organism = Anabaena flos-aquae
SEQUENCE: 76
HKELQETSQQ FLSATAQARI AQAEKQAQEL LAF                                           33

SEQ ID NO: 77            moltype = AA   length = 33
FEATURE                  Location/Qualifiers
REGION                   1..33
                         note = MISC_FEATURE - GvpC repeat r1
source                   1..33
                         mol_type = protein
                         organism = Microchaete diplosiphon
SEQUENCE: 77
VTQLFKDTQE FLSVTTAQRQ AQAKEQAENL HQF                                           33

SEQ ID NO: 78            moltype = AA   length = 33
FEATURE                  Location/Qualifiers
REGION                   1..33
                         note = MISC_FEATURE - GvpC repeat r3
source                   1..33
                         mol_type = protein
                         organism = Microchaete diplosiphon
SEQUENCE: 78
HKEMAENTQE FLSETAKERM AQAQEQARQL REF                                           33

SEQ ID NO: 79            moltype = AA   length = 33
FEATURE                  Location/Qualifiers
REGION                   1..33
                         note = MISC_FEATURE - GvpC repeat r4
source                   1..33
                         mol_type = protein
                         organism = Microchaete diplosiphon
SEQUENCE: 79
HQNLEQTTNE FLADTAKERM AQAQEQKQQL HQF                                           33

SEQ ID NO: 80            moltype = AA   length = 33
FEATURE                  Location/Qualifiers
REGION                   1..33
                         note = MISC_FEATURE - GvpC repeat r1
source                   1..33
                         mol_type = protein
                         organism = Nostoc sp.
SEQUENCE: 80
VTQLFRETHE FLSATTAHRQ EQAKQQAQQL HQF                                           33

SEQ ID NO: 81            moltype = AA   length = 33
FEATURE                  Location/Qualifiers
REGION                   1..33
                         note = MISC_FEATURE - GvpC repeat r2
source                   1..33
                         mol_type = protein
                         organism = Nostoc sp.
SEQUENCE: 81
HQNLEQTTHE FLTETTTQRV AQAEAQANFL HKF                                           33

SEQ ID NO: 82            moltype = AA   length = 33
FEATURE                  Location/Qualifiers
REGION                   1..33
                         note = MISC_FEATURE - GvpC repeat r3
source                   1..33
                         mol_type = protein
                         organism = Nostoc sp.
SEQUENCE: 82
HQNLEQTTQE FLAETAKNRT EQAKAQSQYL QQF                                           33

SEQ ID NO: 83            moltype = AA   length = 33
FEATURE                  Location/Qualifiers
REGION                   1..33
                         note = MISC_FEATURE - GvpC repeat r1
source                   1..33
                         mol_type = protein
                         organism = Microcystis aeruginosa
SEQUENCE: 83
VAKLSQEVQA FLSDVKTERQ KQAQEQATAL RQS                                           33
```

```
SEQ ID NO: 84           moltype = AA  length = 33
FEATURE                 Location/Qualifiers
REGION                  1..33
                        note = MISC_FEATURE - GvpC repeat r2
source                  1..33
                        mol_type = protein
                        organism = Microcystis aeruginosa
SEQUENCE: 84
FQKVQQESHL FLTATQKQRL AQAEKQKEDL RQF                                   33

SEQ ID NO: 85           moltype = AA  length = 33
FEATURE                 Location/Qualifiers
REGION                  1..33
                        note = MISC_FEATURE - GvpC repeat r3
source                  1..33
                        mol_type = protein
                        organism = Microcystis aeruginosa
SEQUENCE: 85
QEQRLAAAKQ LDNDLRQQRL DRAKQLKEDL SQF                                   33

SEQ ID NO: 86           moltype = AA  length = 33
FEATURE                 Location/Qualifiers
REGION                  1..33
                        note = MISC_FEATURE - GvpC repeat r4
source                  1..33
                        mol_type = protein
                        organism = Microcystis aeruginosa
SEQUENCE: 86
QEQRLAEAKQ LANDLRQQHL DRAKQLKEDL SQF                                   33

SEQ ID NO: 87           moltype = AA  length = 33
FEATURE                 Location/Qualifiers
REGION                  1..33
                        note = MISC_FEATURE - GvpC repeat r5
source                  1..33
                        mol_type = protein
                        organism = Microcystis aeruginosa
SEQUENCE: 87
QEQRLAAAKQ LEDELRQLHL DRAKQVKDDL SQF                                   33

SEQ ID NO: 88           moltype = AA  length = 18
FEATURE                 Location/Qualifiers
REGION                  1..18
                        note = MISC_FEATURE - GvpC repeat r6
source                  1..18
                        mol_type = protein
                        organism = Microcystis aeruginosa
SEQUENCE: 88
QERRLAEAKQ LKDDLRQF                                                    18

SEQ ID NO: 89           moltype = AA  length = 46
FEATURE                 Location/Qualifiers
REGION                  1..46
                        note = Synthetic construct
REGION                  1..46
                        note = MISC_FEATURE - Consensus of all the repeats within
                         GvpC from Haloferaxmediterranei
source                  1..46
                        mol_type = protein
                        organism = synthetic construct
SEQUENCE: 89
DAFAAYADEF AADVDDFHDV SADLLDGIDD LQAEMNSTNK AFETTE                     46

SEQ ID NO: 90           moltype = AA  length = 37
FEATURE                 Location/Qualifiers
REGION                  1..37
                        note = Synthetic construct
REGION                  1..37
                        note = MISC_FEATURE - Consensus of all the repeats within
                         GvpC from Halobacteriumsalinarum
source                  1..37
                        mol_type = protein
                        organism = synthetic construct
SEQUENCE: 90
DAFEAYADEF AAEIDALADI SDLVDAIDDF QEFETTE                               37

SEQ ID NO: 91           moltype = AA  length = 33
FEATURE                 Location/Qualifiers
```

```
REGION                  1..33
                        note = Synthetic construct
REGION                  1..33
                        note = MISC_FEATURE - Consensus of all the repeats within
                         GvpC from Anabaena flos-aquae
source                  1..33
                        mol_type = protein
                        organism = synthetic construct
SEQUENCE: 91
HKELQETSQQ FLSATAQARI AQAEKQAQEL LAF                                          33

SEQ ID NO: 92           moltype = AA  length = 33
FEATURE                 Location/Qualifiers
REGION                  1..33
                        note = Synthetic construct
REGION                  1..33
                        note = MISC_FEATURE - Consensus of all the repeats within
                         GvpC from Microchaetediplosiphon
source                  1..33
                        mol_type = protein
                        organism = synthetic construct
SEQUENCE: 92
HKELEKDTQE FLSDTAKERM AQAKEQAEQL HQF                                          33

SEQ ID NO: 93           moltype = AA  length = 33
FEATURE                 Location/Qualifiers
REGION                  1..33
                        note = Synthetic construct
REGION                  1..33
                        note = MISC_FEATURE - Consensus of all the repeats within
                         GvpC from Nostoc sp.
source                  1..33
                        mol_type = protein
                        organism = synthetic construct
SEQUENCE: 93
HQNLEQTTHE FLAETTKNRT EQAKAQAQQL HQF                                          33
```